United States Patent
Winslow et al.

(10) Patent No.: US 8,372,122 B2
(45) Date of Patent: *Feb. 12, 2013

(54) LOW PROFILE SPINAL PROSTHESIS INCORPORATING A BONE ANCHOR HAVING A DEFLECTABLE POST AND A COMPOUND SPINAL ROD

(75) Inventors: Charles J. Winslow, Lafayette, CA (US); Steven T. Mitchell, Pleasant Hill, CA (US); John J. Flynn, Walnut Creek, CA (US); James F. Zucherman, San Francisco, CA (US); Ken Y. Hsu, San Francisco, CA (US); Henry A. Klyce, San Francisco, CA (US); H. Adam R. Klyce, Berkeley, CA (US)

(73) Assignee: Spartek Medical, Inc., Concord, CA (US)

( * ) Notice: Subject to any disclaimer, the term of this patent is extended or adjusted under 35 U.S.C. 154(b) by 144 days.

This patent is subject to a terminal disclaimer.

(21) Appl. No.: 13/098,280

(22) Filed: Apr. 29, 2011

(65) Prior Publication Data

US 2012/0143256 A1 Jun. 7, 2012

Related U.S. Application Data

(63) Continuation-in-part of application No. 12/959,200, filed on Dec. 2, 2010, now Pat. No. 8,257,397, and a continuation-in-part of application No. 12/629,811, filed on Dec. 2, 2009, now Pat. No. 8,216,281.

(30) Foreign Application Priority Data

Dec. 3, 2009 (WO) .................. PCT/US2009066567
Dec. 2, 2010 (WO) .................. PCT/US2010058776

(51) Int. Cl.
*A61B 17/70* (2006.01)

(52) U.S. Cl. ....................................................... 606/264
(58) Field of Classification Search .................. 606/254, 606/255, 257, 259, 261–267, 270, 272, 279, 606/300, 301, 305
See application file for complete search history.

(56) References Cited

U.S. PATENT DOCUMENTS

| 4,041,939 A | 8/1977 | Hall ................................ 128/69 |
| 4,065,817 A | 1/1978 | Branemark et al. ............. 3/1.91 |
| 4,274,401 A | 6/1981 | Miskew | |
| 4,347,845 A | 9/1982 | Mayfield ....................... 128/303 |

(Continued)

FOREIGN PATENT DOCUMENTS

| DE | 2649042 B1 | 10/1976 |
| DE | 3639810 A1 | 5/1988 |

(Continued)

OTHER PUBLICATIONS

Mekanika, Inc. Website, 2003; Mekanika—The Spinal Stabilization Company, product description for Modulus System, 2 pages, <http://mekanika.com/htm/modsystem.htm>.

(Continued)

*Primary Examiner* — Pedro Philogene
(74) *Attorney, Agent, or Firm* — Fliesler Meyer LLP

(57) ABSTRACT

A bone anchor comprising a self-centering ball-joint suitable for use in a spine stabilization prosthesis which supports the spine while providing for the preservation of spinal motion. The bone anchor has a deflectable ball-rod partially received in a socket of a housing formed in the head of the bone anchor. A centering rod received partially in the ball-rod and partially within the housing operates to align the ball-rod with the longitudinal axis of the bone anchor. Deflection of the ball-rod bends the centering rod which in turn applies a restoring force upon the ball-rod. The centering rod includes an inner-superelastic core and an outer polymer sheath.

29 Claims, 44 Drawing Sheets

U.S. PATENT DOCUMENTS

| | | | |
|---|---|---|---|
| 4,369,770 A | 1/1983 | Bacal et al. ................ | 128/69 |
| 4,382,438 A | 5/1983 | Jacobs ........................ | 128/69 |
| 4,409,968 A | 10/1983 | Drummond ................ | 128/69 |
| 4,411,259 A | 10/1983 | Drummond ................ | 128/69 |
| 4,422,451 A | 12/1983 | Kalamchi ................... | 128/69 |
| 4,479,491 A | 10/1984 | Martin ....................... | 128/92 |
| 4,567,885 A | 2/1986 | Androphy ................... | 128/92 |
| 4,573,454 A | 3/1986 | Hoffman .................... | 128/69 |
| 4,604,995 A | 8/1986 | Stephens et al. ........... | 128/69 |
| 4,611,580 A | 9/1986 | Wu ............................. | 128/69 |
| 4,611,581 A | 9/1986 | Steffee ....................... | 128/69 |
| 4,611,582 A | 9/1986 | Duff ........................... | 128/69 |
| 4,641,636 A | 2/1987 | Cotrel ........................ | 128/69 |
| 4,648,388 A | 3/1987 | Steffee ....................... | 128/69 |
| 4,653,481 A | 3/1987 | Howland et al. ............ | 128/69 |
| 4,653,489 A | 3/1987 | Tronzo ....................... | 128/92 |
| 4,655,199 A | 4/1987 | Steffee ....................... | 128/69 |
| 4,658,809 A | 4/1987 | Ulrich et al. ................ | 128/92 |
| 4,696,290 A | 9/1987 | Steffee ....................... | 128/69 |
| 4,719,905 A | 1/1988 | Steffee ....................... | 128/69 |
| 4,763,644 A | 8/1988 | Webb ......................... | 128/69 |
| 4,773,402 A | 9/1988 | Asher et al. ................ | 128/69 |
| 4,805,602 A | 2/1989 | Puno et al. .................. | 128/69 |
| 4,815,453 A | 3/1989 | Cotrel ........................ | 128/69 |
| 4,887,595 A | 12/1989 | Heinig et al. ............... | 606/61 |
| 4,913,134 A | 4/1990 | Luque ........................ | 128/69 |
| 4,946,458 A | 8/1990 | Harms et al. ............... | 606/61 |
| 4,950,269 A | 8/1990 | Gaines, Jr. .................. | 606/61 |
| 4,955,885 A | 9/1990 | Meyers ...................... | 606/53 |
| 4,987,892 A | 1/1991 | Krag et al. .................. | 606/61 |
| 5,005,562 A | 4/1991 | Cotrel ........................ | 128/69 |
| 5,024,213 A | 6/1991 | Asher et al. ................ | 128/69 |
| 5,030,220 A | 7/1991 | Howland .................... | 606/61 |
| 5,042,982 A | 8/1991 | Harms et al. ............... | 606/61 |
| 5,047,029 A | 9/1991 | Aebi et al. .................. | 606/61 |
| 5,067,955 A | 11/1991 | Cotrel ........................ | 606/61 |
| 5,074,864 A | 12/1991 | Cozad et al. ................ | 606/54 |
| 5,084,049 A | 1/1992 | Asher et al. ................ | 606/61 |
| 5,092,866 A | 3/1992 | Breard et al. ............... | 606/61 |
| 5,102,412 A | 4/1992 | Rogozinski ................. | 606/61 |
| 5,112,332 A | 5/1992 | Cozad et al. ................ | 606/61 |
| 5,113,685 A | 5/1992 | Asher et al. ................ | 72/458 |
| 5,116,334 A | 5/1992 | Cozad et al. | |
| 5,127,912 A | 7/1992 | Ray et al. ................... | 606/61 |
| 5,129,388 A | 7/1992 | Vignaud et al. ............. | 606/61 |
| 5,129,900 A | 7/1992 | Asher et al. ................ | 606/61 |
| 5,147,359 A | 9/1992 | Cozad et al. ................ | 606/61 |
| 5,154,718 A | 10/1992 | Cozad et al. ................ | 606/61 |
| 5,176,680 A | 1/1993 | Vignaud et al. ............. | 606/61 |
| 5,180,393 A | 1/1993 | Commarmond ............ | 623/13 |
| 5,190,543 A | 3/1993 | Schläpfer ................... | 606/61 |
| 5,201,734 A | 4/1993 | Cozad et al. ................ | 606/62 |
| 5,207,678 A | 5/1993 | Harms et al. ............... | 606/61 |
| 5,261,911 A | 11/1993 | Carl ............................ | 606/61 |
| 5,261,912 A | 11/1993 | Frigg ......................... | 606/61 |
| 5,261,913 A | 11/1993 | Marnay ...................... | 606/61 |
| 5,281,222 A | 1/1994 | Allard et al. ................ | 606/54 |
| 5,282,801 A | 2/1994 | Sherman .................... | 606/61 |
| 5,282,863 A | 2/1994 | Burton ....................... | 623/17 |
| 5,290,289 A | 3/1994 | Sanders et al. ............. | 606/61 |
| 5,312,402 A | 5/1994 | Schläpfer et al. ........... | 606/53 |
| 5,312,404 A | 5/1994 | Asher et al. ................ | 606/61 |
| 5,344,422 A | 9/1994 | Frigg ......................... | 606/61 |
| 5,346,493 A | 9/1994 | Stahurski et al. ........... | 606/61 |
| 5,360,429 A | 11/1994 | Jeanson et al. ............. | 606/61 |
| 5,360,431 A | 11/1994 | Puno et al. .................. | 606/72 |
| 5,374,267 A | 12/1994 | Siegal | |
| 5,380,325 A | 1/1995 | Lahille et al. .............. | 606/61 |
| 5,380,326 A | 1/1995 | Lin ............................. | 606/61 |
| 5,382,248 A | 1/1995 | Jacobson et al. ........... | 606/60 |
| 5,385,583 A | 1/1995 | Cotrel ........................ | 623/17 |
| 5,387,213 A | 2/1995 | Breard et al. ............... | 606/61 |
| 5,415,661 A | 5/1995 | Holmes ...................... | 606/69 |
| 5,429,639 A | 7/1995 | Judet .......................... | 606/61 |
| 5,437,672 A | 8/1995 | Alleyne | |
| 5,443,467 A | 8/1995 | Biedermann et al. ...... | 606/65 |
| 5,466,237 A | 11/1995 | Byrd, III et al. ............ | 606/61 |
| 5,474,555 A | 12/1995 | Puno et al. .................. | 606/73 |
| 5,480,442 A | 1/1996 | Bertanoli | |
| 5,487,742 A | 1/1996 | Cotrel ........................ | 606/61 |
| 5,496,321 A | 3/1996 | Puno et al. .................. | 606/61 |
| 5,498,264 A | 3/1996 | Schlapfer et al. ........... | 606/72 |
| 5,501,684 A | 3/1996 | Schlapfer et al. | |
| 5,520,689 A | 5/1996 | Schläpfer et al. ........... | 606/61 |
| 5,534,001 A | 7/1996 | Schlapfer et al. ........... | 606/61 |
| 5,536,268 A | 7/1996 | Griss .......................... | 606/61 |
| 5,540,688 A | 7/1996 | Navas ........................ | 606/61 |
| 5,545,167 A | 8/1996 | Lin ............................. | 606/61 |
| 5,549,607 A | 8/1996 | Olson et al. ................ | 606/61 |
| 5,562,737 A | 10/1996 | Graf ........................... | 623/17 |
| 5,569,248 A | 10/1996 | Mathews .................... | 606/61 |
| 5,591,166 A | 1/1997 | Bernhardt et al. | |
| 5,601,552 A | 2/1997 | Cotrel | |
| 5,609,592 A | 3/1997 | Brumfield et al. .......... | 606/61 |
| 5,609,593 A | 3/1997 | Errico et al. ................ | 606/61 |
| 5,611,800 A | 3/1997 | Davis et al. ................ | 606/61 |
| 5,624,441 A | 4/1997 | Sherman et al. ............ | 606/61 |
| 5,628,740 A | 5/1997 | Mullane ..................... | 606/61 |
| 5,630,816 A | 5/1997 | Kambin ...................... | 606/61 |
| 5,643,260 A | 7/1997 | Doherty ..................... | 606/61 |
| 5,645,599 A | 7/1997 | Samani ....................... | 623/17 |
| 5,651,789 A | 7/1997 | Cotrel ........................ | 606/61 |
| 5,653,708 A | 8/1997 | Howland .................... | 606/61 |
| 5,658,284 A | 8/1997 | Sebastian et al. ........... | 606/61 |
| 5,658,285 A | 8/1997 | Marnay et al. | |
| 5,667,506 A | 9/1997 | Sutterlin .................... | 606/61 |
| 5,667,507 A | 9/1997 | Corin et al. ................. | 606/61 |
| 5,669,910 A | 9/1997 | Korhonen et al. .......... | 606/61 |
| 5,672,175 A | 9/1997 | Martin ....................... | 606/61 |
| 5,672,176 A | 9/1997 | Biedermann et al. ...... | 606/61 |
| 5,676,665 A | 10/1997 | Bryan ........................ | 606/61 |
| 5,676,703 A | 10/1997 | Gelbard ..................... | 623/17 |
| 5,681,310 A | 10/1997 | Yuan et al. | |
| 5,681,311 A | 10/1997 | Foley et al. ................ | 606/61 |
| 5,681,319 A | 10/1997 | Biedermann et al. ...... | 606/104 |
| 5,683,391 A | 11/1997 | Boyd ......................... | 606/61 |
| 5,683,392 A | 11/1997 | Richelsoph et al. ........ | 606/61 |
| 5,683,393 A | 11/1997 | Ralph ........................ | 606/61 |
| 5,688,272 A | 11/1997 | Montague et al. .......... | 606/61 |
| 5,688,273 A | 11/1997 | Errico et al. ................ | 606/61 |
| 5,690,629 A | 11/1997 | Asher et al. ................ | 606/61 |
| 5,690,632 A | 11/1997 | Schwartz et al. ........... | 606/73 |
| 5,690,633 A | 11/1997 | Taylor et al. ............... | 606/73 |
| 5,693,053 A | 12/1997 | Estes .......................... | 606/61 |
| 5,697,929 A | 12/1997 | Mellinger .................. | 606/61 |
| 5,700,292 A | 12/1997 | Margulies .................. | 623/17 |
| 5,702,392 A | 12/1997 | Wu et al. .................... | 606/61 |
| 5,702,394 A | 12/1997 | Henry et al. ................ | 606/61 |
| 5,702,395 A | 12/1997 | Hopf .......................... | 606/61 |
| 5,702,396 A | 12/1997 | Hoenig et al. .............. | 606/69 |
| 5,702,399 A | 12/1997 | Kilpela et al. .............. | 606/72 |
| 5,702,452 A | 12/1997 | Argenson et al. .......... | 623/17 |
| 5,713,900 A | 2/1998 | Benzel et al. ............... | 606/61 |
| 5,713,904 A | 2/1998 | Errico et al. ................ | 606/73 |
| 5,716,355 A | 2/1998 | Jackson et al. ............. | 606/61 |
| 5,716,356 A | 2/1998 | Biedermann et al. ...... | 606/61 |
| 5,716,357 A | 2/1998 | Rogozinski ................. | 606/61 |
| 5,716,358 A | 2/1998 | Ochoa et al. ............... | 606/62 |
| 5,716,359 A | 2/1998 | Ojima et al. ................ | 606/76 |
| 5,720,751 A | 2/1998 | Jackson ...................... | 606/86 |
| 5,725,528 A | 3/1998 | Errico et al. ................ | 606/61 |
| 5,725,582 A | 3/1998 | Bevan et al. ................ | 623/17 |
| 5,728,098 A | 3/1998 | Sherman et al. ............ | 606/61 |
| 5,733,286 A | 3/1998 | Errico et al. ................ | 606/61 |
| 5,735,851 A | 4/1998 | Errico et al. ................ | 606/61 |
| 5,741,254 A | 4/1998 | Henry et al. ................ | 606/61 |
| 5,743,907 A | 4/1998 | Asher et al. ................ | 606/61 |
| 5,743,911 A | 4/1998 | Cotrel ........................ | 606/61 |
| 5,752,957 A | 5/1998 | Ralph et al. ................ | 606/61 |
| 5,766,254 A | 6/1998 | Gelbard ..................... | 623/17 |
| 5,776,135 A | 7/1998 | Errico et al. | |
| 5,782,833 A | 7/1998 | Haider ....................... | 606/61 |
| 5,785,711 A | 7/1998 | Errico et al. ................ | 606/61 |
| 5,797,911 A | 8/1998 | Sherman et al. ............ | 606/61 |
| 5,800,435 A | 9/1998 | Errico et al. ................ | 606/61 |
| 5,810,819 A | 9/1998 | Errico et al. ................ | 606/61 |
| 5,863,293 A | 1/1999 | Richelsoph ................ | 606/61 |

| Patent | Kind | Date | Name | Class |
|---|---|---|---|---|
| 5,868,745 | A | 2/1999 | Alleyne | |
| 5,879,350 | A | 3/1999 | Sherman et al. | 606/61 |
| 5,885,286 | A | 3/1999 | Sherman et al. | 606/61 |
| 5,891,145 | A | 4/1999 | Morrison et al. | 606/61 |
| 5,899,904 | A | 5/1999 | Errico et al. | 606/61 |
| RE36,221 | E | 6/1999 | Breard et al. | 606/61 |
| 5,910,142 | A | 6/1999 | Tatar | 606/61 |
| 5,925,047 | A | 7/1999 | Errico et al. | 606/65 |
| 5,928,231 | A | 7/1999 | Klein et al. | 606/60 |
| 5,928,232 | A | 7/1999 | Howland et al. | 606/61 |
| 5,928,233 | A | 7/1999 | Apfelbaum et al. | 606/61 |
| 5,947,965 | A | 9/1999 | Bryan | 606/61 |
| 5,947,969 | A | 9/1999 | Errico et al. | 606/61 |
| 5,954,725 | A | 9/1999 | Sherman et al. | 606/78 |
| 5,961,517 | A | 10/1999 | Biedermann et al. | 606/61 |
| 5,964,760 | A | 10/1999 | Richelsoph | 606/61 |
| 5,980,521 | A | 11/1999 | Montague et al. | 606/61 |
| 5,980,523 | A | 11/1999 | Jackson | 606/61 |
| 5,984,922 | A | 11/1999 | McKay | 606/61 |
| 5,989,251 | A | 11/1999 | Nichols | 606/61 |
| 5,989,254 | A | 11/1999 | Katz | 606/73 |
| 6,001,098 | A | 12/1999 | Metz-Stavenhagen et al. | 606/61 |
| 6,004,322 | A | 12/1999 | Bernstein | 606/61 |
| 6,010,503 | A | 1/2000 | Richelsoph et al. | 606/61 |
| 6,015,409 | A | 1/2000 | Jackson | 606/61 |
| 6,033,410 | A | 3/2000 | McLean et al. | |
| 6,036,693 | A | 3/2000 | Yuan et al. | 606/61 |
| 6,050,997 | A | 4/2000 | Mullane | 606/61 |
| 6,053,917 | A | 4/2000 | Sherman et al. | 606/61 |
| 6,063,089 | A | 5/2000 | Errico et al. | 606/61 |
| 6,077,262 | A | 6/2000 | Schläpfer et al. | 606/61 |
| 6,086,588 | A | 7/2000 | Ameil et al. | 606/61 |
| 6,090,111 | A | 7/2000 | Nichols | 606/61 |
| 6,096,039 | A | 8/2000 | Stoltenberg et al. | 606/61 |
| 6,113,600 | A | 9/2000 | Drummond et al. | 606/61 |
| 6,113,601 | A | 9/2000 | Tatar | 606/61 |
| 6,123,706 | A | 9/2000 | Lange | |
| 6,127,597 | A | 10/2000 | Beyar et al. | 623/16 |
| 6,132,430 | A | 10/2000 | Wagner | 606/61 |
| 6,132,434 | A | 10/2000 | Sherman et al. | 606/78 |
| 6,132,464 | A | 10/2000 | Martin | |
| 6,136,000 | A | 10/2000 | Louis et al. | 606/61 |
| 6,146,383 | A | 11/2000 | Studer et al. | 606/61 |
| 6,171,311 | B1 | 1/2001 | Richelsoph | 606/61 |
| 6,193,720 | B1 | 2/2001 | Yuan et al. | 606/61 |
| 6,197,028 | B1 | 3/2001 | Ray et al. | 606/61 |
| 6,210,413 | B1 | 4/2001 | Justis et al. | 606/61 |
| 6,217,578 | B1 | 4/2001 | Crozet et al. | 606/61 |
| 6,248,106 | B1 | 6/2001 | Ferree | 606/61 |
| 6,254,602 | B1 | 7/2001 | Justis | 606/61 |
| 6,261,287 | B1 | 7/2001 | Metz-Stavenhagen | 606/61 |
| 6,267,765 | B1 | 7/2001 | Taylor et al. | |
| 6,273,888 | B1 | 8/2001 | Justis | 606/61 |
| 6,273,914 | B1 | 8/2001 | Papas | 623/17.11 |
| 6,280,442 | B1 | 8/2001 | Barker et al. | |
| 6,280,443 | B1 | 8/2001 | Gu et al. | 606/61 |
| 6,287,311 | B1 | 9/2001 | Sherman et al. | 606/78 |
| 6,293,949 | B1 | 9/2001 | Justis et al. | 606/61 |
| 6,302,882 | B1 | 10/2001 | Lin et al. | |
| 6,302,888 | B1 | 10/2001 | Mellinger et al. | 606/73 |
| 6,309,391 | B1 | 10/2001 | Crandall et al. | 606/61 |
| 6,325,802 | B1 | 12/2001 | Frigg | 606/61 |
| 6,328,740 | B1 | 12/2001 | Richelsoph | 606/61 |
| 6,344,057 | B1 | 2/2002 | Rabbe et al. | 623/17 |
| 6,355,040 | B1 | 3/2002 | Richelsoph et al. | 606/61 |
| 6,379,354 | B1 | 4/2002 | Rogozinski | 606/61 |
| 6,402,749 | B1 | 6/2002 | Ashman | 606/61 |
| 6,402,751 | B1 | 6/2002 | Hoeck et al. | 606/61 |
| 6,402,752 | B2 | 6/2002 | Schäffler-Wachter et al. | 606/61 |
| 6,413,257 | B1 | 7/2002 | Lin et al. | 606/61 |
| 6,416,515 | B1 | 7/2002 | Wagner | 606/61 |
| 6,423,064 | B1 | 7/2002 | Kluger | 606/61 |
| 6,440,169 | B1 | 8/2002 | Elberg et al. | 623/17.16 |
| 6,451,021 | B1 | 9/2002 | Ralph et al. | 606/61 |
| 6,454,773 | B1 | 9/2002 | Sherman et al. | 606/78 |
| 6,458,131 | B1 | 10/2002 | Ray | 606/61 |
| 6,458,132 | B2 | 10/2002 | Choi | 606/61 |
| 6,468,276 | B1 | 10/2002 | McKay | 606/61 |
| 6,471,705 | B1 | 10/2002 | Biedermann et al. | 606/61 |
| 6,475,219 | B1 | 11/2002 | Shelokov | |
| 6,478,797 | B1 | 11/2002 | Paul | 606/61 |
| 6,482,207 | B1 | 11/2002 | Errico | 606/61 |
| 6,485,491 | B1 | 11/2002 | Farris et al. | 606/61 |
| 6,488,681 | B2 | 12/2002 | Martin et al. | 606/61 |
| 6,520,962 | B1 | 2/2003 | Taylor et al. | 606/61 |
| 6,520,990 | B1 | 2/2003 | Ray | 623/17.11 |
| 6,537,276 | B2 | 3/2003 | Metz-Stavenhagen | 606/61 |
| 6,540,748 | B2 | 4/2003 | Lombardo | 606/61 |
| 6,540,749 | B2 | 4/2003 | Schäfer et al. | 606/61 |
| 6,547,789 | B1 | 4/2003 | Ventre et al. | 606/61 |
| 6,554,831 | B1 | 4/2003 | Rivard et al. | |
| 6,554,832 | B2 | 4/2003 | Shluzas | 606/61 |
| 6,554,834 | B1 | 4/2003 | Crozet et al. | 606/65 |
| 6,565,565 | B1 | 5/2003 | Yuan et al. | 606/61 |
| 6,565,566 | B1 | 5/2003 | Wagner et al. | 606/61 |
| 6,565,567 | B1 | 5/2003 | Haider | 606/61 |
| 6,565,605 | B2 | 5/2003 | Goble et al. | 623/17.11 |
| 6,572,617 | B1 | 6/2003 | Senegas | 606/61 |
| 6,572,653 | B1 | 6/2003 | Simonson | 623/17.13 |
| 6,579,290 | B1 | 6/2003 | Hardcastle et al. | 606/61 |
| 6,585,737 | B1 | 7/2003 | Baccelli et al. | 606/61 |
| 6,589,243 | B1 | 7/2003 | Viart et al. | |
| 6,616,669 | B2 | 9/2003 | Ogilvie et al. | 606/61 |
| 6,623,485 | B2 | 9/2003 | Doubler et al. | 606/61 |
| 6,626,905 | B1 | 9/2003 | Schmiel et al. | 606/61 |
| 6,626,908 | B2 | 9/2003 | Cooper et al. | 606/61 |
| 6,645,207 | B2 | 11/2003 | Dixon et al. | 606/61 |
| 6,652,526 | B1 | 11/2003 | Arafiles | 606/61 |
| 6,656,181 | B2 | 12/2003 | Dixon et al. | 606/69 |
| 6,660,004 | B2 | 12/2003 | Barker et al. | 606/61 |
| 6,660,005 | B2 | 12/2003 | Toyama et al. | 606/61 |
| 6,676,661 | B1 | 1/2004 | Martin Benlloch et al. | |
| 6,695,845 | B2 | 2/2004 | Dixon et al. | 606/70 |
| 6,706,045 | B2 | 3/2004 | Lin et al. | 606/61 |
| 6,709,434 | B1 | 3/2004 | Gournay et al. | 606/61 |
| 6,716,213 | B2 | 4/2004 | Shitoto | 606/61 |
| 6,716,214 | B1 | 4/2004 | Jackson | 606/61 |
| 6,726,689 | B2 | 4/2004 | Jackson | 606/73 |
| 6,736,820 | B2 | 5/2004 | Biedermann et al. | 606/73 |
| 6,740,086 | B2 | 5/2004 | Richelsoph | |
| 6,749,614 | B2 | 6/2004 | Teitelbaum et al. | 606/61 |
| 6,752,807 | B2 | 6/2004 | Lin et al. | 606/61 |
| 6,755,829 | B1 | 6/2004 | Bono et al. | 606/61 |
| 6,755,835 | B2 | 6/2004 | Schultheiss et al. | 606/73 |
| 6,761,719 | B2 | 7/2004 | Justis et al. | 606/61 |
| 6,783,526 | B1 | 8/2004 | Lin et al. | 606/61 |
| 6,783,527 | B2 | 8/2004 | Drewry et al. | 606/61 |
| 6,786,907 | B2 | 9/2004 | Lange | 606/61 |
| 6,793,656 | B1 | 9/2004 | Mathews | 606/61 |
| 6,805,695 | B2 | 10/2004 | Keith et al. | 606/61 |
| 6,805,714 | B2 | 10/2004 | Sutcliffe | 623/17.11 |
| 6,811,567 | B2 | 11/2004 | Reiley | 623/17.11 |
| 6,827,743 | B2 | 12/2004 | Eisermann et al. | |
| 6,832,999 | B2 | 12/2004 | Ueyama et al. | 606/61 |
| 6,840,940 | B2 | 1/2005 | Ralph et al. | 606/61 |
| 6,843,791 | B2 | 1/2005 | Serhan | 606/61 |
| 6,852,128 | B2 | 2/2005 | Lange | 623/17.11 |
| 6,858,029 | B2 | 2/2005 | Yeh | |
| 6,858,030 | B2 | 2/2005 | Martin et al. | 606/61 |
| 6,869,433 | B2 | 3/2005 | Glascott | 606/73 |
| 6,875,211 | B2 | 4/2005 | Nichols et al. | 606/61 |
| 6,881,215 | B2 | 4/2005 | Assaker et al. | 606/61 |
| 6,883,520 | B2 | 4/2005 | Lambrecht | 128/898 |
| 6,887,242 | B2 | 5/2005 | Doubler et al. | 606/61 |
| 6,899,714 | B2 | 5/2005 | Vaughan | 606/61 |
| 6,918,911 | B2 | 7/2005 | Biedermann et al. | 606/61 |
| 6,932,817 | B2 | 8/2005 | Baynham et al. | 606/61 |
| 6,945,974 | B2 | 9/2005 | Dalton | 606/70 |
| 6,951,561 | B2 | 10/2005 | Warren et al. | 606/73 |
| 6,964,666 | B2 | 11/2005 | Jackson | 606/61 |
| 6,966,910 | B2 | 11/2005 | Ritland | 606/61 |
| 6,986,771 | B2 | 1/2006 | Paul et al. | 606/61 |
| 6,991,632 | B2 | 1/2006 | Ritland | 606/61 |
| 7,008,423 | B2 | 3/2006 | Assaker et al. | 606/61 |
| 7,011,685 | B2 | 3/2006 | Arnin et al. | 623/17.16 |
| 7,018,378 | B2 | 3/2006 | Biedermann et al. | 606/61 |
| 7,018,379 | B2 | 3/2006 | Drewry | 606/61 |
| 7,022,122 | B2 | 4/2006 | Amrein et al. | 606/61 |

| Patent No. | Date | Inventor(s) | Class |
|---|---|---|---|
| 7,029,475 B2 | 4/2006 | Panjabi | 606/61 |
| 7,033,392 B2 | 4/2006 | Schmiel | |
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,991 B2 | 9/2006 | Dixon | |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,137,985 B2 | 11/2006 | Jahng | |
| 7,163,538 B2 | 1/2007 | Altarac et al. | |
| 7,189,235 B2 | 3/2007 | Cauthen | |
| 7,214,227 B2 | 5/2007 | Colleran et al. | 606/61 |
| 7,250,052 B2 | 7/2007 | Landry et al. | 606/61 |
| 7,270,665 B2 | 9/2007 | Morrison et al. | |
| 7,282,064 B2 | 10/2007 | Chin | 623/17.15 |
| 7,294,128 B2 | 11/2007 | Alleyne et al. | |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,309,355 B2 | 12/2007 | Donnelly et al. | |
| 7,326,210 B2 | 2/2008 | Jahng et al. | 606/61 |
| 7,335,201 B2 | 2/2008 | Doubler et al. | 606/61 |
| 7,338,490 B2 | 3/2008 | Ogilvie et al. | |
| 7,338,491 B2 | 3/2008 | Baker et al. | |
| 7,344,539 B2 | 3/2008 | Serhan et al. | |
| 7,361,196 B2 | 4/2008 | Fallin et al. | |
| 7,377,923 B2 | 5/2008 | Purcell et al. | |
| 7,445,627 B2 | 11/2008 | Hawkes et al. | |
| 7,455,684 B2 | 11/2008 | Gradel et al. | |
| 7,476,238 B2 | 1/2009 | Panjabi | |
| 7,479,156 B2 | 1/2009 | Lourdel et al. | |
| 7,481,828 B2 | 1/2009 | Mazda et al. | |
| 7,491,218 B2 | 2/2009 | Landry et al. | |
| 7,503,924 B2 | 3/2009 | Lee et al. | |
| 7,513,905 B2 | 4/2009 | Jackson | |
| 7,513,911 B2 | 4/2009 | Lambrecht et al. | |
| 7,520,879 B2 | 4/2009 | Justis et al. | |
| 7,530,992 B2 | 5/2009 | Biedermann et al. | |
| 7,533,672 B2 | 5/2009 | Morgan et al. | |
| 7,553,320 B2 | 6/2009 | Molz, IV et al. | |
| 7,553,329 B2 | 6/2009 | Lambrecht et al. | |
| 7,559,943 B2 | 7/2009 | Mujwid | |
| 7,563,274 B2 | 7/2009 | Justis et al. | |
| 7,572,279 B2 | 8/2009 | Jackson | |
| 7,578,833 B2 | 8/2009 | Bray | |
| 7,585,312 B2 | 9/2009 | Rawlins et al. | |
| 7,588,575 B2 | 9/2009 | Colleran et al. | |
| 7,588,588 B2 | 9/2009 | Spitler et al. | |
| 7,594,924 B2 | 9/2009 | Albert et al. | |
| 7,597,707 B2 | 10/2009 | Freudiger | |
| 7,601,166 B2 | 10/2009 | Biedermann et al. | |
| 7,608,095 B2 | 10/2009 | Yuan et al. | |
| 7,611,526 B2 | 11/2009 | Carl et al. | |
| 7,615,068 B2 | 11/2009 | Timm et al. | |
| 7,625,394 B2 | 12/2009 | Molz, IV et al. | |
| 7,625,396 B2 | 12/2009 | Jackson | |
| 7,635,379 B2 | 12/2009 | Callahan et al. | |
| 7,648,520 B2 | 1/2010 | Markworth | |
| 7,648,522 B2 | 1/2010 | David | |
| 7,662,172 B2 | 2/2010 | Warnick | |
| 7,662,173 B2 | 2/2010 | Cragg et al. | |
| 7,662,175 B2 | 2/2010 | Jackson | |
| 7,674,293 B2 | 3/2010 | Kuiper et al. | |
| 7,678,136 B2 | 3/2010 | Doubler et al. | |
| 7,678,137 B2 | 3/2010 | Butler et al. | |
| 7,682,377 B2 | 3/2010 | Konieczynski et al. | |
| 7,691,129 B2 | 4/2010 | Felix | |
| 7,691,132 B2 | 4/2010 | Landry et al. | |
| 7,695,498 B2 * | 4/2010 | Ritland | 606/267 |
| 7,699,873 B2 | 4/2010 | Stevenson et al. | |
| 7,699,875 B2 | 4/2010 | Timm et al. | |
| 7,704,270 B2 | 4/2010 | De Coninck | |
| 7,708,762 B2 | 5/2010 | McCarthy et al. | |
| 7,713,287 B2 | 5/2010 | Timm et al. | |
| 7,713,288 B2 | 5/2010 | Timm et al. | |
| 7,717,939 B2 | 5/2010 | Ludwig et al. | |
| 7,722,646 B2 | 5/2010 | Ralph et al. | |
| 7,722,649 B2 | 5/2010 | Biedermann et al. | |
| 7,722,654 B2 | 5/2010 | Taylor et al. | |
| 7,727,259 B2 | 6/2010 | Park | |
| 7,727,261 B2 | 6/2010 | Barker et al. | |
| 7,731,734 B2 | 6/2010 | Clement et al. | |
| 7,731,736 B2 | 6/2010 | Guenther et al. | |
| 7,763,051 B2 | 7/2010 | Labrom et al. | |
| 7,763,052 B2 | 7/2010 | Jahng | |
| 7,766,944 B2 | 8/2010 | Metz-Stavenhagen | |
| 7,766,945 B2 | 8/2010 | Nilsson et al. | |
| 7,776,071 B2 | 8/2010 | Fortin et al. | |
| 7,785,350 B2 | 8/2010 | Eckhardt et al. | |
| 7,785,354 B2 | 8/2010 | Biedermann et al. | |
| 7,789,896 B2 | 9/2010 | Jackson | |
| 7,794,477 B2 | 9/2010 | Melkent et al. | |
| 7,794,481 B2 | 9/2010 | Molz, IV et al. | |
| 7,799,060 B2 | 9/2010 | Lange et al. | |
| 7,803,189 B2 | 9/2010 | Koske | |
| 7,806,913 B2 | 10/2010 | Fanger et al. | |
| 7,806,914 B2 | 10/2010 | Boyd et al. | |
| 7,811,288 B2 | 10/2010 | Jones et al. | |
| 7,811,309 B2 | 10/2010 | Timm et al. | |
| 7,811,311 B2 | 10/2010 | Markworth et al. | |
| 7,815,664 B2 | 10/2010 | Sherman et al. | |
| 7,815,665 B2 | 10/2010 | Jahng et al. | |
| 7,819,899 B2 | 10/2010 | Lancial | |
| 7,819,901 B2 | 10/2010 | Yuan et al. | |
| 7,819,902 B2 | 10/2010 | Abdelgany et al. | |
| 7,828,824 B2 | 11/2010 | Kwak et al. | |
| 7,828,825 B2 | 11/2010 | Bruneau et al. | |
| 7,828,826 B2 | 11/2010 | Drewry et al. | |
| 7,828,830 B2 | 11/2010 | Thramann et al. | |
| 7,833,250 B2 | 11/2010 | Jackson | |
| 7,833,256 B2 | 11/2010 | Biedermann et al. | |
| 7,842,072 B2 | 11/2010 | Dawson | |
| 7,850,715 B2 | 12/2010 | Banouskou et al. | |
| 7,850,718 B2 | 12/2010 | Bette et al. | |
| 7,854,752 B2 | 12/2010 | Colleran et al. | |
| 7,857,833 B2 | 12/2010 | Abdou | |
| 7,857,834 B2 | 12/2010 | Boschert | |
| 7,862,586 B2 | 1/2011 | Malek | |
| 7,862,587 B2 | 1/2011 | Jackson | |
| 7,862,588 B2 | 1/2011 | Abdou | |
| 7,862,591 B2 | 1/2011 | Dewey et al. | |
| 7,862,594 B2 | 1/2011 | Abdelgany et al. | |
| 7,871,413 B2 | 1/2011 | Park et al. | |
| 7,875,059 B2 | 1/2011 | Patterson et al. | |
| 7,875,060 B2 | 1/2011 | Chin | |
| 7,879,074 B2 | 2/2011 | Kwak et al. | |
| 7,892,266 B2 | 2/2011 | Carli | |
| 7,909,856 B2 | 3/2011 | Yuan et al. | |
| 7,914,558 B2 | 3/2011 | Landry et al. | |
| 7,918,792 B2 | 4/2011 | Drzyzga et al. | |
| 7,927,359 B2 | 4/2011 | Trautwein et al. | |
| 7,942,910 B2 | 5/2011 | Doubler et al. | |
| 8,002,807 B2 * | 8/2011 | Abdelgany et al. | 606/264 |
| 8,137,384 B2 * | 3/2012 | Heiges et al. | 606/254 |
| 8,257,397 B2 * | 9/2012 | Winslow et al. | 606/254 |
| 8,292,934 B2 * | 10/2012 | Justis et al. | 606/328 |
| 2003/0004511 A1 | 1/2003 | Ferree | |
| 2003/0163133 A1 * | 8/2003 | Altarac et al. | 606/61 |
| 2003/0171749 A1 | 9/2003 | Le Couedic et al. | |
| 2004/0015166 A1 | 1/2004 | Gorek | |
| 2004/0034374 A1 | 2/2004 | Zatzsch et al. | |
| 2004/0049285 A1 | 3/2004 | Haas | |
| 2004/0097925 A1 | 5/2004 | Boehm, Jr. et al. | |
| 2004/0111088 A1 | 6/2004 | Picetti et al. | |
| 2004/0122425 A1 | 6/2004 | Suzuki et al. | |
| 2004/0147928 A1 | 7/2004 | Landry et al. | |
| 2004/0153077 A1 | 8/2004 | Biedermann et al. | |

| | | | | | | |
|---|---|---|---|---|---|---|
| 2004/0158247 A1 | 8/2004 | Sitiso et al. | | 2006/0247631 A1 | 11/2006 | Ahn et al. |
| 2004/0162560 A1 | 8/2004 | Raynor et al. | | 2006/0247637 A1 | 11/2006 | Colleran et al. |
| 2004/0172022 A1 | 9/2004 | Landry et al. | | 2006/0253118 A1 | 11/2006 | Bailey |
| 2004/0172024 A1 | 9/2004 | Gorek | | 2006/0264935 A1 | 11/2006 | White |
| 2004/0215192 A1 | 10/2004 | Justis et al. | | 2006/0264937 A1 | 11/2006 | White |
| 2004/0225289 A1 | 11/2004 | Biedermann et al. | | 2006/0276897 A1 | 12/2006 | Winslow et al. |
| 2004/0230192 A1 | 11/2004 | Graf | | 2006/0282073 A1 | 12/2006 | Simanovsky |
| 2004/0230304 A1 | 11/2004 | Yuan et al. | | 2006/0282078 A1 | 12/2006 | Labrom et al. |
| 2005/0049589 A1 | 3/2005 | Jackson | | 2007/0016190 A1 | 1/2007 | Martinez et al. |
| 2005/0080415 A1 | 4/2005 | Keyer et al. | | 2007/0016194 A1 | 1/2007 | Shaolian et al. |
| 2005/0090822 A1 | 4/2005 | DiPoto | | 2007/0016201 A1 | 1/2007 | Freudiger |
| 2005/0096652 A1 | 5/2005 | Burton | | 2007/0049936 A1 | 3/2007 | Colleran et al. |
| 2005/0107788 A1 | 5/2005 | Beaurain et al. | | 2007/0083200 A1 | 4/2007 | Gittings et al. |
| 2005/0113923 A1 | 5/2005 | Acker et al. | | 2007/0088359 A1 | 4/2007 | Woods et al. |
| 2005/0131404 A1 | 6/2005 | Mazda et al. | | 2007/0093814 A1 | 4/2007 | Callahan, II et al. |
| 2005/0131406 A1 | 6/2005 | Reiley et al. | | 2007/0093820 A1 | 4/2007 | Freudiger |
| 2005/0143737 A1 | 6/2005 | Pafford et al. | | 2007/0093821 A1 | 4/2007 | Freudiger |
| 2005/0171537 A1 | 8/2005 | Mazel et al. | | 2007/0118122 A1 | 5/2007 | Butler et al. |
| 2005/0171543 A1 | 8/2005 | Timm et al. | | 2007/0123871 A1 | 5/2007 | Jahng |
| 2005/0177156 A1 | 8/2005 | Timm et al. | | 2007/0161994 A1 | 7/2007 | Lowery et al. |
| 2005/0177157 A1 | 8/2005 | Jahng | | 2007/0162007 A1 | 7/2007 | Shoham |
| 2005/0177164 A1 | 8/2005 | Walters et al. | | 2007/0167946 A1 | 7/2007 | Triplett et al. |
| 2005/0182400 A1 | 8/2005 | White | | 2007/0167947 A1 | 7/2007 | Gittings |
| 2005/0182401 A1 | 8/2005 | Timm et al. | | 2007/0198014 A1 | 8/2007 | Graf et al. |
| 2005/0192569 A1 | 9/2005 | Nichols et al. | | 2007/0213719 A1 | 9/2007 | Hudgins et al. |
| 2005/0228382 A1 | 10/2005 | Richelsoph et al. | | 2007/0233068 A1 | 10/2007 | Bruneau et al. |
| 2005/0228385 A1 | 10/2005 | Iott et al. | | 2007/0233072 A1 | 10/2007 | Dickinson et al. |
| 2005/0240180 A1 | 10/2005 | Vienney et al. | | 2007/0233090 A1 | 10/2007 | Naifeh et al. |
| 2005/0240265 A1 | 10/2005 | Kuiper et al. | | 2007/0233091 A1 | 10/2007 | Naifeh et al. |
| 2005/0261770 A1 | 11/2005 | Kuiper et al. | | 2007/0233092 A1 | 10/2007 | Falahee |
| 2005/0267470 A1 | 12/2005 | McBride | | 2007/0233093 A1 | 10/2007 | Falahee |
| 2005/0277922 A1 | 12/2005 | Trieu et al. | | 2007/0233094 A1 | 10/2007 | Colleran et al. |
| 2005/0288670 A1 | 12/2005 | Panjabi et al. | | 2007/0250061 A1 | 10/2007 | Chin et al. |
| 2006/0025771 A1 | 2/2006 | Jackson | | 2007/0270836 A1 | 11/2007 | Bruneau et al. |
| 2006/0036324 A1 | 2/2006 | Sachs et al. | | 2007/0270838 A1 | 11/2007 | Bruneau et al. |
| 2006/0052783 A1 | 3/2006 | Dant et al. | | 2007/0276380 A1 | 11/2007 | Jahng et al. |
| 2006/0052784 A1 | 3/2006 | Dant et al. | | 2007/0288009 A1 | 12/2007 | Brown et al. |
| 2006/0052786 A1 | 3/2006 | Dant et al. | | 2007/0288012 A1 | 12/2007 | Colleran et al. |
| 2006/0058787 A1 | 3/2006 | David | | 2008/0009864 A1 | 1/2008 | Forton et al. |
| 2006/0058788 A1 | 3/2006 | Hammer et al. | | 2008/0021459 A1 | 1/2008 | Lim |
| 2006/0079894 A1 | 4/2006 | Colleran et al. | | 2008/0021461 A1 | 1/2008 | Barker et al. |
| 2006/0079896 A1 | 4/2006 | Kwak et al. | | 2008/0033433 A1 | 2/2008 | Implicito |
| 2006/0084978 A1 | 4/2006 | Mokhtar | | 2008/0039838 A1 | 2/2008 | Landry et al. |
| 2006/0084982 A1 | 4/2006 | Kim | | 2008/0051787 A1 | 2/2008 | Remington et al. |
| 2006/0084983 A1 | 4/2006 | Kim | | 2008/0065073 A1 | 3/2008 | Perriello et al. |
| 2006/0084984 A1 | 4/2006 | Kim | | 2008/0065075 A1 | 3/2008 | Dant et al. |
| 2006/0084985 A1 | 4/2006 | Kim | | 2008/0065079 A1 | 3/2008 | Bruneau et al. |
| 2006/0084987 A1 | 4/2006 | Kim | | 2008/0071273 A1 | 3/2008 | Hawkes et al. |
| 2006/0084988 A1 | 4/2006 | Kim | | 2008/0077139 A1 | 3/2008 | Landry et al. |
| 2006/0084989 A1 | 4/2006 | Dickinson et al. | | 2008/0183215 A1 | 7/2008 | Altarac et al. |
| 2006/0084990 A1 | 4/2006 | Gournay et al. | | 2008/0195208 A1 | 8/2008 | Castellvi et al. |
| 2006/0085069 A1 | 4/2006 | Kim | | 2008/0262554 A1 | 10/2008 | Hayes et al. |
| 2006/0085070 A1 | 4/2006 | Kim | | 2008/0312693 A1 | 12/2008 | Trautwein et al. |
| 2006/0089643 A1 | 4/2006 | Mujwid | | 2009/0062868 A1 | 3/2009 | Casutt |
| 2006/0095035 A1 | 5/2006 | Jones et al. | | 2010/0174317 A1 | 7/2010 | Timm et al. |
| 2006/0106383 A1 | 5/2006 | Biedermann et al. | | 2010/0198270 A1 | 8/2010 | Barker et al. |
| 2006/0111712 A1 | 5/2006 | Jackson | | 2010/0222819 A1 | 9/2010 | Timm et al. |
| 2006/0122620 A1 | 6/2006 | Kim | | | | |
| 2006/0129148 A1 | 6/2006 | Simmons et al. | | FOREIGN PATENT DOCUMENTS | | |
| 2006/0129149 A1 | 6/2006 | Iott et al. | | | | |
| 2006/0142761 A1 | 6/2006 | Landry et al. | | EP | 0128058 B1 | 4/1988 |
| 2006/0149242 A1 | 7/2006 | Kraus et al. | | EP | 0669109 B1 | 8/1995 |
| 2006/0149244 A1 | 7/2006 | Amrein et al. | | EP | 0982007 | 3/2000 |
| 2006/0149380 A1 | 7/2006 | Lotz et al. | | EP | 1281362 A2 | 2/2003 |
| 2006/0161153 A1 | 7/2006 | Hawkes et al. | | EP | 1330987 A1 | 7/2003 |
| 2006/0195093 A1 | 8/2006 | Jahng | | FR | 2612070 A1 | 9/1988 |
| 2006/0200128 A1 | 9/2006 | Mueller | | FR | 2615095 A1 | 11/1988 |
| 2006/0200131 A1 | 9/2006 | Chao et al. | | FR | 2844180 A1 | 3/2004 |
| 2006/0229607 A1 | 10/2006 | Brumfield | | FR | 2880256 B1 | 7/2006 |
| 2006/0229613 A1 | 10/2006 | Timm et al. | | GB | 780652 | 8/1957 |
| 2006/0235385 A1 | 10/2006 | Whipple | | GB | 2173104 | 10/1986 |
| 2006/0235389 A1 | 10/2006 | Albert et al. | | GB | 2382304 | 5/2003 |
| 2006/0235392 A1 | 10/2006 | Hammer et al. | | KR | 20080072848 | 8/2008 |
| 2006/0235393 A1 | 10/2006 | Bono et al. | | WO | WO 87/07134 | 12/1987 |
| 2006/0241600 A1 | 10/2006 | Ensign et al. | | WO | WO 94/21185 | 9/1994 |
| 2006/0241601 A1 | 10/2006 | Trautwein et al. | | WO | WO 98/27884 | 7/1998 |
| 2006/0241603 A1 | 10/2006 | Jackson | | WO | WO 01/45576 | 6/2001 |
| 2006/0241757 A1 | 10/2006 | Anderson | | WO | WO 01/91656 | 12/2001 |
| 2006/0247623 A1 | 11/2006 | Anderson et al. | | WO | WO 02/07621 | 1/2002 |
| | | | | WO | WO 02/07622 | 1/2002 |

| | | |
|---|---|---|
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO 2004/024011 | 3/2004 |
| WO | WO 2004/034916 | 4/2004 |
| WO | WO 2006/033503 | 3/2006 |
| WO | WO 2006/066685 | 6/2006 |
| WO | WO 2006/105935 | 10/2006 |
| WO | WO 2007/064324 | 6/2007 |
| WO | WO 2007/080317 | 7/2007 |
| WO | WO 2008/034130 | 3/2008 |
| WO | WO 2008/073544 | 6/2008 |

OTHER PUBLICATIONS

Zimmer, Inc. Website, 2007; Zimmer Spine, product description for Dynesis—The Dynamic Stabilization System, 5 pages, <http://www.zimmer.com/ctl?template=IN&action=1&op=global&id=9165&pr=Y>.

Ito Medical Instrument website, 2006; ITOIKA Medical Instruments, product description for S-Plate, 15 pages, <http://ito-ika.co.jp/s-plate/splate1.pdf and http://ito-ika.co.jp/s-plate/splate1.pdf>.

"Flexible rods and the case for dynamic stabilization," Jason M. Highsmith, M.D., et al., Neurosurg. Focus, vol. 22, Jan. 2007, pp. 1-5.

"The Spinous Process: The Forgotten Appendage," Kenneth R. Kattan, M. D. eta l., Skeletal Radiology, vol. 6, 1981, pp. 199-204.

"Morphological and functional changes of the lumbar spinous processes in the elderly," R. Scapinelli, Surgical Radiologic Anatomy, vol. 11, 1989, pp. 129-133.

"The Paraspinal Sacrospinalis-Splitting Approach to the Lumbar Spine," Leon L. Wiltse et al., The Journal of Bone & Joint Surgery, vol. 50-A, No. 5, Jul. 1968 pp. 919-926.

Dynamic Reconstruction of the Spine, D.H. Kim et al., Thieme, New York 2006, Chapters 1, 2, 30, 31, 37-43.

International Search Report for PCT/US07/70981 dated Apr. 23, 2008, 7 pages.

International Search Report for PCT/US/2009/058466 dated Apr. 29, 2010, 13 pages.

International Search Report for PCT/US/2009/058460 dated Apr. 29, 2010, 11 pages.

International Search Report for PCT/US/2009/058470 dated Apr. 29, 2010, 12 pages.

International Search Report for PCT/US/2009/066567 dated Jul. 20, 2010, 9 pages.

International Search Report for PCT/US2010/058776 dated Aug. 23, 2011, 4 pages.

International Search Report dated May 8, 2012 for Application No. PCT/US2011/057403, 17 pages.

* cited by examiner

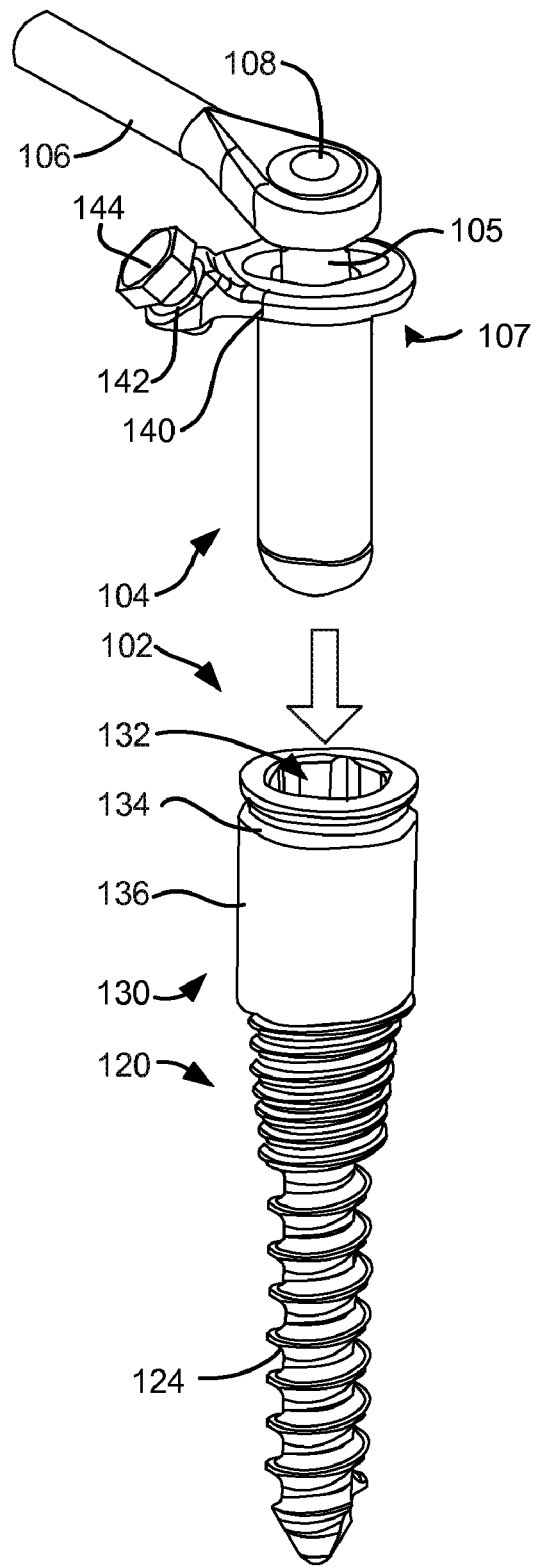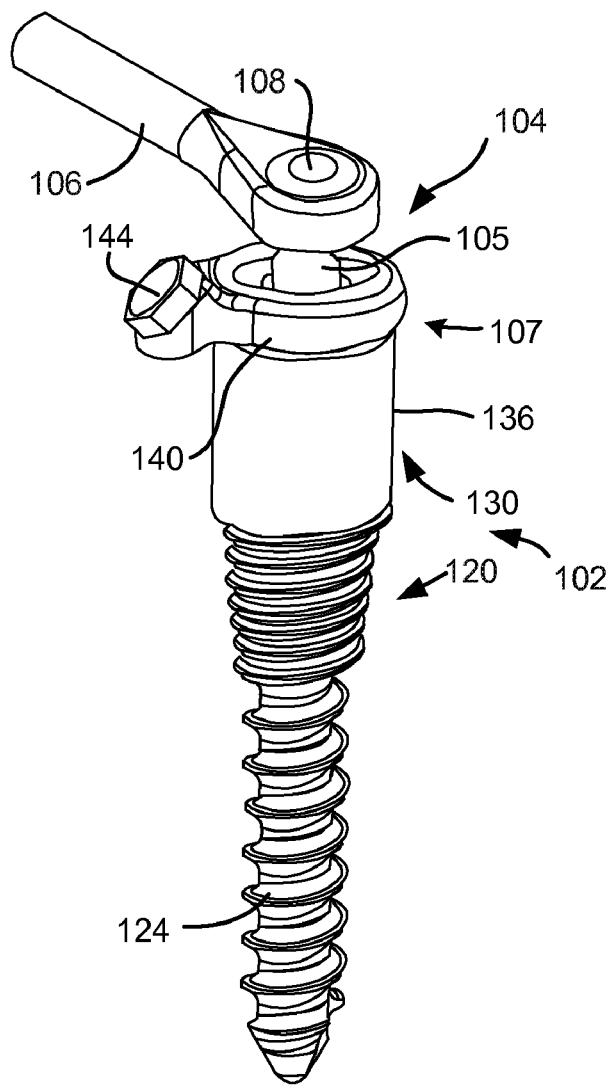
FIG. 1A  FIG. 1B

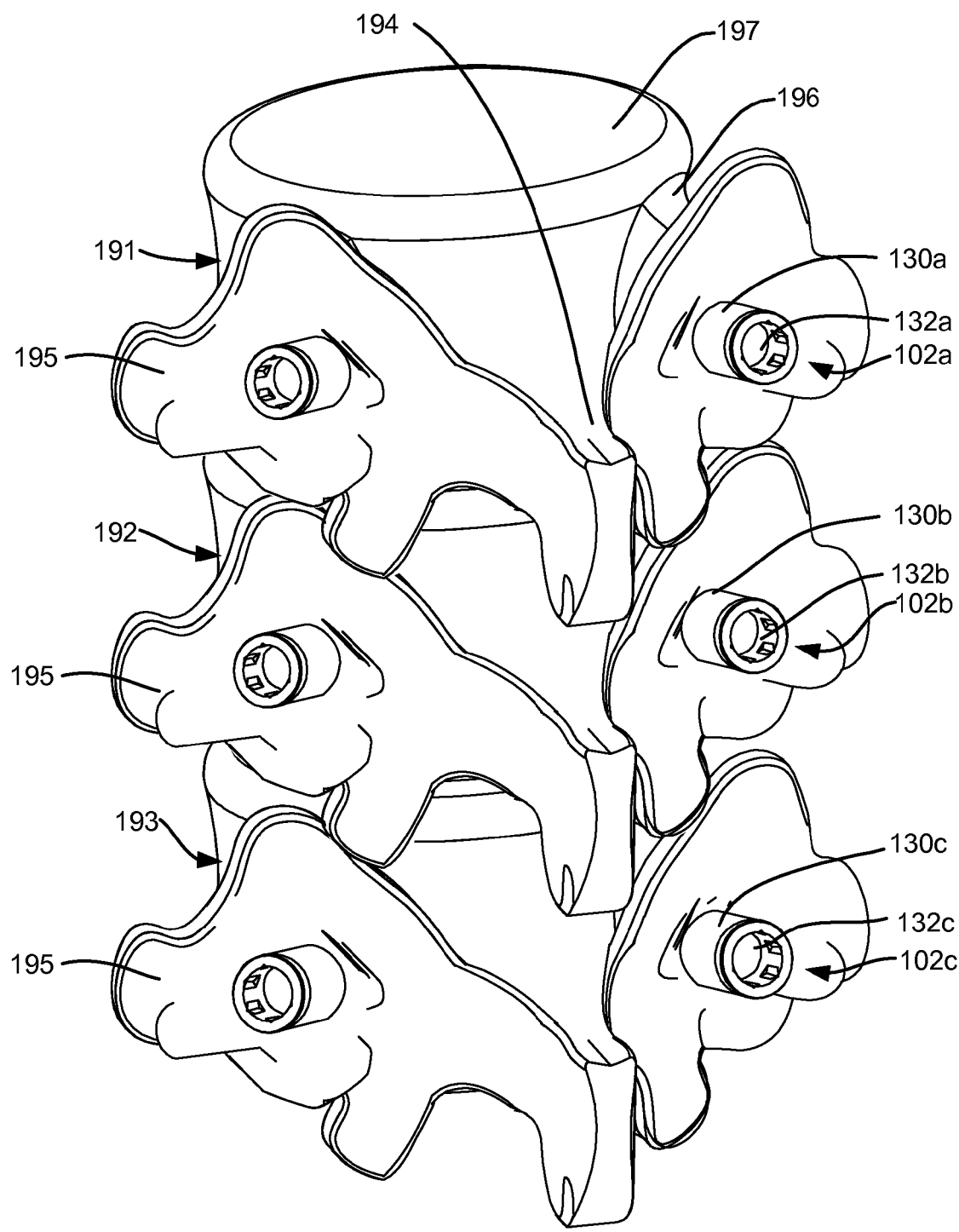

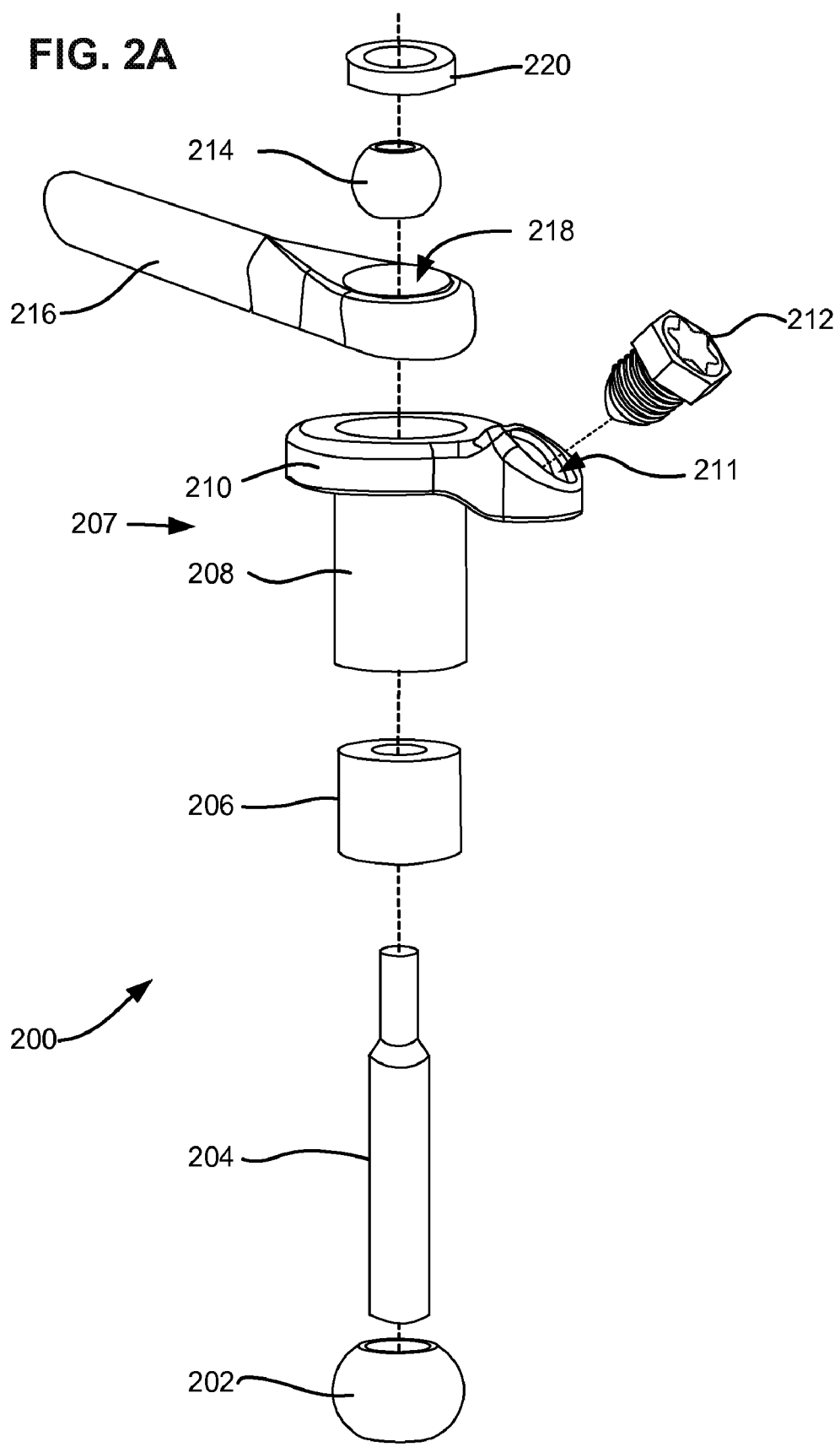

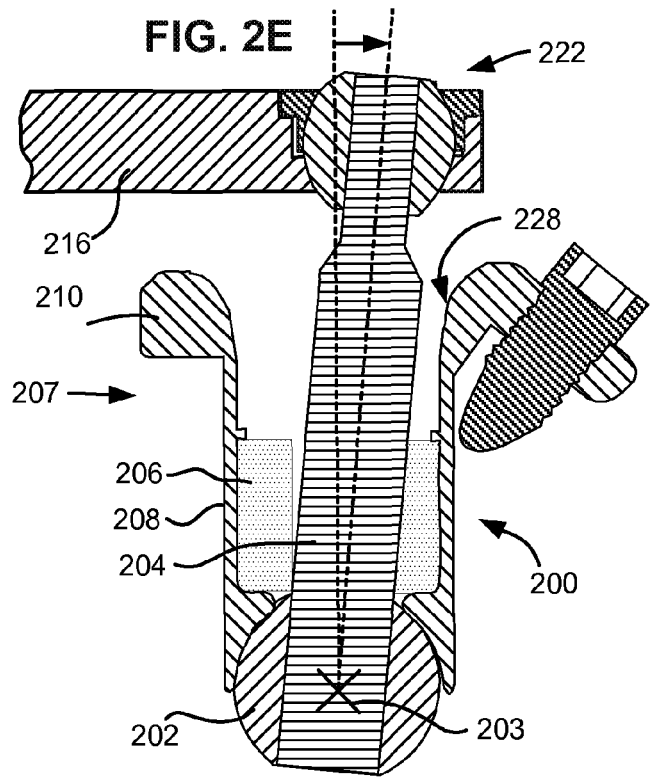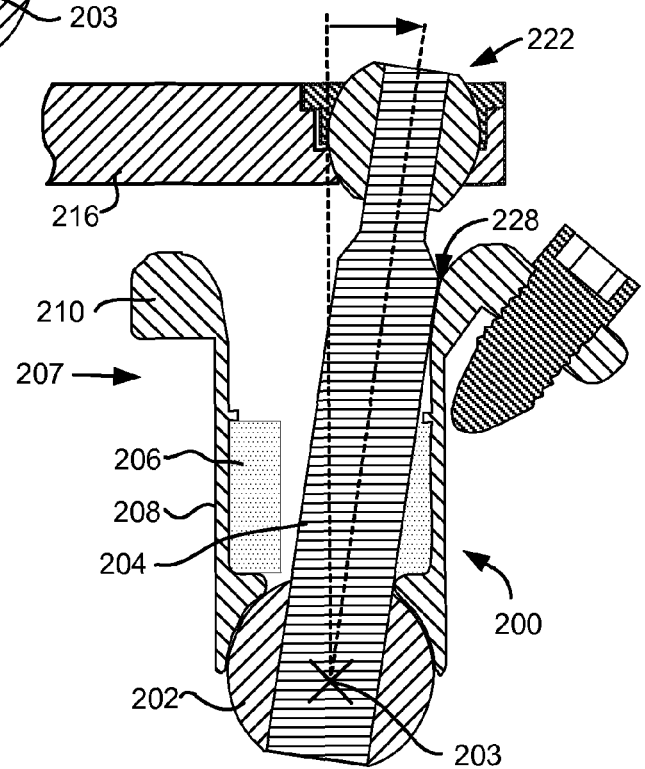

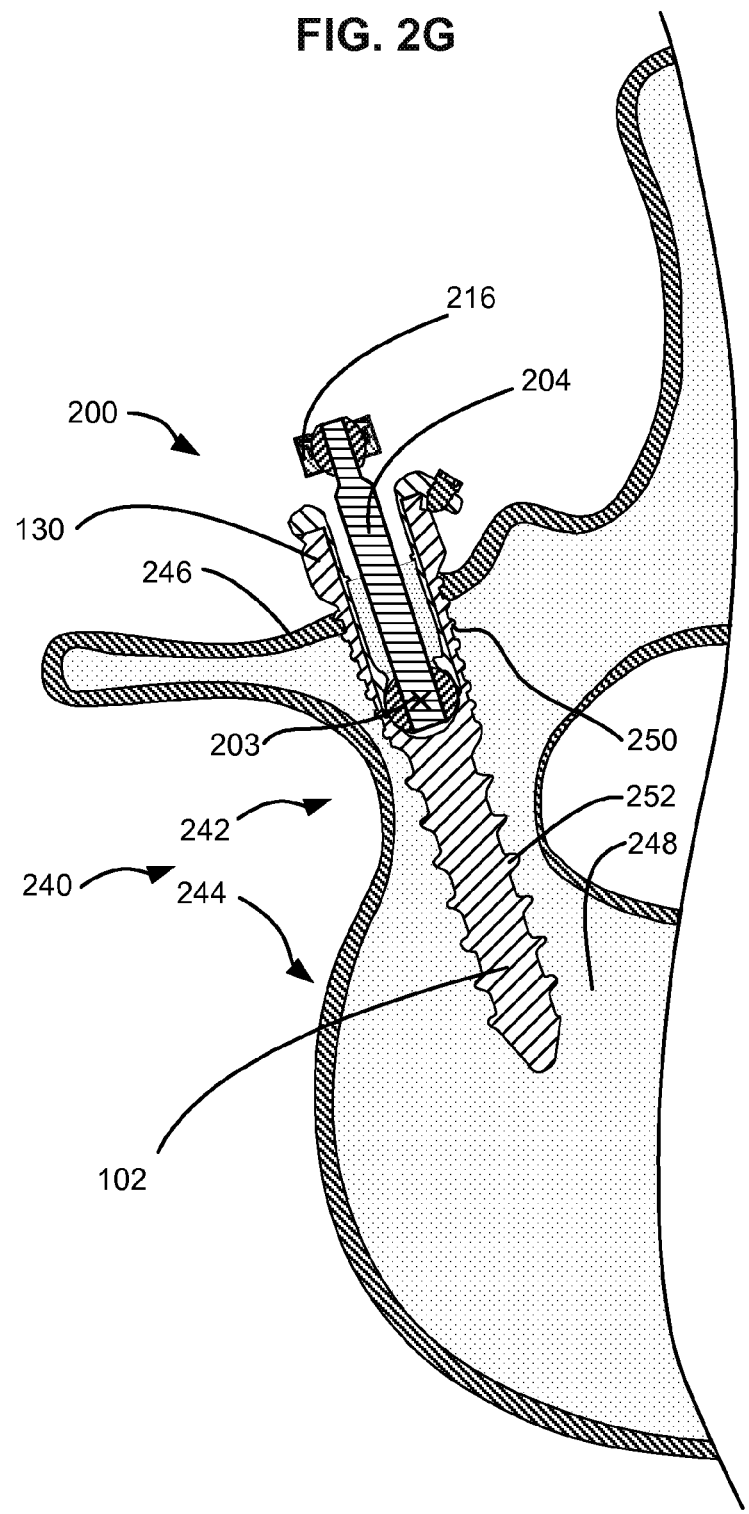

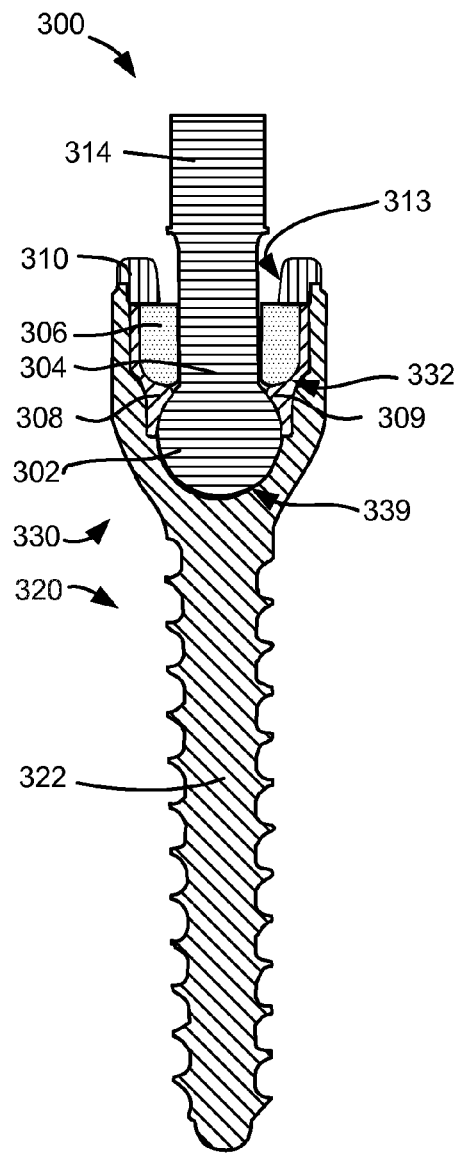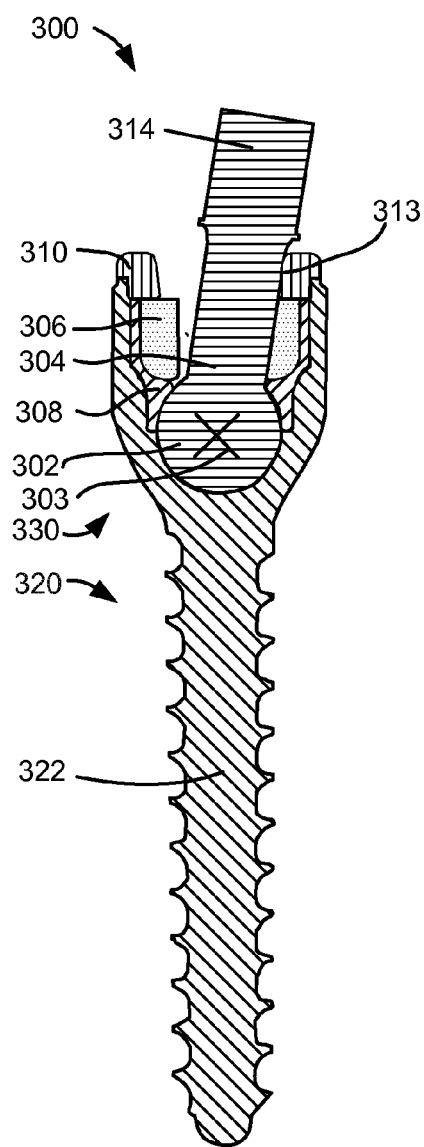

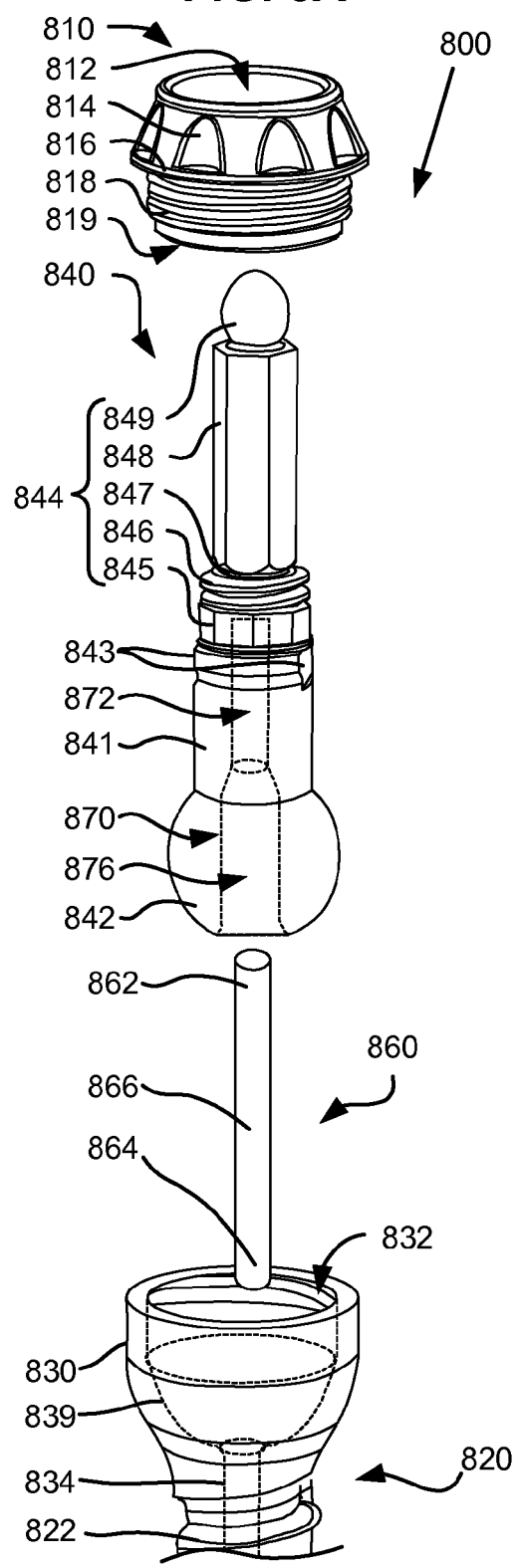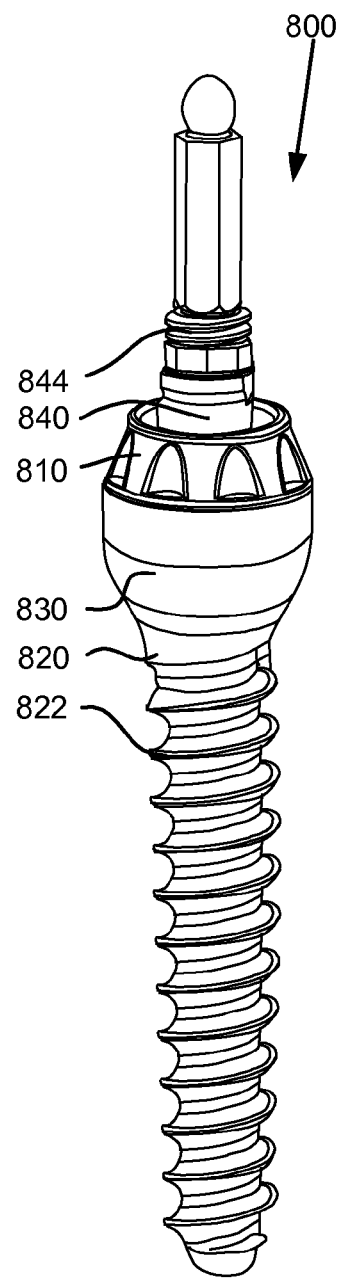

FIG. 8C
FIG. 8D
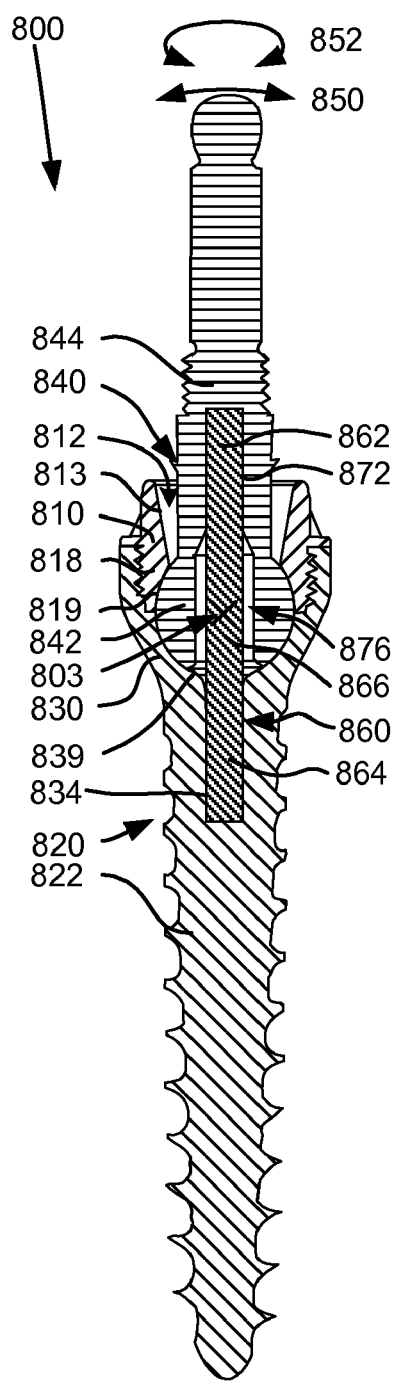
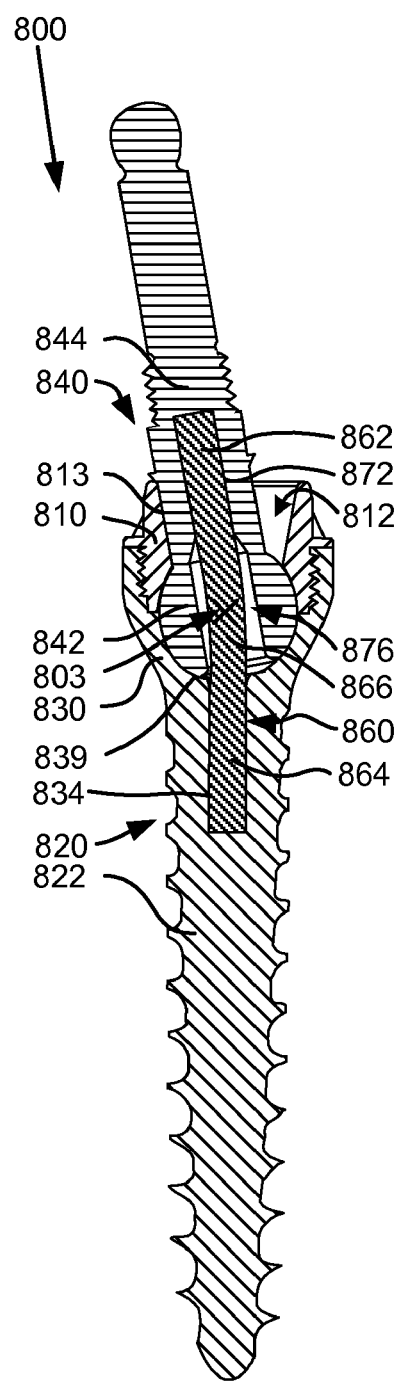

FIG. 8E
FIG. 8F
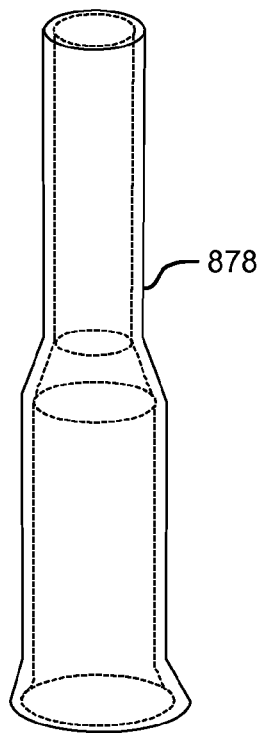
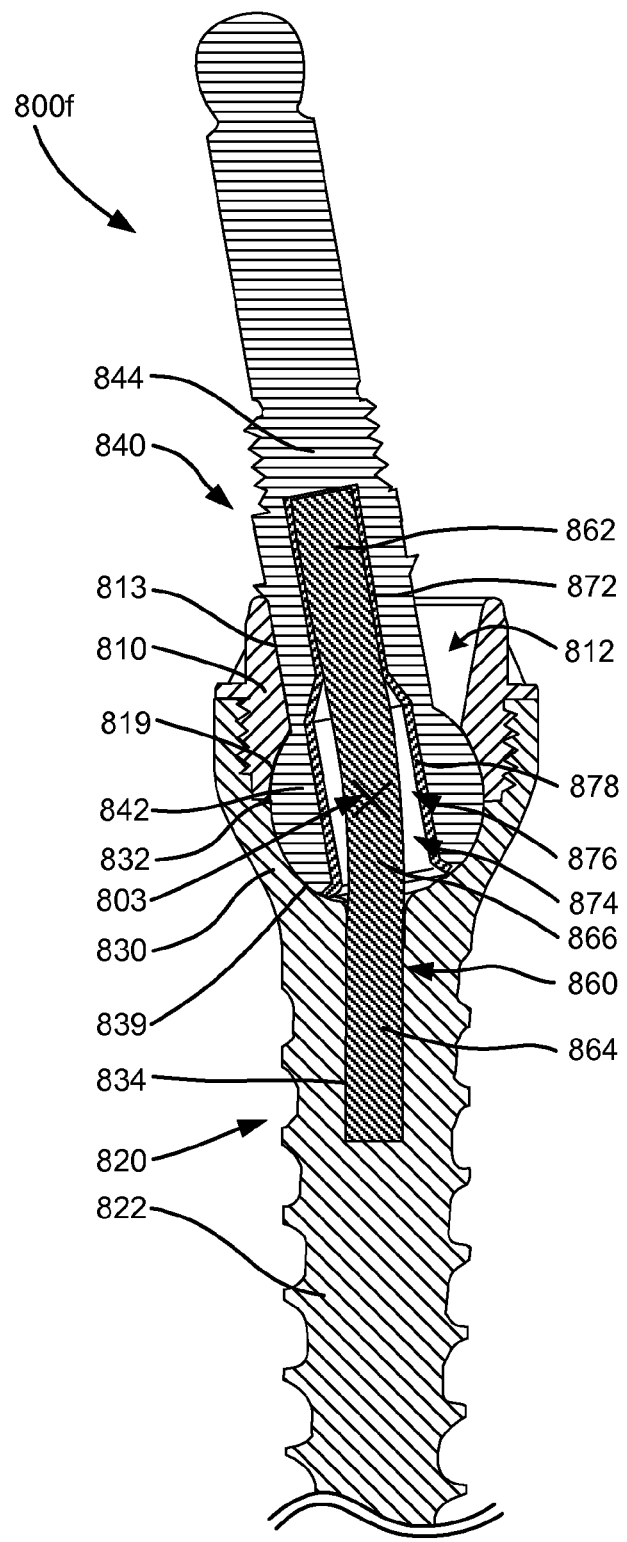

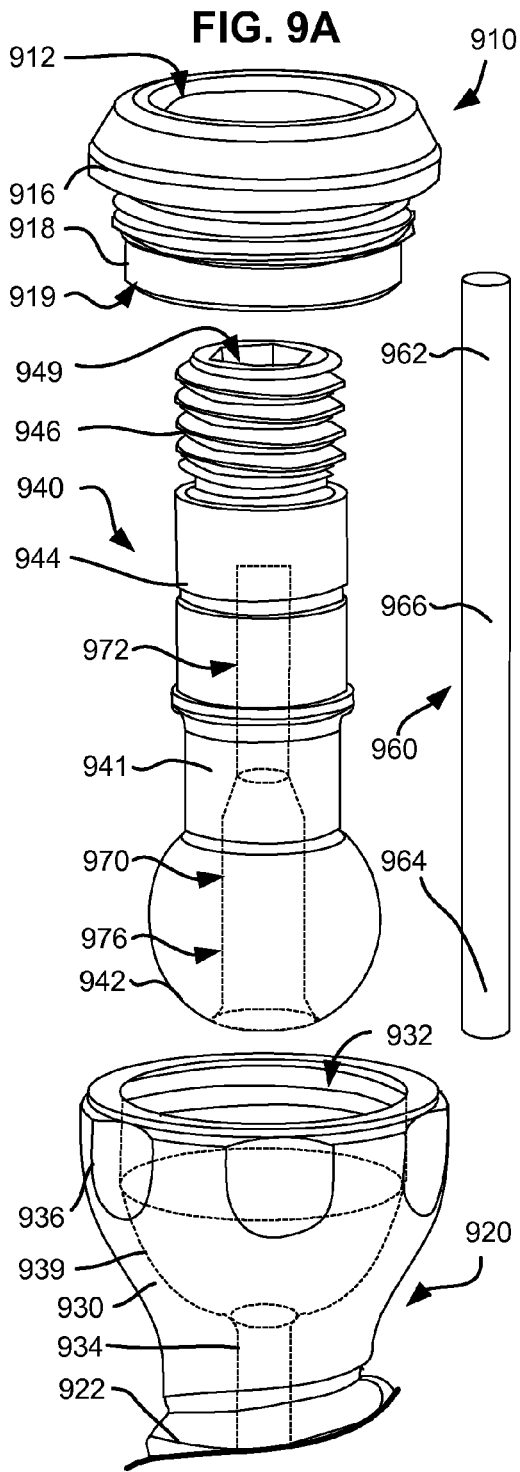
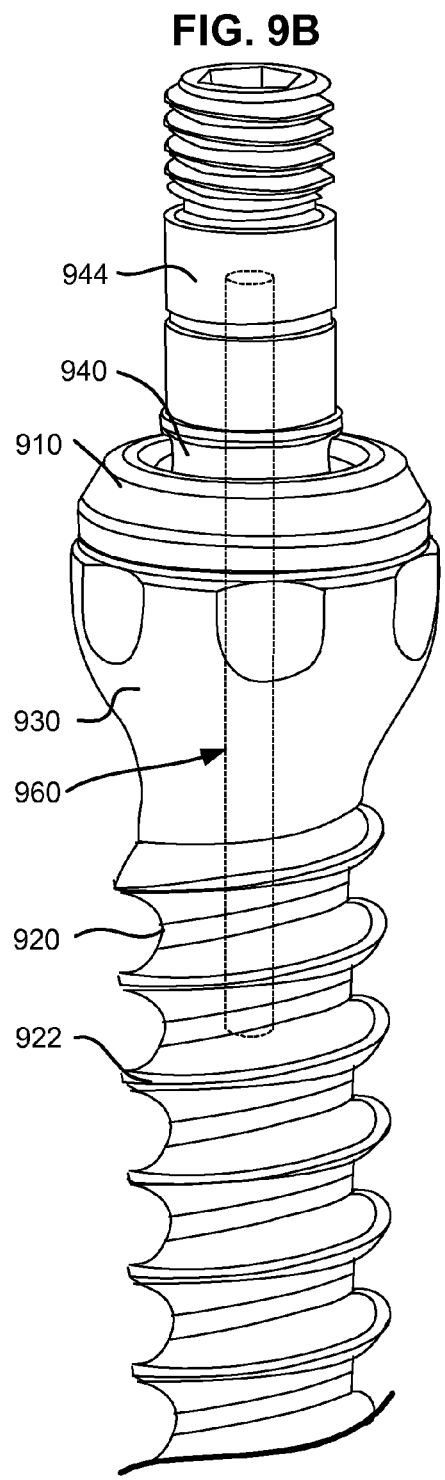

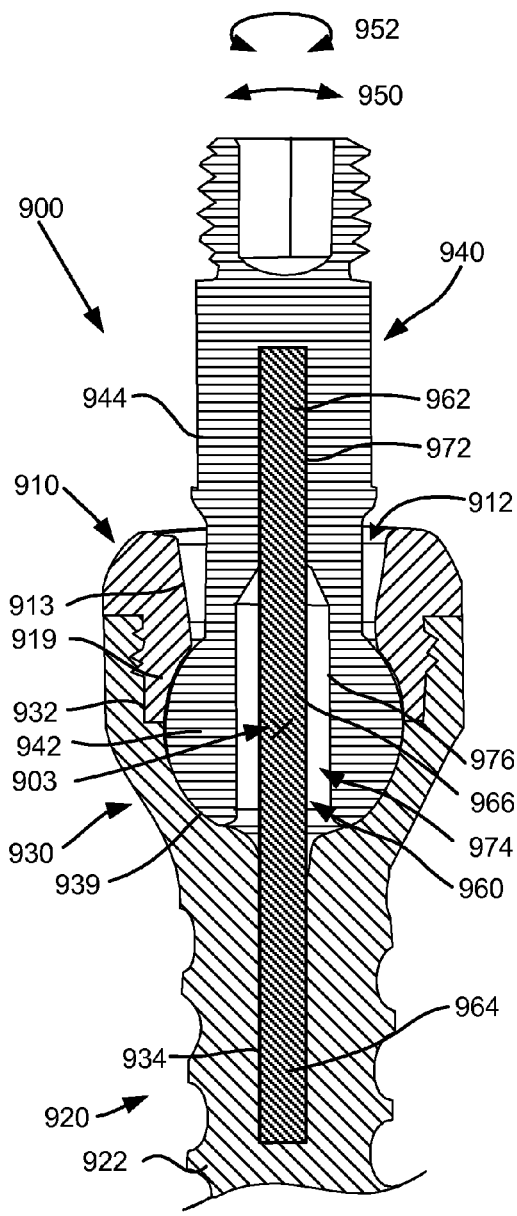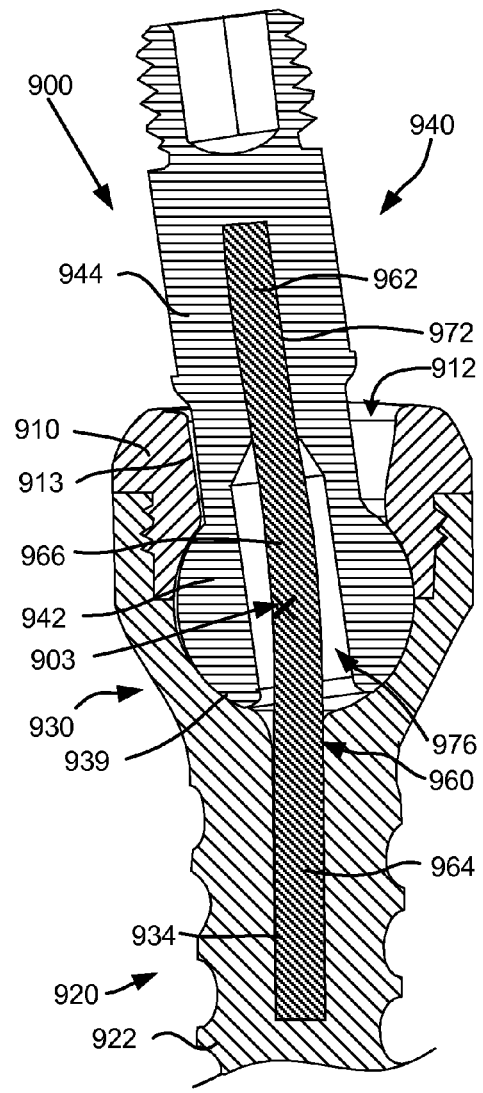
FIG. 9C
FIG. 9D

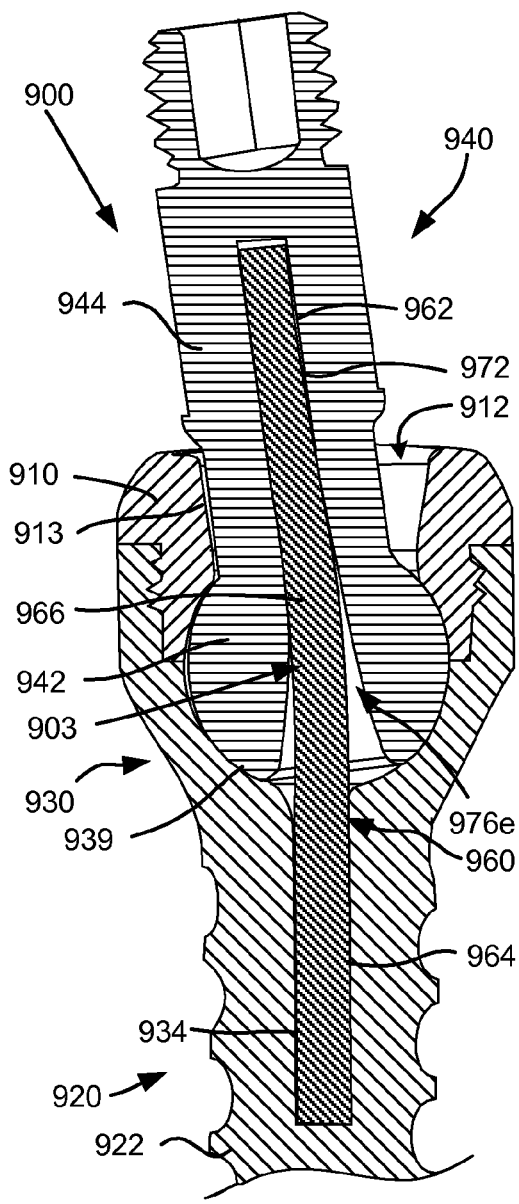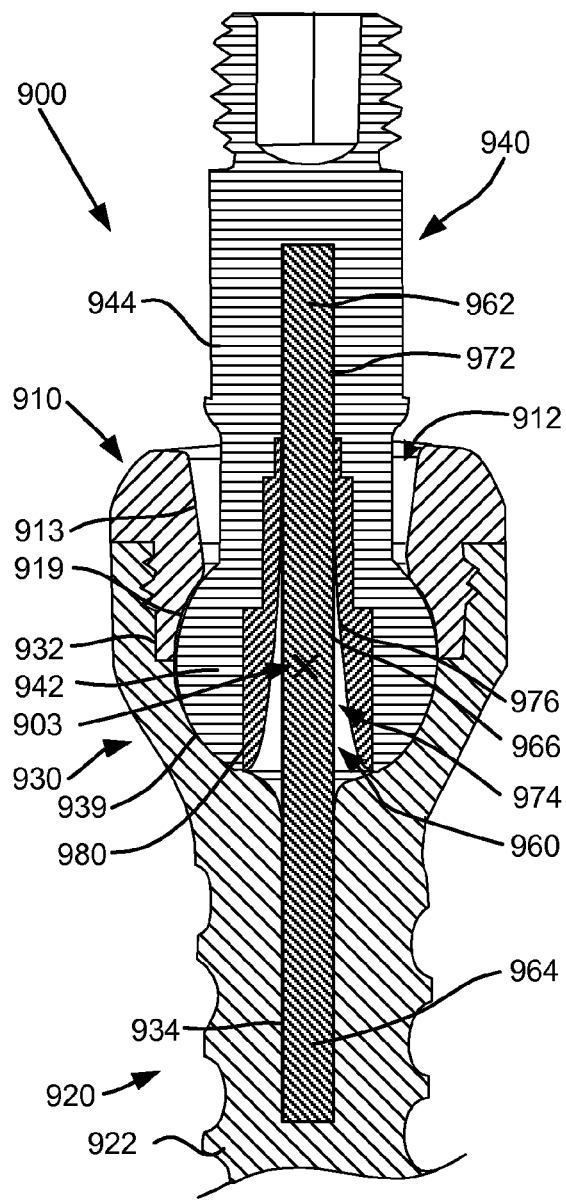

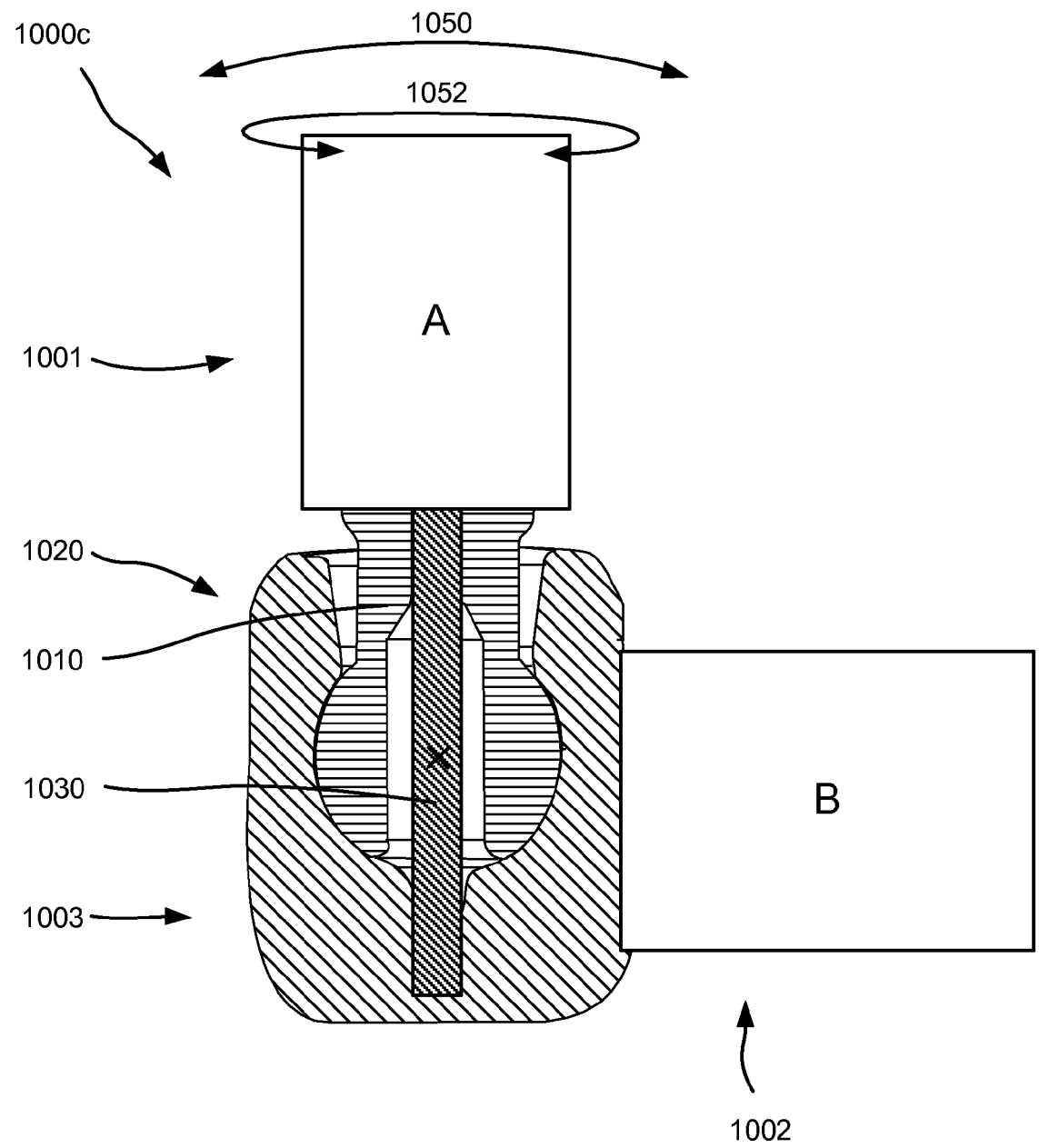

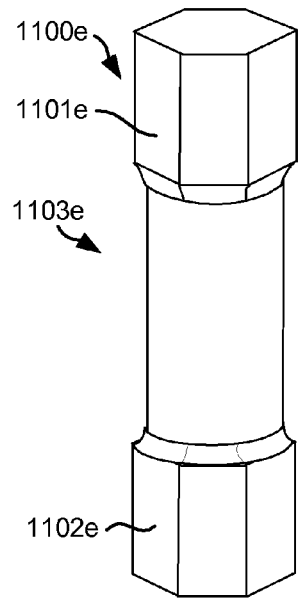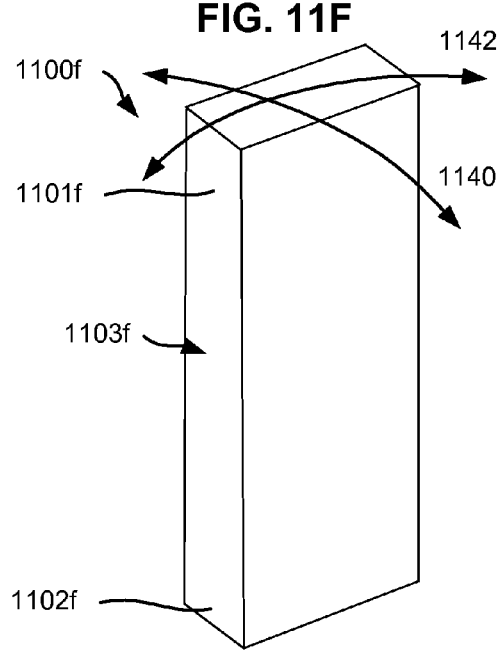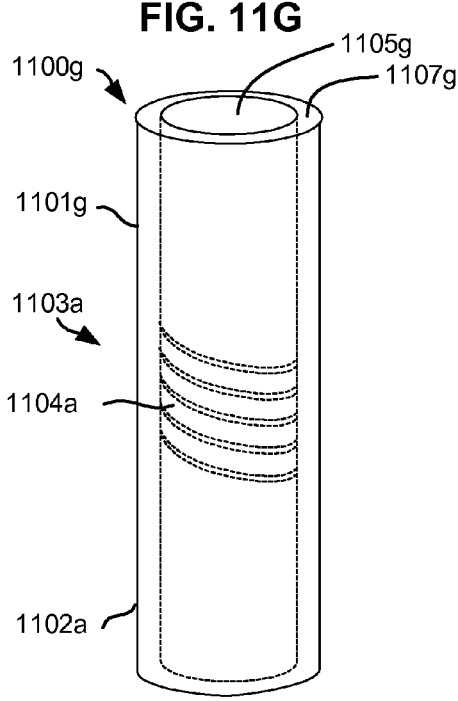

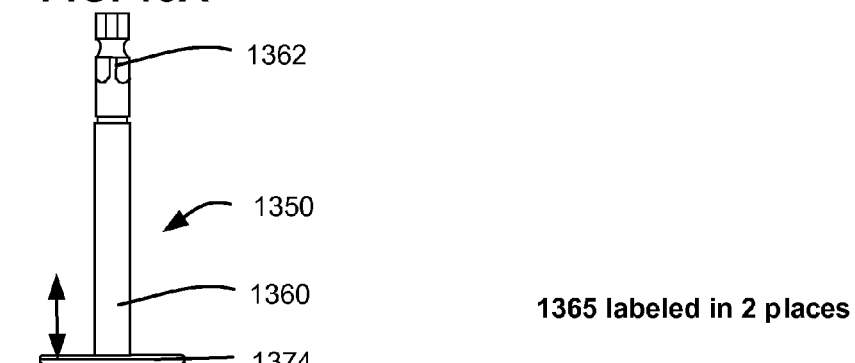
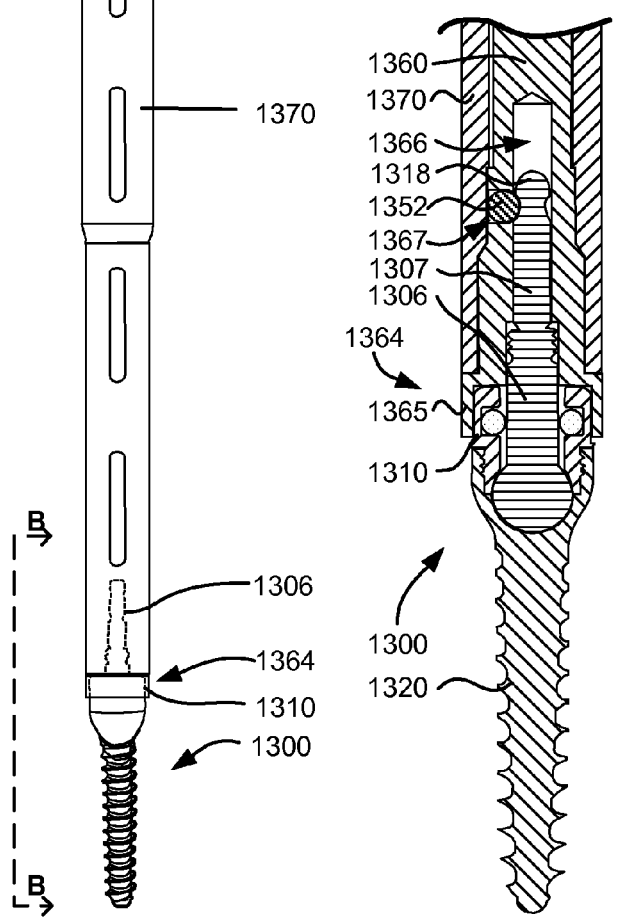
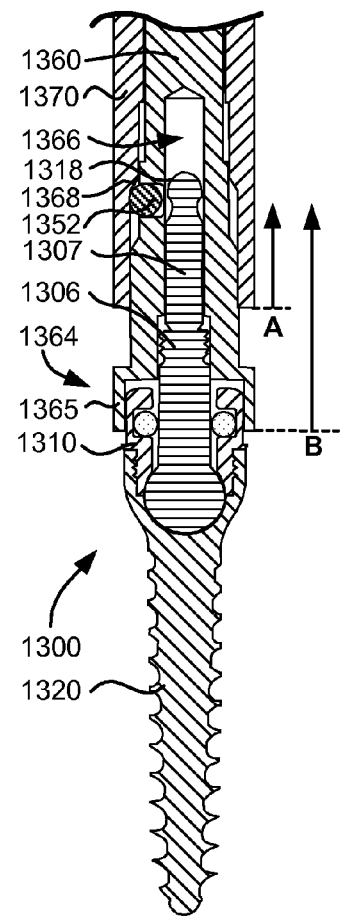

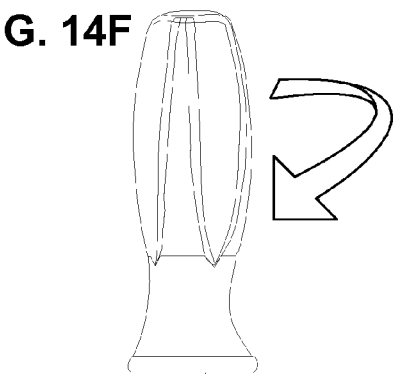
FIG. 14F
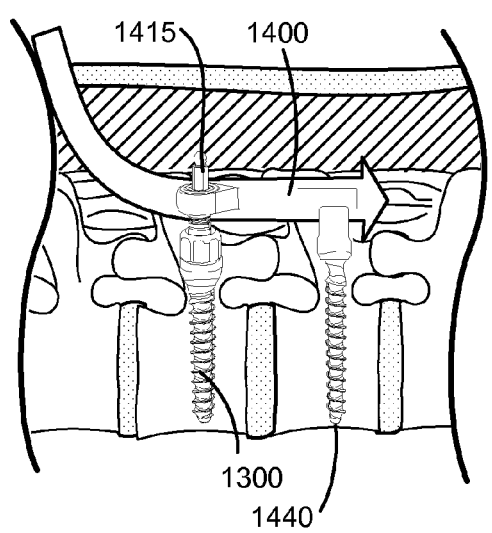
FIG. 14E
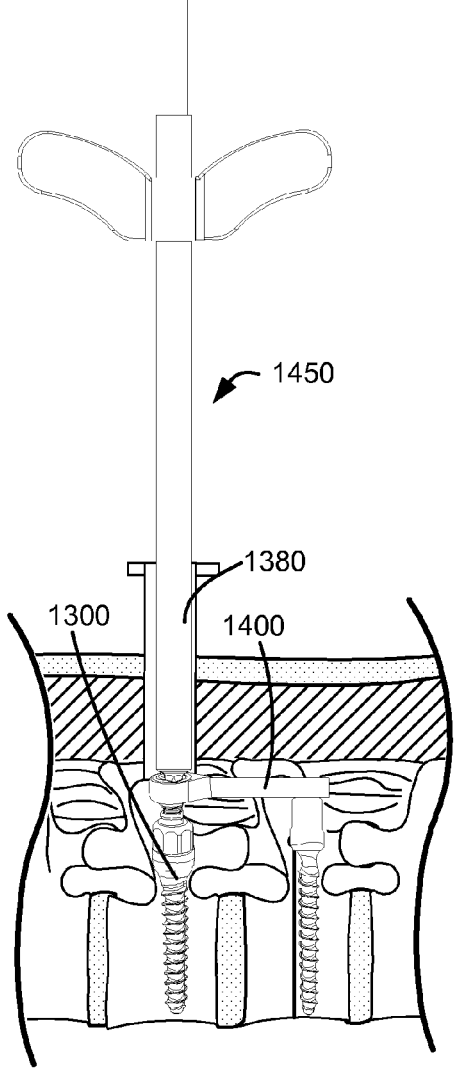

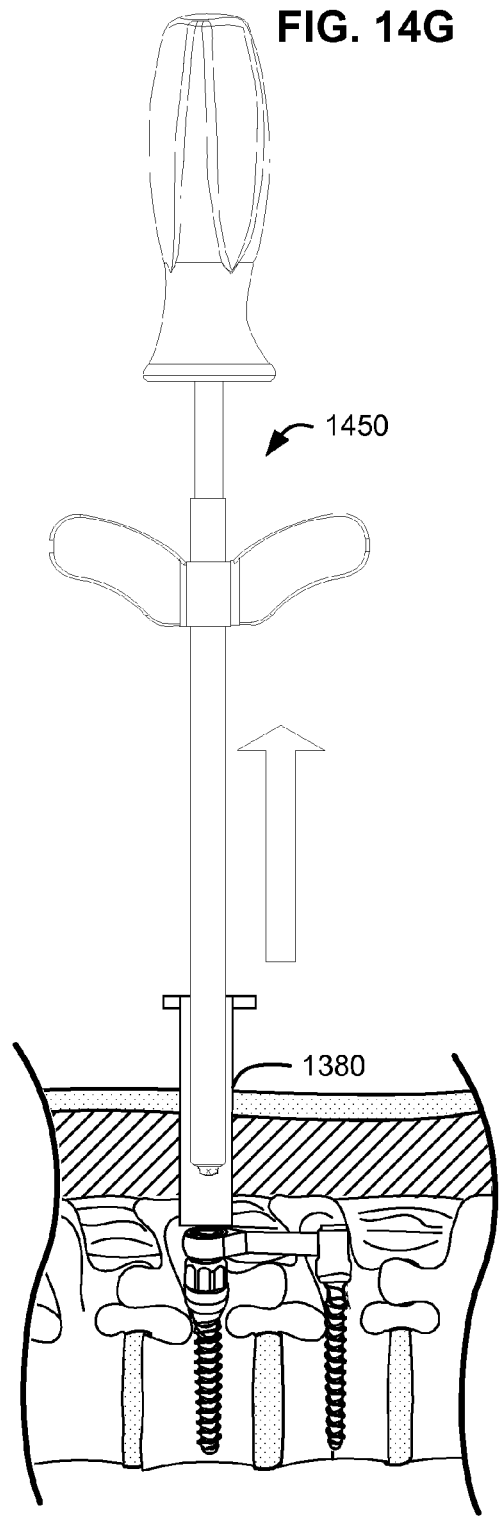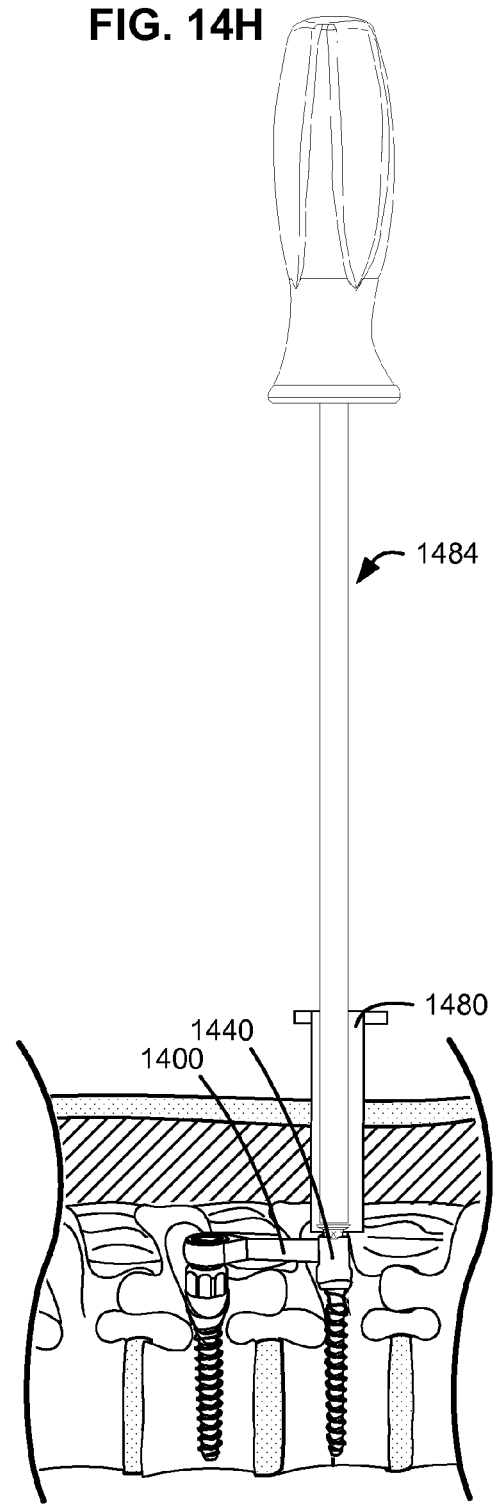

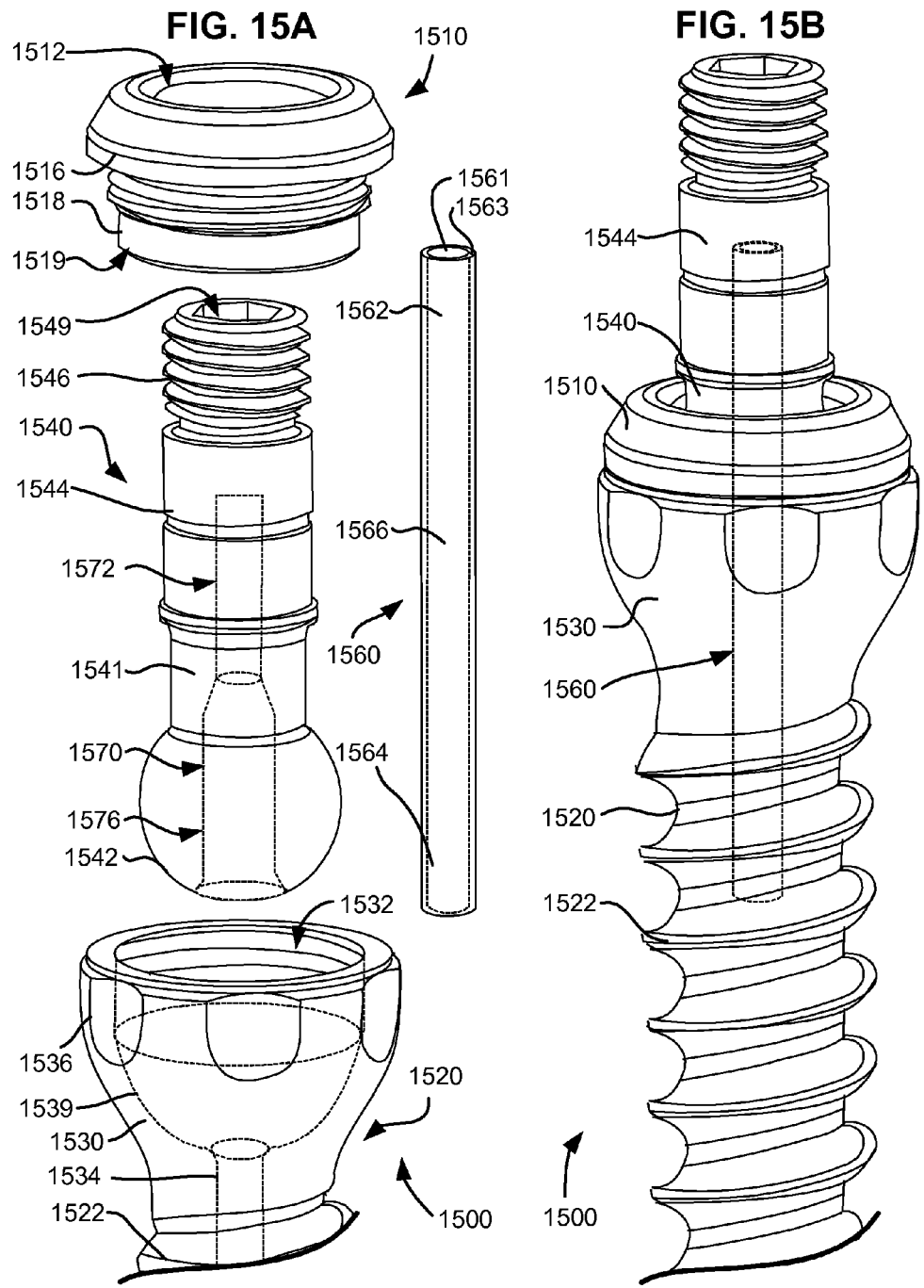

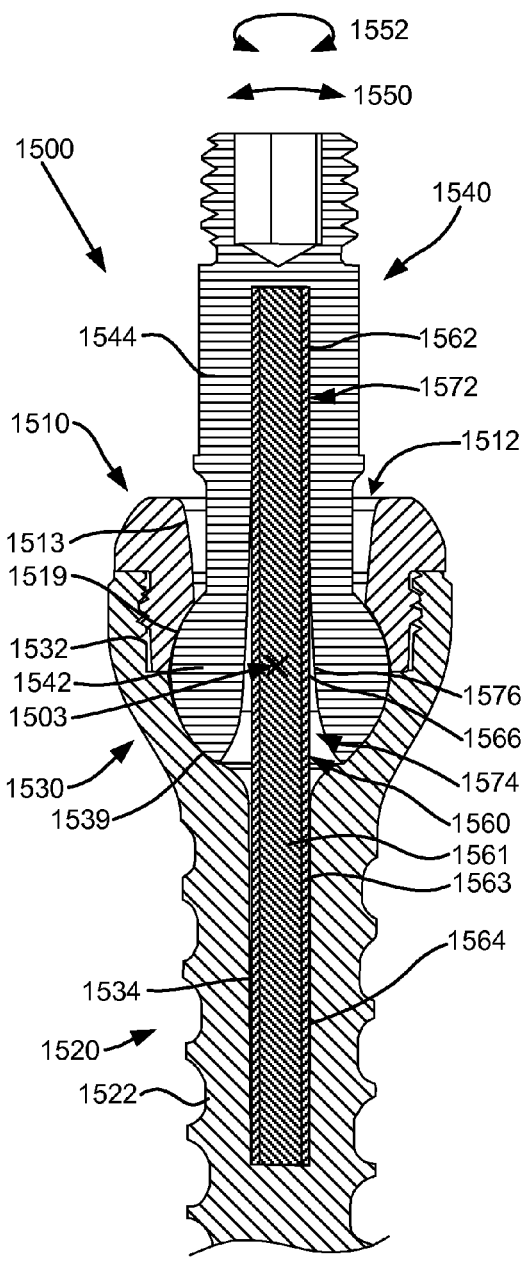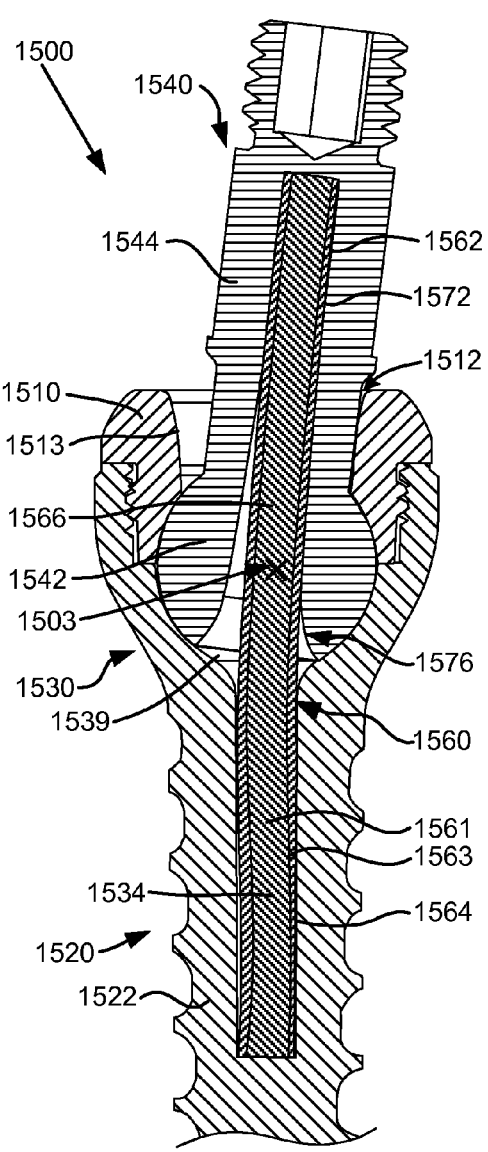

LOW PROFILE SPINAL PROSTHESIS INCORPORATING A BONE ANCHOR HAVING A DEFLECTABLE POST AND A COMPOUND SPINAL ROD

CLAIM TO PRIORITY

This patent application claims priority to the following patents and patent applications:

U.S. patent application Ser. No. 12/629,811, filed Dec. 2, 2009, entitled "Low Profile Spinal Prosthesis Incorporating A Bone Anchor Having A Deflectable Post And A Compound Spinal Rod"; and International Patent Application No. PCT/US2009/066567, filed Dec. 3, 3009, entitled "Low Profile Spinal Prosthesis Incorporating A Bone Anchor Having A Deflectable Post And A Compound Spinal Rod"; and U.S. patent application Ser. No. 12/959,200, filed Dec. 2, 2010, entitled "Low Profile Spinal Prosthesis Incorporating A Bone Anchor Having A Deflectable Post And A Compound Spinal Rod"; and International Application No. PCT/US/2010/058776, filed Dec. 2, 2010, entitled "Low Profile Spinal Prosthesis Incorporating A Bone Anchor Having A Deflectable Post And A Compound Spinal Rod".

All of these applications are incorporated by reference in their entirety.

CROSS-REFERENCES TO RELATED APPLICATIONS

This application is related to all of the following applications including:

U.S. patent application Ser. No. 12/566,478, filed Sep. 24, 2009, entitled "Modular In-Line Deflection Rod And Bone Anchor System And Method For Dynamic Stabilization Of The Spine"; and U.S. patent application Ser. No. 12/566,485, filed Sep. 24, 2009, entitled "Versatile Polyaxial Connector Assembly And Method For Dynamic Stabilization Of The Spine"; and U.S. patent application Ser. No. 12/566,487, filed Sep. 24, 2009, entitled "Versatile Offset Polyaxial Connector And Method For Dynamic Stabilization Of The Spine"; and U.S. patent application Ser. No. 12/566,494, filed Sep. 24, 2009, entitled "Load-Sharing Component Having A Deflectable Post And Method For Dynamic Stabilization Of The Spine"; and U.S. patent application Ser. No. 12/566,498, filed Sep. 24, 2009, entitled "Load-Sharing Bone Anchor Having A Durable Compliant Member And Method For Dynamic Stabilization Of The Spine"; and U.S. patent application Ser. No. 12/566,504, filed Sep. 24, 2009, entitled "Load-Sharing Bone Anchor Having A Deflectable Post With A Compliant Ring And Method For Stabilization Of The Spine"; and U.S. patent application Ser. No. 12/566,507, filed Sep. 24, 2009, entitled "Load-Sharing Bone Anchor Having A Deflectable Post With A Compliant Ring And Method For Stabilization Of The Spine"; and U.S. patent application Ser. No. 12/566,511, filed Sep. 24, 2009, entitled "Load-Sharing Bone Anchor Having A Deflectable Post And Method For Stabilization Of The Spine"; and U.S. patent application Ser. No. 12/566,516, filed Sep. 24, 2009, entitled "Load-Sharing Bone Anchor Having A Natural Center Of Rotation And Method For Dynamic Stabilization Of The Spine"; and U.S. patent application Ser. No. 12/566,519, filed Sep. 24, 2009, entitled "Dynamic Spinal Rod And Method For Dynamic Stabilization Of The Spine"; and U.S. patent application Ser. No. 12/566,522, filed Sep. 24, 2009, entitled "Dynamic Spinal Rod Assembly And Method For Dynamic Stabilization Of The Spine"; and U.S. patent application Ser. No. 12/566,529, filed Sep. 24, 2009, entitled "Configurable Dynamic Spinal Rod And Method For Dynamic Stabilization Of The Spine"; and U.S. patent application Ser. No. 12/566,531, filed Sep. 24, 2009, entitled "A Spinal Prosthesis Having A Three Bar Linkage For Motion Preservation And Dynamic Stabilization Of The Spine"; and U.S. patent application Ser. No. 12/566,534, filed Sep. 24, 2009, entitled "Surgical Tool And Method For Implantation of A Dynamic Bone Anchor"; and U.S. patent application Ser. No. 12/566,547, filed Sep. 24, 2009, entitled "Surgical Tool And Method For Connecting A Dynamic Bone Anchor and Dynamic Vertical Rod"; and U.S. patent application Ser. No. 12/566,551, filed Sep. 24, 2009, entitled "Load-Sharing Bone Anchor Having A Deflectable Post And Centering Spring And Method For Dynamic Stabilization Of The Spine"; and U.S. patent application Ser. No. 12/566,553, filed Sep. 24, 2009, entitled "Load-Sharing Component Having A Deflectable Post And Centering Spring And Method For Dynamic Stabilization Of The Spine"; and U.S. patent application Ser. No. 12/566,559, filed Sep. 24, 2009, entitled "Load-Sharing Bone Anchor Having A Deflectable Post And Axial Spring And Method For Dynamic Stabilization Of The Spine"; and U.S. patent application Ser. No. 12/629,811, filed Dec. 2, 2009, entitled "Low Profile Spinal Prosthesis Incorporating A Bone Anchor Having A Deflectable Post And A Compound Spinal Rod"; and International Patent Application No. PCT/US2009/066567, filed Dec. 3, 3009, entitled "Low Profile Spinal Prosthesis Incorporating A Bone Anchor Having A Deflectable Post And A Compound Spinal Rod".

All of the afore-mentioned patent applications are incorporated herein by reference in their entireties.

BACKGROUND OF INVENTION

Back pain is a significant clinical problem and the costs to treat it, both surgical and medical, are estimated to be over $2 billion per year. One method for treating a broad range of degenerative spinal disorders is spinal fusion. Implantable medical devices designed to fuse vertebrae of the spine to treat have developed rapidly over the last decade. However, spinal fusion has several disadvantages including reduced range of motion and accelerated degenerative changes adjacent the fused vertebrae.

Alternative devices and treatments have been developed for treating degenerative spinal disorders while preserving motion. These devices and treatments offer the possibility of treating degenerative spinal disorders without the disadvantages of spinal fusion. However, current devices and treatments suffer from disadvantages e.g., complicated implantation procedures; lack of flexibility to conform to diverse patient anatomy; the need to remove tissue and bone for implantation; increased stress on spinal anatomy; insecure anchor systems; poor durability, and poor revision options. Consequently, there is a need for new and improved devices and methods for treating degenerative spinal disorders while preserving motion.

SUMMARY OF INVENTION

The present invention includes a spinal implant system and methods that can dynamically stabilize the spine while providing for the preservation of spinal motion. Embodiments of the invention provide a dynamic stabilization system which includes: versatile components, adaptable stabilization assemblies, and methods of implantation. An aspect of embodiments of the invention is the ability to stabilize two, three and/or more levels of the spine by the selection of appropriate components of embodiments of the invention for implantation in a patient. Another aspect of embodiments of the invention is the ability to accommodate particular anatomy of the patient by providing a system of versatile components which may be customized to the anatomy and needs of a particular patient and procedure. Another aspect of the invention is to facilitate the process of implantation and minimize disruption of tissues during implantation.

Thus, the present invention provides new and improved systems, devices and methods for treating degenerative spinal disorders by providing and implanting a dynamic spinal stabilization assembly which supports the spine while preserving motion. These and other objects, features and advantages of the invention will be apparent from the drawings and detailed description which follow.

BRIEF DESCRIPTION OF THE DRAWINGS

FIGS. 1A and 1B are perspective views of a deflection system component mounted to an anchor system component according to an embodiment of the present invention.

FIG. 1E is a posterior view of an anchor system for a multi-level dynamic stabilization assembly utilizing the anchor components of FIGS. 1A to 1D according to an embodiment of the present invention.

FIG. 2A is an exploded view of a deflection rod according to an embodiment of the present invention.

FIGS. 2E and 2F are sectional views of the deflection rod assembly of FIGS. 2A and 2B showing deflection of the post.

FIG. 2G is a transverse sectional view of a vertebra illustrating the implantation of the deflection rod assembly of FIGS. 2A and 2B.

FIG. 3C is a sectional view of the deflection rod assembly of FIGS. 3A and 3B.

FIG. 3D is a sectional view of the deflection rod assembly of FIGS. 3A and 3B showing deflection of the post.

FIG. 8A shows an exploded view of an alternative bone anchor according to an embodiment of the invention.

FIG. 8B shows a perspective view of the alternative bone anchor of FIG. 8A as assembled.

FIG. 8C shows a sectional view of the alternative bone anchor of FIG. 8A as assembled.

FIG. 8D shows a sectional view of the alternative bone anchor of FIG. 8A illustrating deflection of the deflectable post.

FIG. 8E shows a perspective view of an optional component for the alternative bone anchor of FIGS. 8A-8D according to an embodiment of the invention.

FIG. 8F shows a sectional view of the alternative bone anchor of FIG. 8A including the optional component of FIG. 8E and illustrating deflection of the deflectable post.

FIG. 9A shows an exploded view of an alternative bone anchor according to an embodiment of the invention.

FIG. 9B shows a perspective view of the alternative bone anchor of FIG. 9A as assembled.

FIG. 9C shows a sectional view of the alternative bone anchor of FIG. 9A.

FIG. 9D shows a sectional view of the alternative bone anchor of FIG. 9A as assembled and illustrating deflection of the deflectable post.

FIG. 9E shows a sectional view of a variation of the alternative bone anchor of FIG. 9A as assembled and illustrating deflection of the deflectable post.

FIG. 9F shows a sectional view of a variation of the alternative bone anchor of FIG. 9E as assembled.

FIG. 10C shows a schematic view of an alternative spinal implant component utilizing a self-centering ball-joint according to an embodiment of the invention.

FIGS. 11A-11G show alternative embodiments for centering rods for use in embodiments of the present invention.

FIG. 13A shows a perspective view of an implantation tool for a dynamic bone anchor according to an embodiment of the invention.

FIGS. 13B and 13C show detailed sectional views of the head of the implantation tool of FIG. 13A in relation to a dynamic bone anchor.

FIG. 14E-14H are a lateral views of the lumbar spine illustrating steps to secure a dynamic spinal rod to a dynamic bone anchor assembly using the attachment tool of FIG. 14A according to an embodiment of the invention.

FIG. 15A shows an exploded view of an alternative bone anchor according to an embodiment of the invention.

FIG. 15B shows a perspective view of the alternative bone anchor of FIG. 15A as assembled.

FIG. 15C shows a sectional view of the alternative bone anchor of FIG. 15A.

FIG. 15D shows a sectional view of the alternative bone anchor of FIG. 15A as assembled and illustrating deflection of the deflectable post.

DETAILED DESCRIPTION OF THE PREFERRED EMBODIMENTS

Figure 1C:
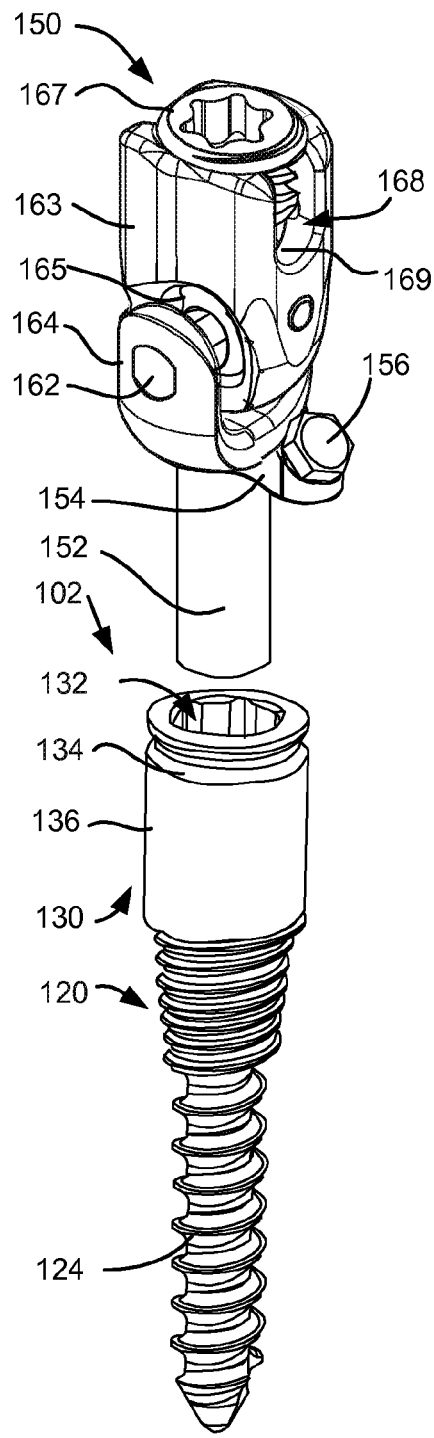
FIG. 1C is a perspective view of a connection system component mounted to an anchor system component according to an embodiment of the present invention.

The present invention includes a versatile spinal implant system and methods which can dynamically stabilize the spine while providing for the preservation of spinal motion. Alternative embodiments can be used for spinal fusion. An aspect of the invention is restoring and/or preserving the natural motion of the spine including the quality of motion as well as the range of motion. Still, another aspect of the invention is providing for load sharing and stabilization of the spine while preserving motion.

Another aspect of the invention is to provide a modular system which can be customized to the needs of the patient. Another aspect of embodiments of the invention is the ability to stabilize two, three and/or more levels of the spine by the selection of appropriate components for implantation in a patient. Another aspect of the invention is the ability to provide for higher stiffness and fusion at one level or to one portion of the spine while allowing for lower stiffness and dynamic stabilization at another adjacent level or to another portion of the spine. Embodiments of the invention allow for fused levels to be placed next to dynamically stabilized levels. Such embodiments of the invention enable vertebral levels adjacent to fusion levels to be shielded by providing a transition from a rigid fusion level to a dynamically stable, motion preserved, and more mobile level.

Embodiments of the present invention provide for assembly of a dynamic stabilization system which supports the spine while providing for the preservation of spinal motion. The dynamic stabilization system has an anchor system, a deflection system, a vertical rod system and a connection system. The anchor system anchors the construct to the spinal anatomy. The deflection system provides dynamic stabilization while reducing the stress exerted upon the bone anchors and spinal anatomy. The vertical rod system connects different levels of the construct in a multilevel assembly and may in some embodiments include compound deflection rods. The connection system includes coaxial connectors and offset connectors which adjustably connect the deflection system, vertical rod system and anchor system allowing for appropriate, efficient and convenient placement of the anchor system relative to the spine. Alternative embodiments can be used for spinal fusion.

Embodiments of the invention include a construct with an anchor system, a deflection system, a vertical rod system and a connection system. The deflection system provides dynamic stabilization while reducing the stress exerted upon the bone anchors and spinal anatomy. The anchor system anchors the deflection system to the spine. The connection system connects the deflection system to the vertical rod system. The vertical rod system connects dynamic stabilization system components on different vertebra to provide load sharing and dynamic stabilization.

Embodiments of the present invention include a deflectable post which provides load sharing while preserving range of motion and reducing stress exerted upon the bone anchors and spinal anatomy. The deflectable post is connected to a bone anchor by a ball-joint which permits the deflectable post to pivot and rotate relative the bone anchor. The kinematics of the deflectable post may be adapted to the anatomy and functional requirements of the patient.

Embodiments of the present invention include a deflectable post which provides load sharing while preserving range of motion and reducing stress exerted upon the bone anchors and spinal anatomy. The deflectable post is connected to a bone anchor by a ball-joint which permits the deflectable post to pivot and rotate relative the bone anchor. A flexible centering rod within the ball-joint serves to align the deflectable post with the axis of the bone anchor. The kinematics of the deflectable post may be adapted to the anatomy and functional requirements of the patient.

Embodiments of the present invention include a compound spinal rod which provides load sharing while preserving range of motion and reducing stress exerted upon the bone anchors and spinal anatomy. The compound spinal rod includes a coupling which is adapted to be fixed to the deflectable post. The coupling is connected by a pivoting joint to a rod which is adapted to be connected to a bone anchor on an adjacent vertebra. The pivoting joint permits the spinal rod to pivot about an axis perpendicular to the longitudinal axis of the spinal rod.

Embodiments of the present invention include a compound spinal rod which provides load sharing while preserving range of motion and reducing stress exerted upon the bone anchors and spinal anatomy. The compound spinal rod includes a rod-end which is adapted to be fixed to the deflectable post. The rod-end is connected by a sliding-rotating joint to a rod which is adapted to be connected to a bone anchor on an adjacent vertebra. The rod-end includes a coupling to mount to a bone anchor. The sliding-rotating joint permits the coupling to be positioned such that the deflectable post is oriented in a preferred orientation relative to the bone anchor of which it is part.

Embodiments of the present invention include an assembly comprising a bone anchor, and deflectable post assembled with a compound spinal rod. The assembly provides load sharing while preserving range of motion and reducing stress exerted upon the bone anchors and spinal anatomy. The deflectable post is connected to a bone anchor by a ball-joint which permits the deflectable post to pivot and rotate relative the bone anchor. The compound spinal rod includes a coupling which is adapted to be fixed to the deflectable post. The coupling is connected by a pivoting joint to a rod which is adapted to be connected to a bone anchor on an adjacent vertebra. The pivoting joint permits the spinal rod to pivot about an axis perpendicular to the longitudinal axis of the spinal rod. The assembly permits movement of adjacent vertebrae in a manner closely approximately the natural kinematics of the spine.

Common reference numerals are used to indicate like elements throughout the drawings and detailed description; therefore, reference numerals used in a drawing may or may not be referenced in the detailed description specific to such drawing if the associated element is described elsewhere. The first digit in a three digit reference numeral indicates the series of figures in which the referenced item first appears. Likewise the first two digits in a four digit reference numeral.

The terms "vertical" and "horizontal" are used throughout the detailed description to describe general orientation of structures relative to the spine of a human patient that is standing. This application also uses the terms proximal and distal in the conventional manner when describing the components of the spinal implant system. Thus, proximal refers to the end or side of a device or component closest to the hand operating the device, whereas distal refers to the end or side of a device furthest from the hand operating the device. For example, the tip of a bone screw that enters a bone would conventionally be called the distal end (it is furthest from the surgeon) while the head of the screw would be termed the proximal end (it is closest to the surgeon).

Dynamic Stabilization System

FIGS. 1A-1F introduce components of a dynamic stabilization system according to an embodiment of the present invention. The components include anchor system components, deflection rods, vertical/spinal rods and connection system components, including for example coaxial and offset connectors. The components may be implanted and assembled to form a dynamic stabilization system appropriate for the anatomical and functional needs of a patient.

FIG. 1A shows a bone anchor 102 and a deflection rod 104 connected to a vertical/spinal rod 106 by a ball joint 108. Deflection rod 104 is an example of a component of the deflection rod assembly system. Deflection rod 104 is a component having controlled flexibility which allows for load sharing. The deflection rod 104 provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod in order to match the load sharing characteristics desired. For embodiments of this invention, the terms "deflection rod" and "loading rod" can be used interchangeably. Deflection rods, deflection rod mountings and alternative deflection rods are described in more detail below.

Deflection rod 104 includes a deflectable post 105 which may deflect relative to a mount 107. Mount 107 is adapted to secure the deflectable post 105 to bone anchor 102. Mount 107 is received within cavity 132 of bone anchor 102. When received in cavity 132, mount 107 is secured into a fixed position relative to bone anchor 102. Deflectable post 105 may still deflect in a controlled manner relative to bone anchor 102 thereby provide for load sharing while preserving range of motion of the patient. The stiffness/flexibility of deflection of the deflectable post 105 relative to mount 107/bone anchor 102 may be controlled and/or customized as will be described below.

As shown in FIG. 1A, mount 107 is designed to be received within a cavity 132 of bone anchor 102. As shown in FIG. 1A, mount 107 includes a collar 140. A threaded aperture 142 extends obliquely through collar 140. The threaded aperture 142 receives a locking set screw 144 which, when seated (FIG. 1B), engages the housing 130 of bone anchor 102. Locking set screw 144 is positioned within threaded aperture 142 through collar 140. The locking set screw 144 thereby secures the mount 107 of deflection rod 104 in place within the housing 130 of bone anchor 102.

As shown in FIG. 1A, deflection rod 104 is oriented in a co-axial, collinear or parallel orientation to bone anchor 102. This arrangement simplifies implantation, reduces trauma to structures surrounding an implantation site, and reduces system complexity. Arranging the deflection rod 104, co-axial with the bone anchor 102 can substantially transfer a moment (of) force applied by the deflectable post 105 from a moment force tending to pivot or rotate the bone anchor 102 about the axis of the shaft, to a moment force tending to act perpendicular to the axis of the shaft. The deflection rod can thereby effectively resist repositioning of the deflection rod and/or bone anchor 102 without the use of locking screws or horizontal bars to resist rotation. Further examples of coaxial deflection rods are provided below. Each of the deflection rods described herein may be used as a component of a dynamic stabilization system.

Bone anchor 102 is an example of a component of the anchor system. Bone anchor 102 includes a bone screw 120 and housing 130. As shown in FIG. 1A, bone anchor 102 is a bone screw 120 having one or more threads 124 which engage a bone to secure the bone anchor 102 onto a bone. The anchor system may include one or more alternative bone anchors known in the art e.g. bone hooks, expanding devices, barbed devices, threaded devices, adhesive and other devices capable of securing a component to bone instead of or in addition to bone screw 120.

As shown in FIG. 1A, bone anchor 102 includes a housing 130 at the proximal end. Housing 130 includes a cavity 132 for receiving deflection rod 104. Cavity 132 is coaxial with threaded bone screw 120. Housing 130 also comprises a groove 134 for securing deflection rod 104 within housing 130. As shown in FIG. 1A, groove 134 is located at the proximal end of housing 130. Groove 134 is designed to be engaged by the locking mechanism of a component mounted within cavity 132. For example, groove 134 is designed to be engaged by locking set screw 144 of deflection rod 104. When deflection rod 104 has been positioned within cavity 132 of bone anchor 102 as shown in FIG. 1B, locking set screw 144 is tightened to engage groove 134 of housing 130 thus securing deflection rod 104 within housing 130. Alternative mechanisms and techniques may be used to secure the deflection rod to the bone anchor including for example, welding, soldering, bonding, and/or mechanical fittings including threads, snap-rings, locking washers, cotter pins, bayonet fittings or other mechanical joints.

Bone anchor 102 also includes a coupling 136 to which other components may be mounted. As shown in FIG. 1A, coupling 136 is the external cylindrical surface of housing 130. Housing 130 thus provides two mounting positions, one coaxial mounting position and one external mounting position. Thus, a single bone anchor 102 can serve as the mounting point for one, two or more components. A deflection rod 104 may be coaxially mounted in the cavity 132 of the housing and one or more additional components may be externally mounted to the outer surface 136 of the housing. For example, a component of the connection system may be mounted to the outer surface 136 of the housing—such a connector may be called an offset head or offset connector. In some applications a component of the connection system may be coaxially-mounted in the cavity 132 in place of a deflection rod 104—such a connector may be called a coaxial head or coaxial connector.

It is desirable to have a range of different connectors which are compatible with the anchor system and deflection system. The connectors may have different attributes, including for example, different degrees of freedom, range of motion, and amount of offset, which attributes may be more or less appropriate for a particular relative orientation and position of two bone anchors and/or patient anatomy. It is desirable that each connector be sufficiently versatile to connect a vertical rod to a bone anchor in a range of positions and orientations while being simple for the surgeon to adjust and secure. It is desirable to provide a set of connectors which allows the dynamic stabilization system to be assembled in a manner that adapts a particular dynamic stabilization assembly to the patient anatomy rather than adapting the patient anatomy for implantation of the assembly (for example, by removing tissue\bone to accommodate the system). In a preferred embodiment, the set of connectors comprising the connection system have sufficient flexibility to allow the dynamic stabilization system to realize a suitable dynamic stabilization assembly in all situations that will be encountered within the defined patient population.

In some embodiments of the present invention, a connection system component, e.g. a polyaxial connector may be mounted in the cavity 132 of a bone anchor 102 to secure the bone anchor to vertical rod 106. For example, FIG. 1C shows coaxial head 150 which is a polyaxial connector which is coaxially mounted within the cavity 132 of the housing 130 of bone anchor 102. Coaxial head 150 is an example of a coaxial head or coaxial connector. Bone anchor 102 is the same bone anchor previously described with respect to FIGS. 1A and 1B. Coaxial head 150 comprises a rod 152 which is designed to fit within cavity 132 of housing 130. Coaxial head 150 also comprises a collar 154 and locking set screw 156. Locking set screw 156 is configured to engage groove 134 of bone anchor 102 in the same way as locking set screw 144 of deflection rod 104. Rod 152 and cavity 132 may in some case be circular in section (e.g. cylindrical), in which case rod 152 can rotate within cavity 132 until locked into place by locking set screw 156. In alternative embodiments, rod 152 may be polygonal in section such that it fits in one of a fixed number of possible positions.

Referring again to FIG. 1C, attached to rod 152 of coaxial head 150 is a yoke 164. Yoke 164 is connected to a ball 165 by a hexagonal pin 162. A saddle 163 is also mounted to ball 165 such that saddle 163 can pivot about two orthogonal axes relative to yoke 164. Saddle 163 has an aperture 168 through which a vertical rod may be passed. On one side of aperture 168 is a plunger 169. On the other side of aperture 168 is a locking set screw 167. When a vertical rod 106 (not shown) is positioned within aperture 168 and locking set screw 167 is tightened down, the locking set screw 167 forces the vertical rod 106 down onto the plunger 169. Plunger 169 is, in turn, forced down by the vertical rod 106 against ball 165. Plunger 169 engages ball 165, and ball 165 engages hexagonal pin 162, to lock saddle 163 in position relative to yoke 164 and secure a rod (e.g. vertical rod 106) to saddle 163. In this way, tightening set screw 167 secures the vertical rod 106 to the coaxial head 150 and also locks orientation of the coaxial head 150.

The ability to coaxially mount coaxial head 150 to a bone anchor 102 has several advantages over a standard polyaxial bone screw in which a polyaxial connector is an integral part of the device and may not be removed or exchanged. The bone anchor 102 is simpler to install and there is no risk of damage to the polyaxial connector during installation. A single coaxial head 150 can be manufactured and designed to mount to a range of different bone anchors thus allowing bone anchors to be selected as appropriate for the patient anatomy. After the bone anchor is installed, the orientation of the yoke 164 can be adjusted without changing the screw depth (this is not possible in a standard polyaxial bone screw without also turning the screw). After the bone anchor is implanted, one of a range of different coaxial heads may be installed without requiring removal of the bone anchor. Likewise, if a revision is required, the coaxial head may be exchanged for a different component without necessitating removal of the bone anchor 102.

Figure 1D:
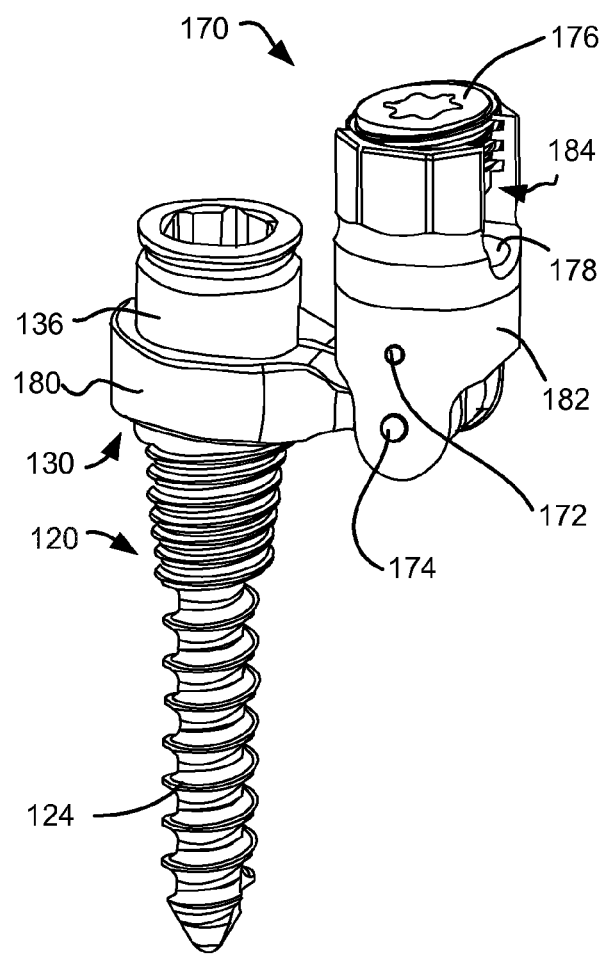
FIG. 1D is a perspective view of a different connection system component mounted to an anchor system component according to an embodiment of the present invention.

As described above, bone anchor 102 has housing 130 which can accept one coaxially-mounted component (e.g. a coaxial head) and one externally-mounted component (e.g. an offset connector). FIG. 1D shows a component of the connection system which may be mounted externally to housing 130 of bone anchor 102 in conjunction with a coaxially-mounted component. FIG. 1D shows a perspective view of offset connector 170 mounted externally to housing 130 of bone anchor 102 in which a deflection rod 104 is coaxially mounted. Connector 170 may be termed an offset head or offset connector.

Offset connector 170 comprises six components and allows for two degrees of freedom of orientation and two degrees of freedom of position in connecting a vertical rod to a bone anchor. The six components of offset connector 170 are dowel pin 172, pivot pin 174, locking set screw 176, plunger 178, clamp ring 180 and saddle 182. Saddle 182 has a slot 184 sized to receive a rod which may be a vertical rod, e.g. vertical rod 106 of FIG. 1A. Locking set screw 176 is mounted at one end of slot 184 such that it may be tightened to secure a rod within slot 184.

Clamp ring 180 is sized such that, when relaxed it can slide freely up and down the housing 130 of bone anchor 102 and rotate around housing 130. However, when locking set screw 176 is tightened on a rod, the clamp ring 180 grips the housing and prevents the offset connector 170 from moving in any direction. Saddle 182 is pivotably connected to clamp ring 180 by pivot pin 174. Saddle 182 can pivot about pivot pin 174. However, when locking set screw 176 is tightened on a rod, the plunger 178 grips the clamp ring 180 and prevents further movement of the saddle 182. In this way, operation of the single set screw 176 serves to lock the clamp ring 180 to the housing 130 of the bone anchor 102, fix saddle 182 in a fixed position relative to clamp ring 180 and secure a rod within the slot 184 of offset connector 170.

The above-described coaxial connector and offset connector are provided by way of example only. Alternative embodiments of coaxial heads and offset connectors can be found in U.S. Provisional Patent Application No. 61/100,625, filed Sep. 26, 2008 entitled "Versatile Assembly Components And Methods For A Dynamic Spinal Stabilization System" which is incorporated by reference. These coaxial heads and offset connectors may be used in conjunction with the components herein described to permit assembly of a dynamic stabilization system appropriate to the functional needs and anatomy of a particular patient. In addition screws having an integrated connector may also be utilized to anchor components of the dynamic stabilization system in fixed relationship to a vertebra, for example polyaxial screws.

The components of the dynamic stabilization system may be assembled and implanted in the spine of a patient to provide a multilevel dynamic stabilization assembly which provides dynamic stabilization of the spine and load sharing. In some embodiments, the first step is implantation of bone anchors in the vertebrae. In other embodiments, the bone anchors may be implanted with the deflection rod/connection component already installed.

FIG. 1E, shows three adjacent vertebrae 191, 192 and 193. As a preliminary step, bone anchors 102a, 102b and 102c have been implanted in the vertebrae 191, 192 and 193 on the right side of the spinous process 194 between the spinous process 194 and the transverse process 195. A driver is inserted into the cavity 132a, 132b, 132c in order to drive the threaded portion of each bone anchor into the bone. In preferred procedures, the bone anchor is directed so that the threaded portion is implanted within one of the pedicles 196 angled towards the vertebral body 197. The threaded region of each bone anchor is fully implanted in the vertebrae 191, 192 and 193. A driver may alternatively and/or additionally engage the exterior surface of housing 130 in order to implant the bone anchor. The driver may have a torque-measuring and/or torque limiting function to assist in accurate implantation of the bone screw and avoid excess force being applied to the vertebrae. In alternative embodiments, the bone screw may incorporate a torque limiting element, for example a secondary head which breaks away when the driver torque exceeds a predetermined torque limit. See, e.g. FIGS. 7F-7H and accompanying text.

As shown in FIG. 1E, the housings 130a, 130b, 130c of each bone anchor remain partly or completely exposed above the surface of the vertebrae so that one or more of a connection system component and deflection component can be secured to each bone anchor 102a, 102b and 102c. Coaxial components may be coaxially-mounted inside each of cavities 132a, 132b, and 132c. Offset heads/connectors may also be externally-mounted to the outside surface of each of housings 130a, 130b and 130c. Note that bone anchors are also implanted on the left side of the spine.

Figure 1F:
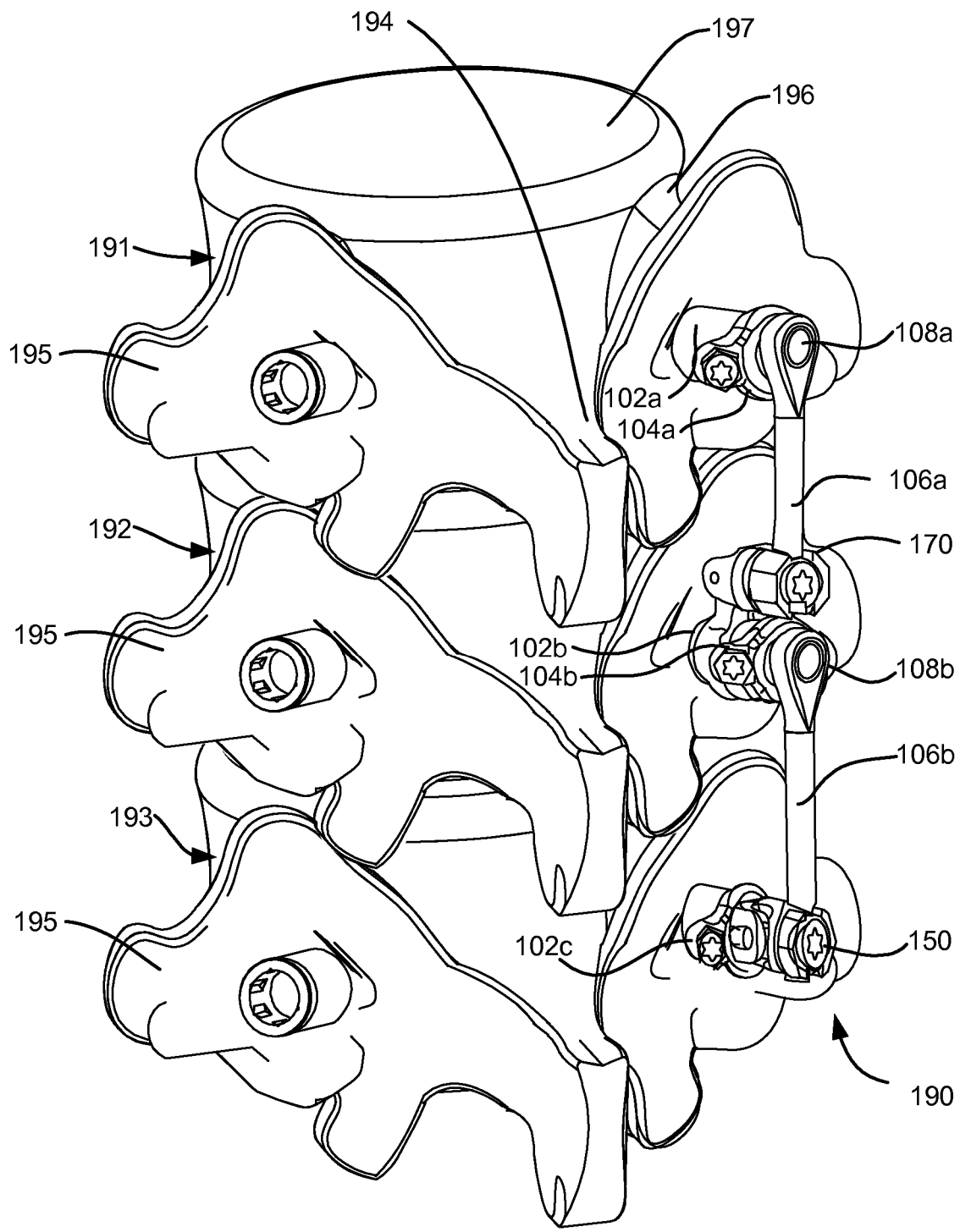
FIG. 1F is a posterior view of a multi-level dynamic stabilization assembly utilizing the components of FIGS. 1A to 1E according to an embodiment of the present invention.

After installation of the bone anchors, the deflection system components, vertical rod systems components and connection system components may be installed and assembled. FIG. 1F shows one way to assemble deflection system components and connection system components. As shown in FIG. 1F, a coaxial head 150 is installed in bone anchor 102c. An offset connector 170 is mounted externally to the housing of bone anchor 102b. A deflection rod 104a is coaxially mounted in the housing of bone anchor 102a. A deflection rod 104b is coaxially mounted in the housing of bone anchor 102b. A vertical rod 106a is connected at one end to deflection rod 104a by ball joint 108a. Vertical rod 106a is connected at the other end by in-line connector 170 to bone anchor 102b. A second vertical rod 106b is connected at one end to deflection rod 104b by ball joint 108b. Vertical rod 106b is connected at the other end by coaxial head 150 to bone anchor 102c.

The dynamic stabilization assembly 190 of FIG. 1E thus has a vertical rod 106a, 106b stabilizing each spinal level (191-192 and 192-193). Each of the vertical rods 106a, 106b is secured rigidly at one end to a bone anchor (102b, 102c). Each of the vertical rods 106a, 106b is secured at the other end by a ball joint 108a, 108b to a deflection rod 104a, 104b thereby allowing for some movement and load sharing by the dynamic stabilization assembly. Offset connector 170 and coaxial head 150 permit assembly of dynamic stabilization assembly 190 for a wide range of different patient anatomies and/or placements of bone anchors 102a, 102b and 102c. An identical or similar dynamic stabilization assembly would preferably be implanted on the left side of the spine. It should be noted that dynamic stabilization assembly 190 does not require horizontal bars or locking screws thereby reducing the exposure of tissue and/or bone to foreign bodies compared to systems with this additional hardware. The dynamic stabilization assembly of FIG. 1F, thereby, has a small footprint, potentially reducing the amount of displacement of tissue and/or bone, reducing trauma to tissue and/or bone during surgery. Further, the smaller footprint can reduce the amount of tissue that needs to be exposed during implantation.

Deflection Rods/Loading Rods

One feature of embodiments of the present invention is the load sharing and range of motion provided by a deflection rod. The deflection rod provides stiffness and support where needed to support the loads exerted on the spine during normal spine motion thereby recovering improved spine function without sacrificing all motion. The deflection rod also isolates the anchor systems components from forces exerted by the dynamic stabilization assembly thereby reducing stress on the bone anchors and the bone to which they are attached. Moreover, by selecting the appropriate stiffness of the deflection rod or loading rod to match the physiology of the patient and the loads that the patient places on the spine, a better outcome is realized for the patient.

The deflection rod includes a deflectable post, a compliant sleeve and a mount. The deflectable post and mount are typically made of biocompatible metal or metals, e.g. titanium and stainless steel. The sleeve is made of a compliant material, for example a compliant polymer. The mount secures the deflection rod to an anchoring device in a manner which allows deflection of the deflectable post. The deflectable post is configured to connect to the vertical rod system. The deflectable post may deflect relative to the mount by compressing the compliant material of the sleeve. The deformation of the sleeve imparts force/deflection characteristics to the deflectable post. The movement of the post relative to the mount allows controlled movement of the bone anchor (and vertebra in which it is implanted) relative to the vertical rods thereby supporting the vertebrae to which the bone anchors are attached while allowing movement of the vertebrae.

Deflection rods can be manufactured in a range from highly rigid configurations to very flexible configurations by appropriate selection of the design, materials and dimensions of the post, sleeve and mount. Deflection rods having a particular stiffness/flexibility may be selected for use in a dynamic stabilization assembly based upon the physiological needs of a particular patient. In a preferred embodiment deflection rod stiffness/flexibility is selected to provide load sharing in conjunction with from 50% to 100% of the normal range of motion of a patient and more preferably 70% to 100% of the normal range of motion of a patient.

In some cases, certain of the deflection rods of a dynamic stabilization assembly can have a different stiffness or rigidity or flexibility than other of the deflection rods. Thus, in the same assembly, a first deflection rod can have a first flexibility or stiffness or rigidity, and a second deflection rod can have a second different flexibility or stiffness or rigidity depending on the needs of the patient. Particular embodiments of a dynamic stabilization assembly may utilize deflection rods having different deflection properties for each level and/or side of the dynamic stabilization assembly. In other words, one portion of a dynamic stabilization assembly may offer more resistance to movement than the other portion based on the design and selection of different stiffness characteristics, if that configuration benefits the patient.

Figure 2B:
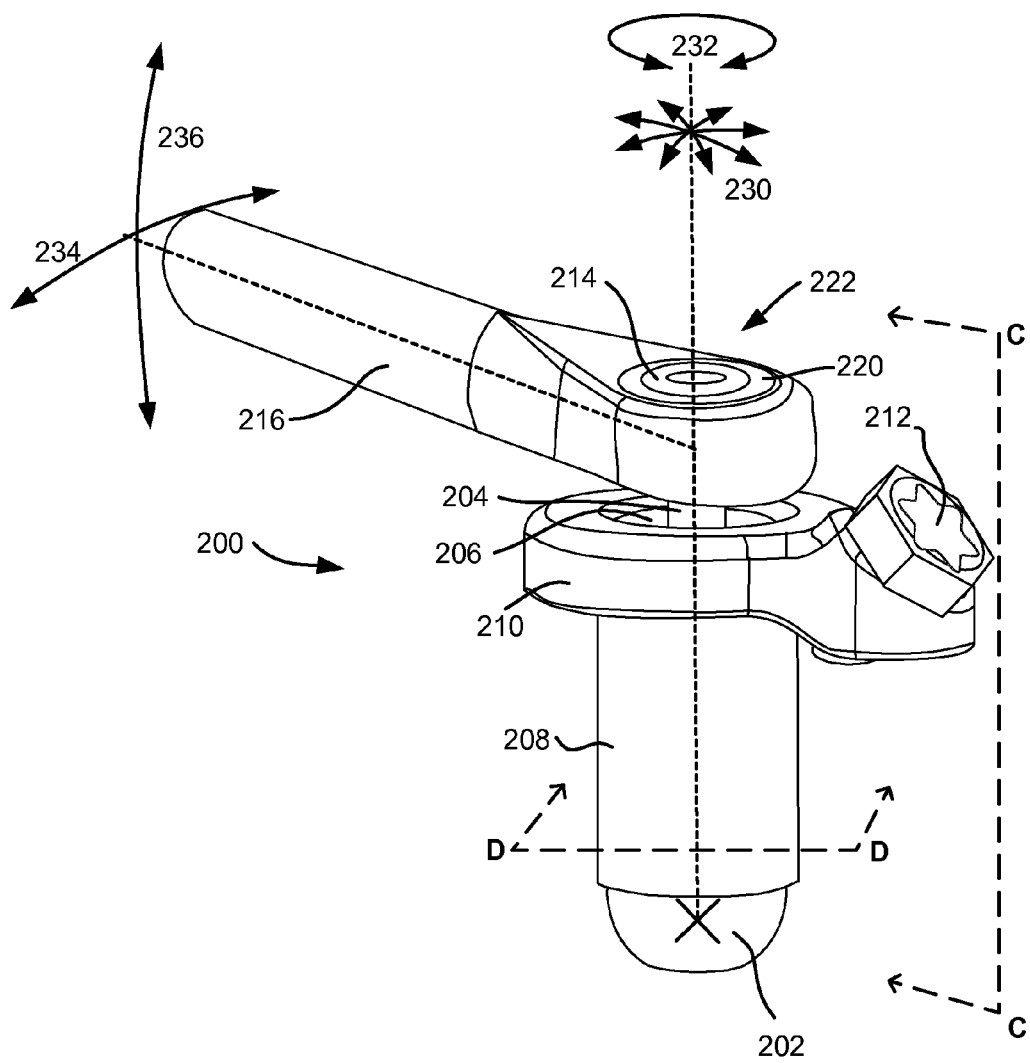
FIG. 2B is a perspective view of the deflection rod assembly of FIG. 2A, as assembled.

FIGS. 2A through 2G illustrate the design and operation of a first embodiment of a deflection rod according to an embodiment of the present invention. FIG. 2A shows an exploded view of deflection rod 200. Deflection rod 200 includes retainer 202, deflectable post 204, sleeve 206, shield 208, collar 210, screw 212 and ball 214. Deflection rod 200 connects to vertical rod 216 at a ball joint which includes ball 214, pocket 218 and cap 220. Shield 208 and collar 210 are securely attached to each other (or formed in one piece) and make up the mount 207. A threaded aperture 211 passes obliquely through collar 210. Threaded aperture 211 is configured to receive a screw 212. Sleeve 206 is made of a compliant material which permits movement of deflectable post 204 relative to shield 208. Deflectable post 204 may thus pivot in any direction about the center of ball-shaped retainer 202 as shown by arrows 230. The sleeve 206 controls and limits the deflection of the deflectable post 204. The deflectable post 204 can also rotate about the longitudinal axis of the post and the bone anchor as shown by arrow 232.

Referring now to FIG. 2B, which shows a perspective view of a fully assembled deflection rod 200. When assembled, deflectable post 204 is positioned within sleeve 206; sleeve 206 is positioned within shield 208. Ball 214 is connected to the proximal end of deflectable post 204 to provide a component of a ball joint for connecting deflection rod 200 to a vertical rod 216. Ball 214 may be formed in one piece with deflectable post 204 or may be securely attached to deflectable post 204 using a joint, for example, a threaded joint, welded joint, adhesive joint. Retainer 202 is attached to the distal end of deflectable post 204 to prevent deflectable post 204 from being pulled out of sleeve 206.

As shown in FIG. 2A, the retainer 202 may be a ball-shaped retainer 202. Retainer 202 may be formed in one piece with deflectable post 204 or may be securely attached to deflectable post 204. The retainer 202 may be attached by laser welding, soldering or other bonding technology. For example, retainer 202 in the form of a ball, disk, plate or other shape may be laser welded to the distal end of deflectable post 204. Alternatively, retainer 202 may mechanically engage the deflectable post 204 using, for example, threads. For example, a lock ring, toothed locking washer, cotter pin or other mechanical device can be used to secure deflectable post 204 within shield 208.

The ball 214 of deflection rod 200 is received in a pocket of vertical rod 216. Cap 220 secures ball 214 within the pocket of vertical rod 216 creating a ball joint 222 which allows vertical rod 216 to rotate 360 degrees around the axis of deflectable post 204 (as shown by arrow 234) and also tilt away from the plane perpendicular to the axis of deflectable post 204 (as shown by arrow 236). Thus, the vertical rod 216 is allowed to rotate and/or have tilting and/or swiveling movements about a center which corresponds with the center of ball 214 of ball joint 222. Ball 214 can also be displaced relative to shield 208 by deflection of deflectable post 204 (as shown by arrows 230).

Figure 2C:
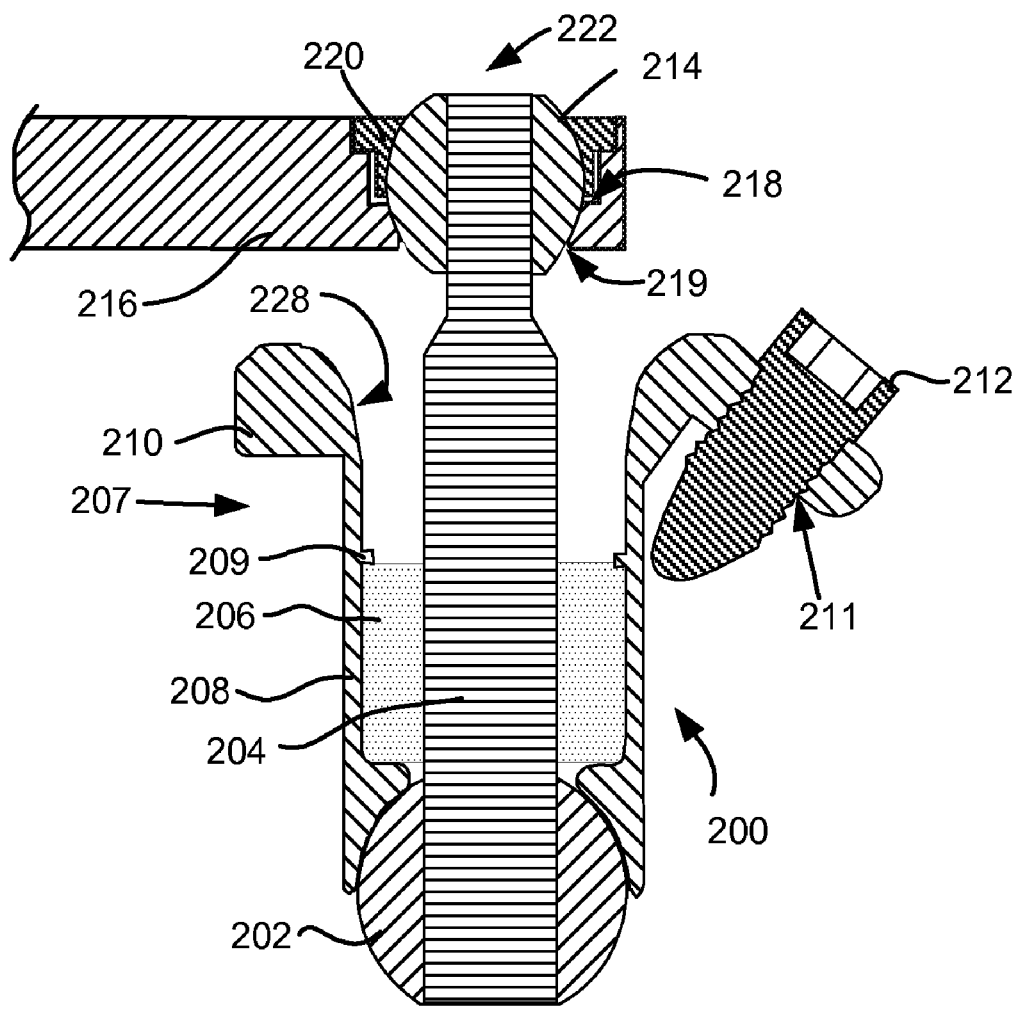
FIG. 2C is a sectional view of the deflection rod assembly of FIGS. 2A and 2B.

FIG. 2C shows a sectional view of a fully assembled deflection rod 200 along the axis indicated by line C-C of FIG. 2B. As shown in FIG. 2C, sleeve 206 occupies the space between deflectable post 204 and shield 208 and is compressed by deflection of deflectable post 204 towards shield 208 in any direction. In some embodiments, sleeve 206 may be formed separately from deflection rod 200. For example, deflectable post 204 and sleeve 206 may be press fit into shield 208. Alternatively or additionally, a biocompatible adhesive may be used to bond the sleeve 206 to the shield 208 and/or deflectable post 204. Alternatively, sleeve 206 may be formed in place by positioning the deflectable post 204 within the shield 208 and then filling the space between the deflectable post 204 and the shield 208 with liquid polymer (polymer reagents) and allowing the polymer to solidify (polymerize).

FIG. 2C, also illustrates the internal detail of ball joint 222 which connects vertical rod 216 and deflectable post 204 of deflection rod 200. Vertical rod 216 includes disk-shaped pocket 218 at one end. The proximal end of deflectable post 204 is passed through aperture 219 in disk-shaped pocket 218 of the vertical rod 216. The diameter of deflectable post 204 is smaller than the diameter of aperture 219. Once the proximal end of deflectable post 204 is passed through the aperture 219, ball 214 is attached to deflectable post 204 using threading, fusing, gluing, press fit and/or laser welding techniques, for example. The diameter of the aperture 219 is less than the diameter of ball 214 to prevent ball 214 from passing back through aperture 219. Once ball 214 is positioned within the disk-shaped pocket 218 of vertical rod 216, cap 220 is threaded, fused, glued, press fit and/or laser welded, for example, into pocket 218 thereby securing ball 214 within disk shaped pocket 218. FIG. 2C also shows an optional ridge 209 on the interior of shield 208 for retaining sleeve 206.

Figure 2D:
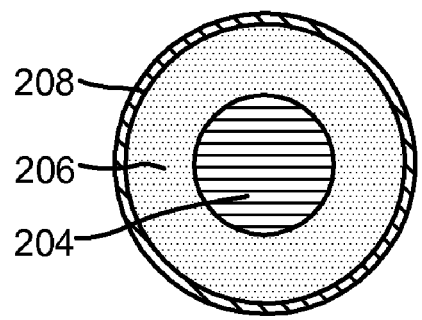
FIG. 2D is a sectional view of the deflection rod assembly of FIGS. 2A and 2B.

FIG. 2D shows a sectional view of a fully assembled deflection rod 200 along the axis indicated by line D-D of FIG. 2B. As shown in FIG. 2D, sleeve 206 occupies the space between deflectable post 204 and shield 208 and is compressed by deflection of deflectable post 204 towards shield 208 in any direction. Sleeve 206 resists deflection of deflectable post 204 outwardly from a position that is collinear with the longitudinal axis of sleeve 206. The dimensions and material of sleeve 206 may be adjusted to generate the desired deflection/load characteristics for the deflection rod.

FIGS. 2E and 2F illustrate deflection of deflectable post 204. Applying a force to ball-joint 222 causes deflection of deflectable post 204 relative to mount 207 including shield 208 (and any bone anchor to which it may be mounted). Initially deflectable post 204 pivots about a pivot point 203 indicated by an X. In this embodiment pivot point 203 is located at the center of ball-shaped retainer 202. In other embodiments however, pivot point may positioned at a different location. As shown in FIG. 2E, deflection of deflectable post 204 initially compresses the material of sleeve 206 between deflectable post 204 and shield 208. The force required to deflect deflectable post 204 depends upon the dimensions of deflectable post 204, sleeve 206 and shield 208 as well as the attributes of the material of sleeve 206.

By changing the dimensions of deflectable post 204, sleeve 206 and shield 208, the deflection characteristics of deflection rod 200 can be changed. The stiffness of components of the deflection rod can be, for example, increased by increasing the diameter of the post and/or by decreasing the diameter of the inner surface of the shield and deflection guide. Additionally, increasing the diameter of the post will increase the stiffness of the deflection rod while decreasing the diameter of the post will decrease the stiffness of the deflection rod. Alternatively and/or additionally changing the materials which comprise the components of the deflection rod can also affect the stiffness and range of motion of the deflection rod. For example, making sleeve 206 out of stiffer and/or harder material reduces deflection of deflectable post 204.

The stiffness of the deflection rod may thus be varied or customized according to the needs of a patient. The deflection characteristics of the deflection rod can be configured to approach the natural dynamic motion of the spine, while giving dynamic support to the spine in that region. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine. In some cases, a kit is provided to a doctor having a set of deflection rods with different force/deflection characteristics from which the doctor may select the deflection rods most suitable for a particular patient. In other cases, the surgeon may select deflection rods prior to the procedure based upon pre-operative assessment.

Sleeve 206 is preferably made of a compliant biocompatible polymer. Sleeve 206 may, for example, be made from a polycarbonate urethane (PCU) such as Bionate®. If the sleeve is comprised of Bionate®, a polycarbonate urethane or other hydrophilic polymer, the sleeve can also act as a fluid-lubricated bearing for rotation of the deflectable post 204 relative to the longitudinal axis of the deflectable post 204 (see arrow 232 of FIG. 2B). In a preferred embodiment, the sleeve is made of PCU, is 2 mm thick when uncompressed and may be compressed to about 1 mm in thickness by deflection of the post.

The sleeve may also include polymer regions having different properties. For example, the sleeve can include concentric rings of one or more polymers with each ring having a different hardness of stiffness or durometer. For example, each successive ring from the center outward can have a higher hardness or stiffness or durometer so that as the post is deflected outwardly from a position that is collinear with the longitudinal axis of the sleeve provides increased resistance to further deflection. The sleeve may also be designed to provide different force deflection characteristics in different directions. The deflectable post could also be designed so that less resistance occurs with increased deflection of the post.

As shown in FIG. 2F, after further deflection, deflectable post 204 comes into contact with limit surface 228 of shield 208. Limit surface 228 is oriented such that when deflectable post 204 makes contact with limit surface 228, the contact is distributed over an area to reduce stress on deflectable post 204 and limit surface 228. As depicted, limit surface 228 is configured such that as the deflectable post 204 deflects into contact with limit surface 228, limit surface 228 is aligned/flat relative to deflectable post 204 in order to present a larger surface to absorb any load and also to reduce stress on deflectable post 204 and limit surface damage. Additional deflection may cause elastic deformation of deflectable post 204. Because deflectable post 204 is relatively stiff, the force required to deflect deflectable post 204 increases significantly after contact of deflectable post 204 with shield 208. In a preferred embodiment, deflectable post 204 may deflect from 0.5 mm to 2 mm in any direction before making contact with limit surface 228. More preferably, deflectable post 204 may deflect approximately 1 mm before making contact with limit surface 228.

Thus, as load or force is first applied to the deflection rod by the spine, the deflection of the deflection rod responds about linearly to the increase in the load during the phase when deflection of deflectable post 204 causes compression of sleeve 206 as shown in FIG. 2E. After about 1 mm of deflection, when deflectable post 204 contacts limit surface 228 (as shown in FIG. 2F) the deflection rod becomes stiffer. Thereafter, a greater amount of load or force needs to be placed on the deflection rod in order to obtain the same incremental amount of deflection that was realized prior to this point because further deflection requires bending of deflectable post 204. Accordingly, the deflection rod provides a range of motion where the load supported increases about linearly as the deflection increases and then with increased deflection the load supported increases more rapidly in a non-linear manner in order to provide stabilization. Put another way, the deflection rod becomes stiffer as the deflection/load increases. In a dynamic stabilization assembly incorporating the deflection rod, the load sharing and deflection is provided by the deflection rod between the deflectable post and the bone screw or the overall bone anchor such as bone anchor 102 and to a lesser degree or not in the vertical rod such as the vertical rod 106 (FIG. 1B).

FIG. 2G is a sectional view illustrating the implantation of deflection rod 200 in a vertebra 240. As shown in FIG. 2G, bone anchor 102 is oriented such that is passes through pedicle 242 into vertebral body 244. Note that the length of bone anchor 102 is selected based upon the anatomy of the patient. Thus shorter bone anchors are used in smaller vertebrae and longer bone anchors are used in larger vertebrae. As shown in FIG. 2G, bone anchor 102 has shallower threads 250 adjacent housing 130. Threads 250 engage the harder cortical bone 246 on the surface of the vertebra 240. Bone anchor 102 has deeper threads 252 towards the distal end of bone anchor 102. Threads 252 engage the softer cancellous bone 248 within the vertebral body 244.

As shown in FIG. 2G, deflection rod 200 is mounted within bone anchor 102 such that pivot point 203 is positioned below the surface of vertebra 240. Deflectable post 204 pivots about this pivot point 203 positioned within vertebra 240. This is advantageous in that it places pivot point 203 of deflectable post 204 closer to the vertebral body 244 and thus closer to the natural instantaneous center of rotation of the spine. Placing pivot point 203 closer to the vertebral body 244 promotes natural motion and reduces non physiological forces on the bones and strain on the system. Placing the pivot point 203 closer to the vertebral body 244 also helps isolate bone anchor 102 from the relative motion between vertebra 240 and the vertical rod 216 which connects one vertebra to another vertebra. Pivot point 203 is preferably at or below the surface of the vertebra and more preferably pivot point 203 is within the cancellous bone 248 of the vertebrae 240. Even more preferably, the pivot point 203 is positioned with the pedicle 242 of the vertebra 240. In some cases, pivot point 203 may be positioned within vertebral body 244.

Alternative Deflection Rods/Loading Rods

Figure 3A:
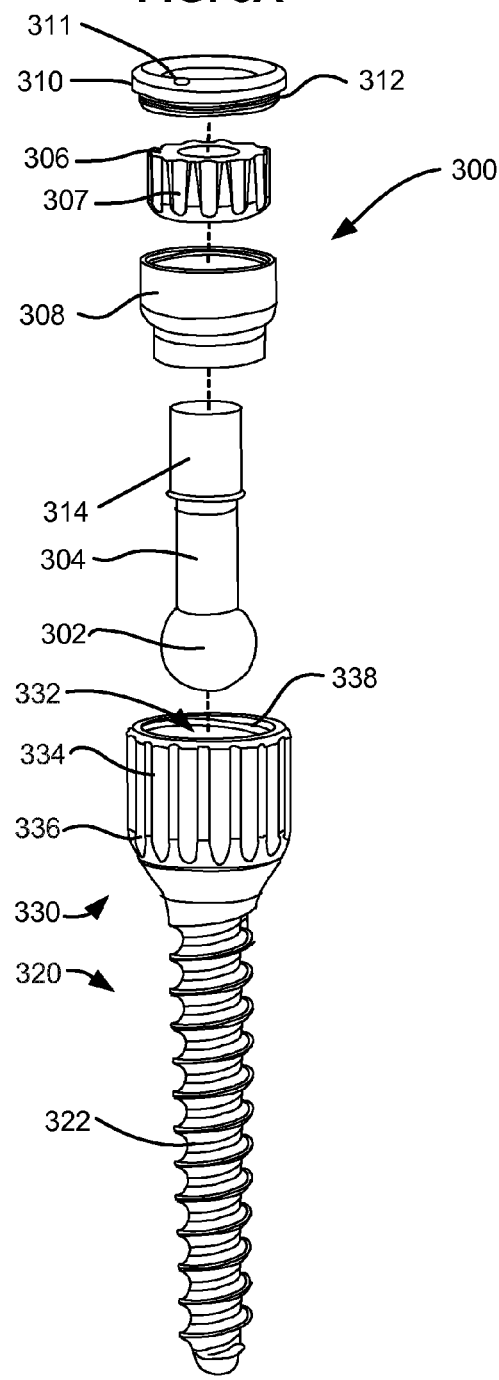
FIG. 3A is an exploded view of an alternative deflection rod assembly according to an embodiment of the present invention.

FIGS. 3A-3H illustrate a first alternative deflection rod 300. FIG. 3A shows an exploded view of alternative deflection rod 300. Deflection rod 300 includes ball-shaped retainer 302, deflectable post 304, sleeve 306, shield 308, collar 310, and mount 314. In this embodiment, retainer 302 is a spherical structure formed in one piece with deflectable post 304. Mount 314, in this embodiment, is the proximal end of deflectable post 304 suitable for connecting to a vertical rod. A ball may be used in place of mount 314 as previously described. In this embodiment, mount 314 is formed in one piece with deflectable post 304 and retainer 302. In alternative embodiments, deflectable post 304 may be formed separately from and securely attached to one or more of mount 314 and retainer 302 by laser welding, soldering or other bonding technology. Alternatively, deflectable post 304 may be formed separately and mechanically engage one or more of mount 314 and retainer 302 using, for example, threads. For example, a lock ring, toothed locking washer, cotter pin or other mechanical device can be used to secure deflectable post 304 to one or more of mount 314 and retainer 302.

Sleeve 306 is made of a compliant material which permits movement of deflectable post 304 relative to shield 308. The sleeve 306 effectively controls and limits the deflection of the deflectable post 304. Sleeve 306 is preferably made of a compliant biocompatible polymer such as PCU by way of example only. The properties of the material and dimensions of the sleeve 306 are selected to achieve the desired force/deflection characteristics for deflectable post 304. In a preferred embodiment, the sleeve is made of PCU (Bionate® 80A) and is 2 mm thick when uncompressed and may be compressed to about 1 mm in thickness by deflection of the post. Sleeve 306 may also be shaped to modify the compliance of sleeve 306, for example by providing flutes 307. Sleeve 306 fits inside shield 308 surrounding deflectable post 304.

Deflection rod 300 is configured to be mounted in a bone anchor 320, which comprises a bone screw 322 connected to a housing 330. Housing 330 has a cavity 332 oriented along the axis of bone anchor 320 at the proximal end and configured to receive deflection rod 300. Housing 330 also has an outer surface 334 adapted for mounting a component e.g. an offset connector. Housing 330 may in some embodiments be cylindrical as previously described. As shown in FIG. 3A, outer surface 334 of housing 330 is provided with splines/flutes 336. Splines/flutes 336 may be engaged by a driver that mates with splines/flutes 336 for implanting bone anchor 320.

Figure 3B:
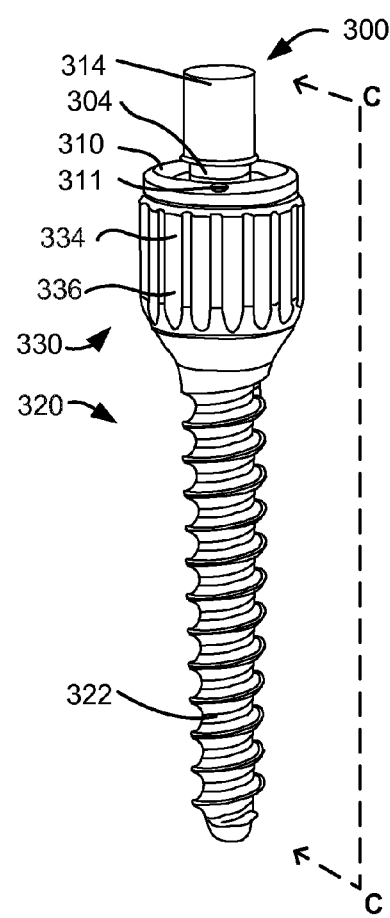
FIG. 3B is a perspective view of the deflection rod assembly of FIG. 3A, as assembled.

Referring now to FIG. 3B, which shows a perspective view of a deflection rod 300 assembled with a bone anchor 320. When assembled, deflectable post 304 is positioned within sleeve 306 of FIG. 3A; sleeve 306 is positioned within shield 308 of FIG. 3A. Deflectable post 304, sleeve 306 and shield 308 are then placed in the cavity 332 of FIG. 3A of bone anchor 320. Threaded collar 310 is then secured in the threaded proximal end of cavity 332. Threaded collar 310 has two sockets 311 for receiving the pins of a pin wrench to allow threaded collar 310 to be tightened to threads 338 of housing 330. Threaded collar 310 is laser welded to housing 330 after installation to further secure the components. Threaded collar 310 secures deflectable post 304, sleeve 306 and shield 308 within cavity 332 of bone anchor 320.

FIG. 3C shows a sectional view of a deflection rod 300 assembled with a bone anchor 320 along the axis indicated by line C-C of FIG. 3B. As shown in FIG. 3C, sleeve 306 occupies the space between deflectable post 304 and shield 308 and is compressed by deflection of deflectable post 304 towards shield 308 in any direction. Retainer 302 fits into a hemispherical pocket 339 in the bottom of cavity 332 of housing 330. Shield 308 includes a flange 309 which secures ball-shaped retainer 302 within hemispherical pocket 339 while allowing rotation of ball-shaped retainer 302. Collar 310 secures both shield 308 and sleeve 306 within housing 330. If sleeve 306 is comprised of Bionate®, a polycarbonate urethane or other hydrophilic polymer, sleeve 306 can act as a fluid lubricated bearing and allow the post to also rotate about the longitudinal axis of the post and the bone anchor. Other materials and configurations can also allow the post to rotate about the longitudinal axis of the post and the bone anchor.

FIG. 3D illustrates the deflection of deflectable post 304. Applying a force to mount 314 causes deflection of deflectable post 304 of deflection rod 300. Initially deflectable post 304 pivots about a pivot point 303 indicated by an X. Deflectable post 304 may pivot about pivot point 303 in any direction. Concurrently or alternatively, deflectable post 304 can rotate about the long axis of deflectable post 304 (which also passes through pivot point 303). In this embodiment, pivot point 303 is located at the center of ball-shaped retainer 302. As shown in FIG. 3D, deflection of deflectable post 304 initially compresses the material of sleeve 306. The force required to deflect deflectable post 304 depends upon the dimensions of deflectable post 304, sleeve 306 and shield 308 as well as the attributes of the material of sleeve 306.

After further deflection, deflectable post 304 comes into contact with limit surface 313 of collar 310. Limit surface 313 is oriented such that when deflectable post 304 makes contact with limit surface 313, the contact is distributed over an area to reduce stress on deflectable post 304. After deflectable post 304 comes into contact with limit surface 313, further deflection requires deformation (bending) of deflectable post 304. In a preferred embodiment, deflectable post 304 is a titanium post 5 mm in diameter. Deflectable post 304 is relatively stiff, and the force required to deflect deflectable post 304 therefore increases significantly after contact of deflectable post 304 with collar 310. In a preferred embodiment, deflectable post 304 may deflect from 0.5 mm to 2 mm in any direction before making contact with limit surface 313. More preferably, deflectable post 304 may deflect approximately 1 mm before making contact with limit surface 313.

The inner diameter of the collar 310 may be different in different collars so that the distance between limit surface 313 and deflectable post 304 is different in different deflection rods. This allows for the manufacture of deflection rods having a larger or smaller range of deflection before contact between the post and the limit surface. In this way, deflection rods may be manufactured having different ranges of motion. Moreover, the distance between limit surface 313 and deflectable post 304 need not be the same in all directions such that the range of motion of the deflection rod is different in different directions.

Referring to FIG. 3D, as load or force is first applied to the deflection rod 300 by the spine, the deflection of deflectable post 304 responds about linearly to the increase in the load during the phase when deflection of deflectable post 304 causes compression of sleeve 306. After about 1 mm of deflection, deflectable post 304 contacts limit surface 313 and the deflection rod becomes substantially stiffer. A greater amount of load or force needs to be placed on the deflection rod in order to obtain the same amount of incremental deflection that was realized prior to this point because further deflection requires bending of deflectable post 304. The amount of deflection caused by the load applied is a non-linear function, in this embodiment. The deflection rod provides a range of motion where the load supported increases about linearly as the deflection increases and then with increased deflection the load supported increases more rapidly (upon contact of the post with the limit surface). Alternatively, if desired, this embodiment could be designed such that the rate of change of the amount of deflection could be a linear function for a larger range of motion by; for example, increasing the distance between limit surface 313 and deflectable post 304.

Figure 3E:
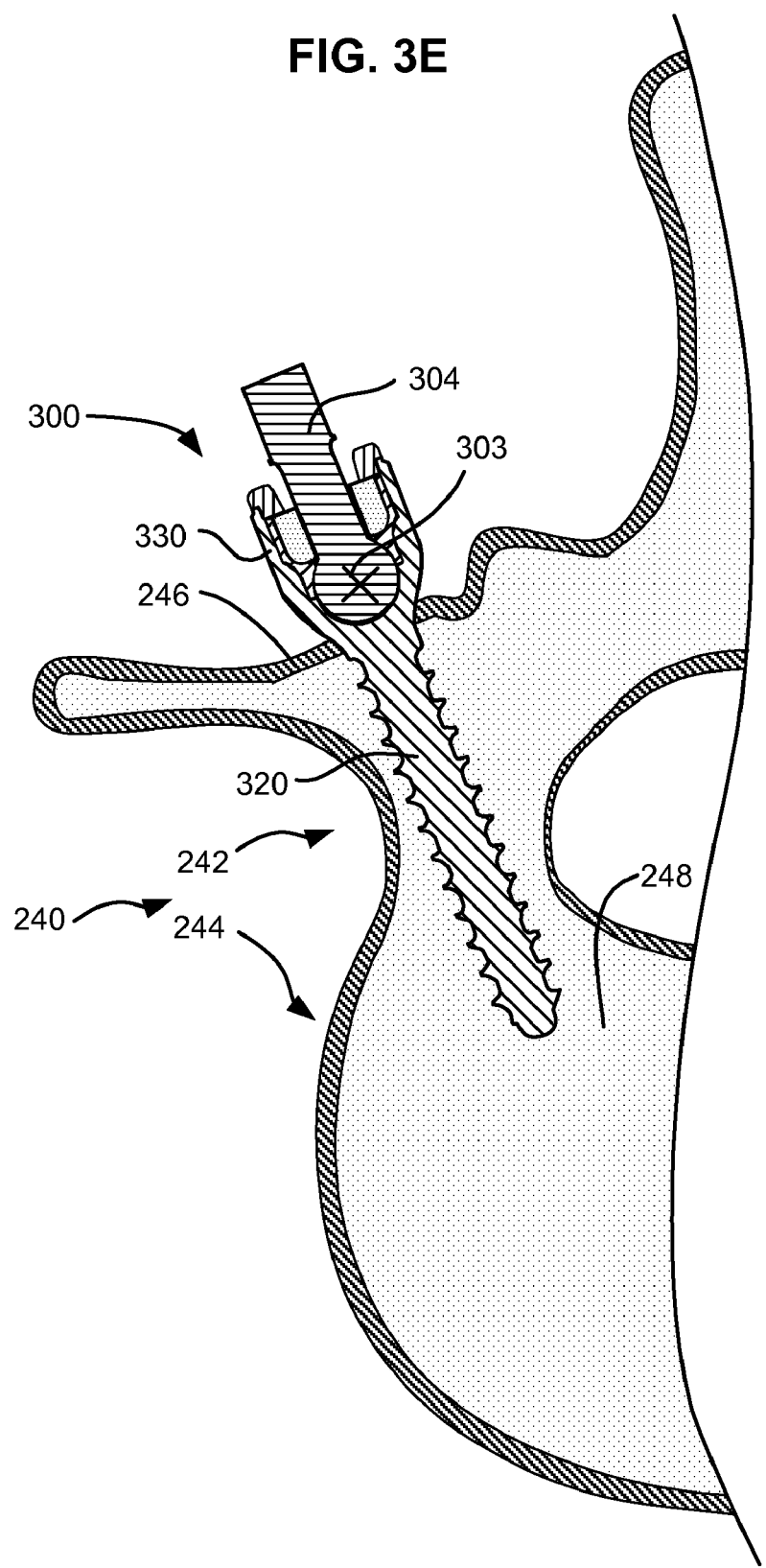
FIG. 3E is a transverse sectional view of a vertebra illustrating the implantation of the deflection rod assembly of FIGS. 3A and 3B.

FIG. 3E is a sectional view illustrating the implantation of a deflection rod 300 in a vertebra 240. As shown in FIG. 3E, bone anchor 320 is oriented such that is passes through pedicle 242 into vertebral body 244. Note that the length of bone anchor 320 is selected based upon the anatomy of the patient. Thus shorter bone anchors are used in smaller vertebrae and longer bone anchors are used in larger vertebrae. As shown in FIG. 3E, housing 330 of bone anchor 320 is mounted entirely above the surface of vertebra 240. Pivot point 303 of deflection rod 300 is positioned within housing 330 such that pivot point 303 is, in this embodiment, positioned close to but outside of vertebra 240.

Figure 3F:
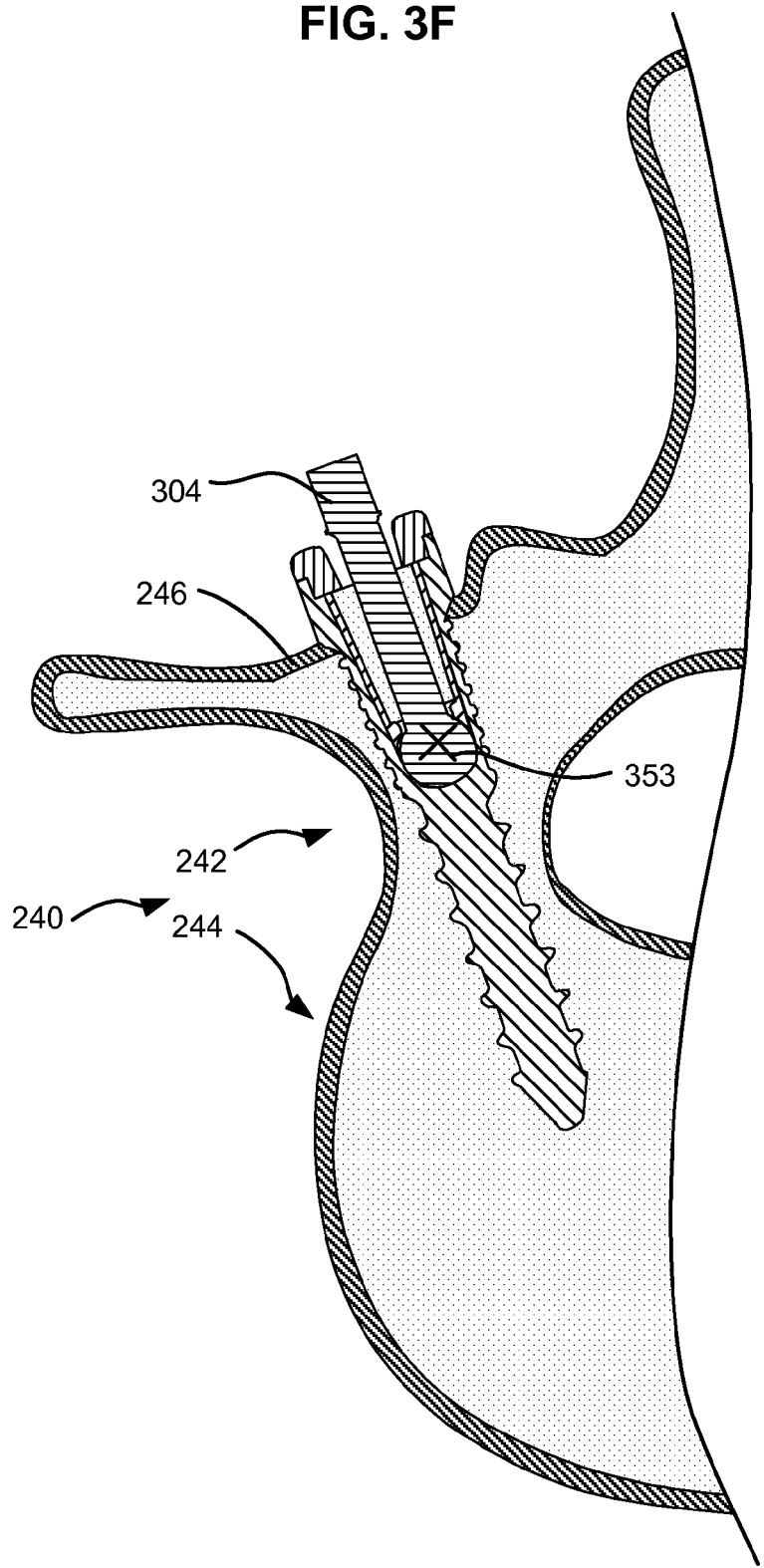
FIG. 3F is a transverse sectional view of a vertebra illustrating the implantation of an alternative deflection rod.

In an alternative embodiment, as shown in FIG. 3F, deflectable post 304 pivots about a pivot point 353 positioned within vertebra 240. This is advantageous in that it places pivot point 353 of deflectable post 304 closer to the vertebral body 244 and thus the natural instantaneous center of rotation of the spine. Placing the pivot point 353 closer to the vertebral body 244 promotes natural motion and reduces non-physiological forces on the bones and strain on the dynamic stabilization assembly. In particular, placing the pivot point 353 closer to the vertebral body 244 helps isolate bone anchor 320 from the relative motion between vertebra 240 and a vertical rod of the dynamic stabilization assembly which connects one level of the spine to the adjacent level. Pivot point 353 is preferably at or below the surface of the vertebra 240. More preferably, the pivot point 353 is positioned with the pedicle 242 of the vertebra 240. In some cases, pivot point 353 may be positioned within vertebral body 244.

Figure 3G:
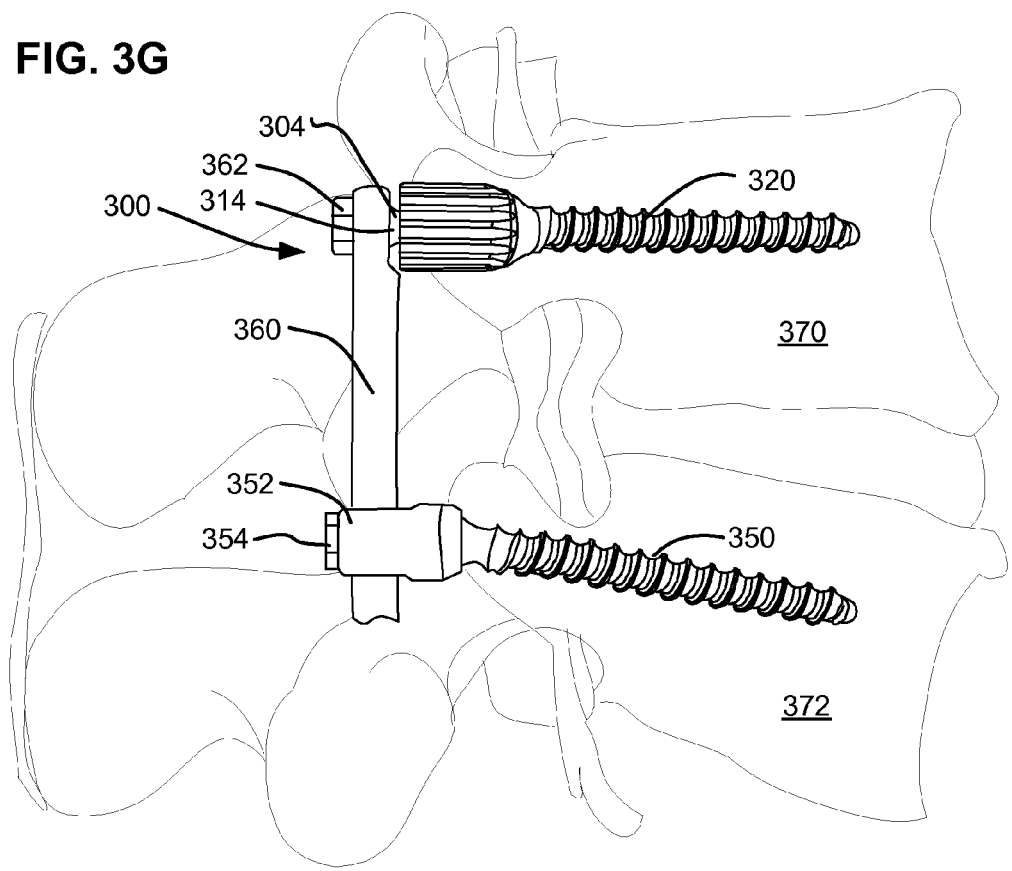
FIG. 3G is a lateral view of a multi-level dynamic stabilization assembly utilizing the deflection rod assembly of FIGS. 3A-3B according to an embodiment of the present invention.

FIG. 3G shows a lateral view of a dynamic stabilization assembly utilizing deflection rod 300. As shown in FIG. 3G, deflection rod 300 is installed in bone anchor 320. Bone anchor 320 is implanted in one vertebra 370 (see e.g. FIG. 3E). A polyaxial screw 350 is implanted in a second vertebra 372. A vertical rod 360 is secured at one end to mount 314 of deflection rod 300. Mount 314 in this embodiment passes through an aperture in vertical rod 360. The proximal end of mount 314 is threaded so that vertical rod 360 may be secured to mount 314 with a threaded nut 362. In this embodiment, as shown in FIG. 3G, the vertical rod 360 is secured rigidly to deflectable post 304. The rigid connection provides a relatively stiff assembly. However, where greater range of motion is desired, deflectable post 304 may be provided with a ball end and vertical rod 360 may be connected to deflectable post 304 by a ball joint as previously described with respect to FIGS. 1A-1B.

Vertical rod 360 is mounted at the other end to the polyaxial head 352 of polyaxial screw 350. This screw may be a standard polyaxial screw, for example, a 5.5 mm polyaxial screw available in the marketplace. This screw may, alternatively, be a bone anchor with a polyaxial head e.g. the polyaxial head previously described with respect to FIG. 1C. In a preferred embodiment, vertical rod 360 is a titanium rod 5.5 mm in diameter as used in rigid spinal implants. The vertical rod 360 is secured to polyaxial head 352 using a threaded fitting, set screw 354, for example. The vertical rod 360 thereby supports the vertebrae while deflection rod 300 provides for load sharing and allows relative motion of vertebra 370 relative to vertebra 372. Thus, the dynamic stabilization assembly provides dynamic stabilization of the spine. The dynamic stabilization assembly may be expanded to two or more levels using an offset connector mounted to the housing 330 of bone anchor 320. It is to be understood that an offset connector can include a fluted ring to assist in engaging the housing 330 (see e.g. shape of open wrench 380 in FIG. 3H). Thus, a modular system is provided which provides for the creation of a multi-level dynamic stabilization assembly.

Figure 3H:
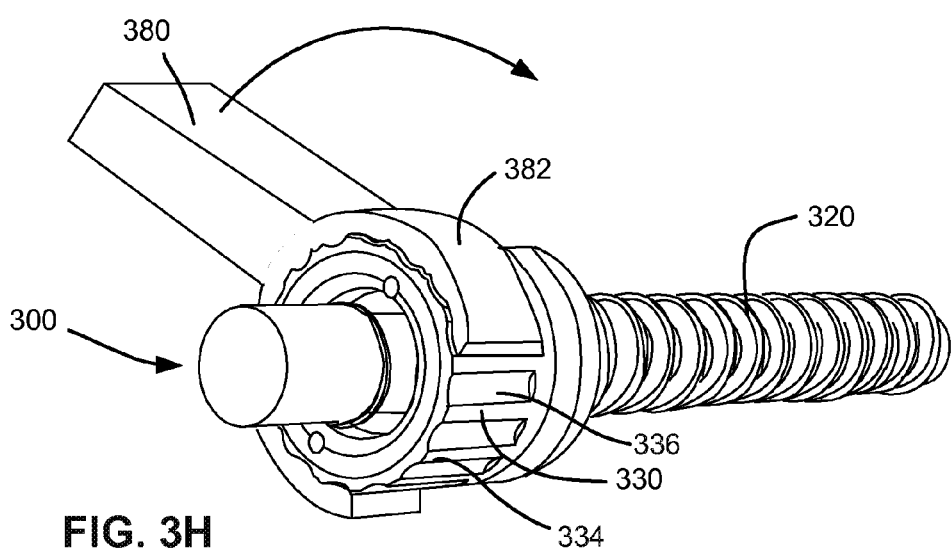
FIG. 3H is an oblique view of an offset connector mounted to the deflection rod assembly of FIGS. 3A-3B according to an embodiment of the present invention.

FIG. 3H illustrates an open wrench 380 for driving bone anchor 320 into position. Bone anchor 320 of FIG. 3H has a housing 330. A deflection rod 300 is installed in housing 330 and secured in place by threaded collar 310 (FIGS. 3A and 3B). Threaded collar 310 engages threads interior to housing 330. Collar 310 has two apertures 311 which may be engaged by a pin wrench to tighten collar 310 to housing 330. Collar 310 may also be welded to housing 330 to further secure deflection rod 300 with housing 330. In this embodiment deflection rod 300 is designed to be preassembled with bone anchor 320 prior to implantation.

As shown in FIG. 3H, the exterior surface 334 of housing 330 is provided with surface features in the form of a plurality of splines 336. Splines 336 are oriented parallel to the longitudinal axis of bone anchor 320 and project from housing 330 at regular intervals. Open wrench 380 has a head 382 designed to engage the exterior surface 334 of housing 330. With such a tool, the housing 330 can be engaged and rotated about the longitudinal axis of the bone anchor 320 in order to drive the bone anchor into the bone. Open wrench 380 may be provided with a torque limiting or torque measuring component to facilitate installation of bone anchor 320. In alternative embodiments a socket may be used to engage housing 330 in place of an open wrench.

Figure 3I:
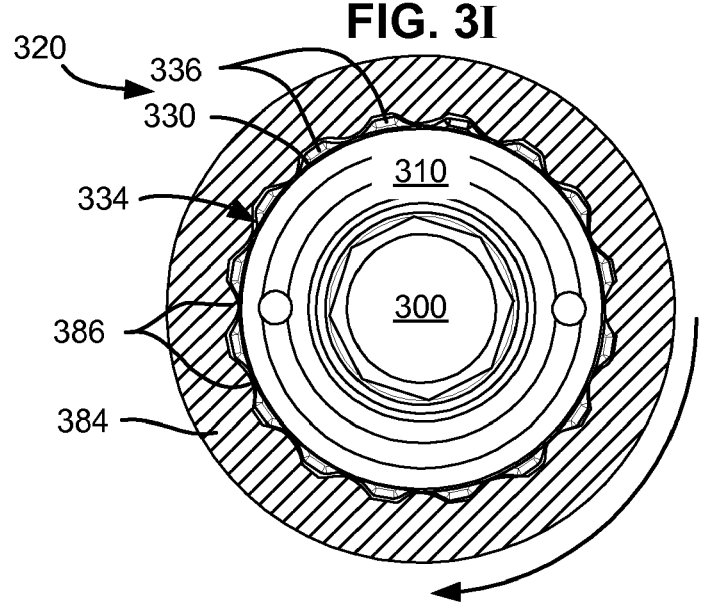
FIG. 3I shows a socket with interior features adapted to engage features of the housing of a deflection rod assembly according to an embodiment of the present invention.

FIG. 3I shows a plan view of bone anchor 320 and deflection rod 300 observed from the deflection rod end of the assembly. As shown in FIG. 3I there are 16 splines 336 evenly spaced around the exterior surface 334 of housing 330. The diameter of collar 310 is the same or smaller as the minimum diameter of housing 330 in the region of the splines 336 to allow engagement of the splines 336 by a complementary tool or connector without interference from collar 310. In other embodiments there may be a greater or lesser number of splines.

FIG. 3I shows a sectional view of a socket wrench 384 suitable for engaging housing 330. Socket wrench 384 has a plurality of splines 386 complementary to splines 336 of housing 330. Socket wrench 384 may therefore be slipped over deflection rod 300 and housing 330 and positioned as shown in FIG. 3I. When in position, socket wrench 384 may be used to rotate housing 330 to install bone anchor 320 in a bone (or remove the bone anchor from the bone). Socket wrench 384 should be complementary in interior profile to the exterior profile 334 of housing 330. Socket wrench 384 need not have as many splines 386 as housing 330 has splines 336 so long as splines 386 are correctly positioned to engage some or all of the splines 336 of housing 330. An open wrench or other driver may be designed with the same engagement surface to engage some or all of the splines 336 of housing 330.

Figure 3J:
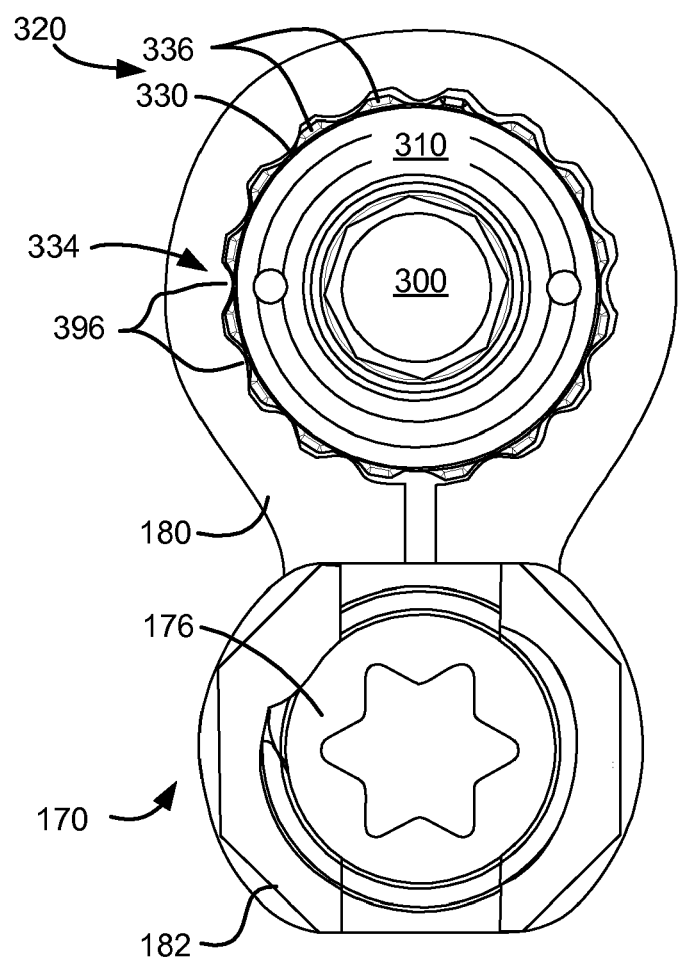
FIG. 3J shows a connector with interior features adapted to engage features of the housing of a deflection rod assembly according to an embodiment of the present invention.

Likewise, connectors that engage the housing of a bone anchor may also be readily adapted to engage splines 336 of housing 330. By way of example, FIG. 3J shows connector 170 of FIG. 1D adapted to engage splines 336. Connector 170 mounts externally of the housing 330 of a bone anchor 320. The components of connector 170 shown in FIG. 3J include locking set screw 176, clamp ring 180 and saddle 182. As shown in FIG. 3J, clamp ring 180 has, on the inside diameter, a plurality of splines 396 complementary to splines 336 of housing 330. Clamp ring 180 may therefore be slipped over deflection rod 300 and housing 330 and positioned as shown in FIG. 3J after implantation of bone anchor 320 in a vertebra. Splines 396 engage splines 336 of housing 330. Clamp ring 180 is prevented by splines 396 and 336 from free rotation around housing 330. This is advantageous in that increases the stability of the dynamic stabilization assembly by preventing the clamp ring 180 from slipping around housing 330 under load. When clamp ring 180 is positioned at the desired angle relative to bone anchor 320, set screw 176 may be tightened onto a vertical rod (not shown) to clamp the vertical rod to the saddle 182 and also tighten clamp ring 180 against the exterior surface 334 of housing 330. Thus connector 180 may be used to securely attach a vertical rod to the housing 330 of bone anchor 320.

Clamp ring 180 (and thus connector 170) may be installed in any of 16 positions around housing 330 (22.5 degrees separation between positions). If smaller granularity of positioning is required, a larger number of splines 336 may be used. Clamp ring 180 should be complementary in interior profile to the exterior surface 334 of housing 330. Clamp ring 180 need not have as many splines 396 as housing 330 has splines 336 so long as the splines 396 are correctly positioned to engage some or all of the splines 336 of housing 330. A clamp ring 180 as shown in FIG. 1D without any splines may still be used to engage housing 330.

Other connectors may be similarly adapted to engage the splines 336 of housing 330 of bone anchor 320. Likewise, the other bone anchors discussed herein may be provided with splines on the exterior of the housing to facilitate installation and enhance the mounting of connectors. In alternative embodiments, different surface features may be utilized on the surface of a housing for engagement by a tool or connector. For example, a housing may be made polygonal in exterior section and have 8, 3, 12, 16 or more sides. A tool or connector for use with such a housing would have a complementary interior profile designed to engage the 8, 3, 12, 16 or more sides. Alternatively, a housing may be provided with a plurality of apertures at regular intervals. A tool or connector for use with such a housing may be provided with a one or more of pins designed to engage the apertures in a plurality of positions in the manner of a pin wrench. Conversely the housing may be provided with one or more protruding pins and the tool or connector with a plurality of complementary apertures. Alternatively, one or both of the housing and connector may be provided with shallow surface features such as dots, dimples, ridges or the like designed to increase the frictional engagement of the housing and connector. In the latter case, the features of the housing and connector need not necessarily be complementary to one another and the connector and housing may be free to engage one another at any angular position.

One feature of embodiments of the present invention is load sharing provided by the deflection rod. The deflection rod provides stiffness and support where needed to support the loads exerted on the spine during normal spine motion thereby recovering improved spine function without sacrificing all motion. The deflection rod also isolates the anchor system components from forces exerted by the dynamic stabilization assembly thereby reducing stress on the bone anchors and the bone to which they are attached. In particular embodiments, the deflection rods of the present invention are oriented coaxial with the longitudinal axis of the bone anchor to which they are attached or in which they are incorporated. Moreover, by selecting the appropriate stiffness of the deflection rod or loading rod to match the physiology of the patient and the loads that the patient places on the spine, a better outcome is realized for the patient.

In order to utilize deflection rods of the present invention to construct a dynamic stabilization assembly, the deflection rod is coupled with a vertical rod. The deflection rod may be coupled to the vertical rods in a fixed, pivoting or flexible manner depending on the requirements of the dynamic stabilization assembly. One mechanism for coupling a deflection rod to a vertical rod is the ball-joint 222 illustrated for example in FIGS. 2A-2C and FIGS. 2E-2G. As shown in FIG. 2B, the vertical rod 216 is coupled to the deflectable post 204 by the ball-joint 222 in a manner that allows the vertical rod 216 to rotate about the long axis of the deflectable post 204 and also pivot relative to the deflectable post 204. These two degrees of freedom are present both during implantation and also in the completed dynamic stabilization assembly. By comparing FIGS. 2C, 2E and 2F, it can be seen that the angle between the vertical rod 216 and deflectable post 204 changes as deflectable post 204 is deflected. This change in angle is accommodated by rotation of ball 214 in ball joint 222.

A second mechanism for coupling a deflection rod to a vertical rod is the threaded mount 314 of deflection rod 300 illustrated in FIGS. 3A-3H. As shown in FIG. 3G, the vertical rod 360 is secured to threaded mount 314 by a nut 362. The vertical rod 360 can be rotated around mount 314 before nut 362 is tightened but, thereafter, vertical rod 360 is rigidly secured to deflectable post 304. After completion of the dynamic stabilization assembly, vertical rod can still rotate around the long axis of bone anchor 320 because deflectable post 304 may rotate relative to the long axis of bone anchor 320. However, the angle between vertical rod 360 and deflectable post 304 is fixed. Thus, any angle change between vertical rod 360 and deflectable post 304 resulting from movement of the vertebra must be accommodated by deformation (bending) of vertical rod 360 and deflectable post 304. Vertical rod 360 and deflectable post 304 are relatively stiff and thus, the dynamic stabilization assembly is stiff as compared to a dynamic stabilization assembly which may accommodate the angle change without bending of the vertical rod and deflectable post using e.g. a ball-joint. Thus, the mechanism by which the vertical rod is coupled to a deflection rod affects the ease by which the dynamic stabilization system may be assembled and also the stiffness of the dynamic stabilization assembly.

Alternative Bone Anchor and Compound Spinal Rod

Figure 4A:
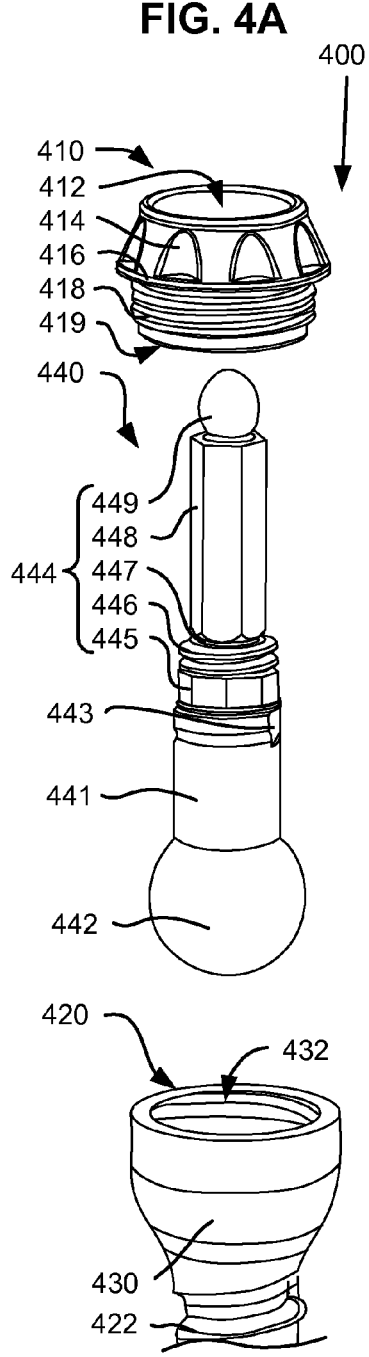
FIG. 4A shows an exploded view of an alternative bone anchor according to an embodiment of the invention.
Figure 4B:
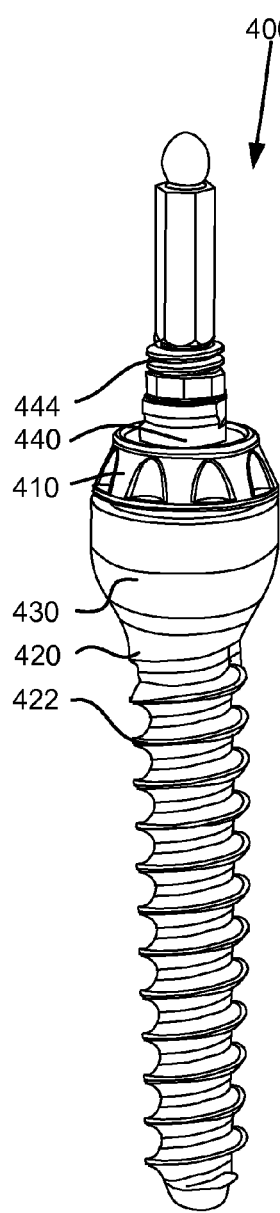
FIG. 4B shows a perspective view of the alternative bone anchor of FIG. 4A as assembled.
Figure 4C:
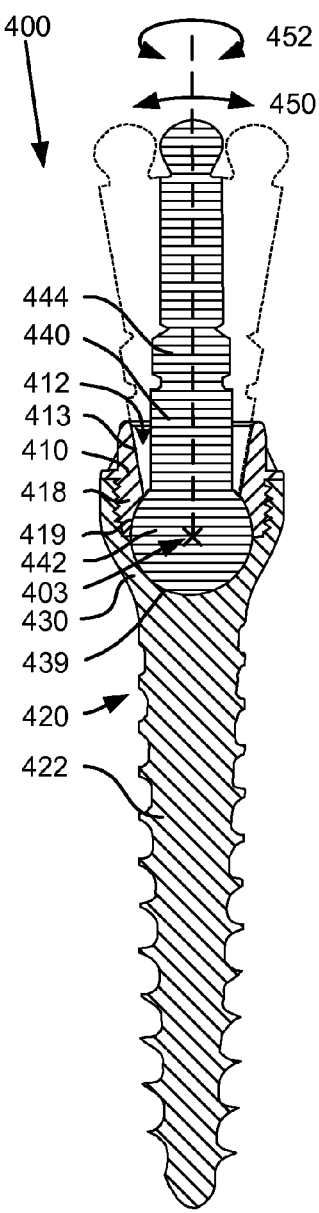
FIG. 4C shows a sectional view of the alternative bone anchor of FIG. 4A as assembled.

FIGS. 4A-4C illustrate a bone anchor and a compound spinal rod which cooperate to closely approximate the natural kinematics of the spine discussed above. FIGS. 4A-4C illustrate a preferred embodiment of a bone anchor 400. FIGS. 5A-5D illustrate a preferred embodiment of a compound spinal rod 500. FIGS. 6A-6C illustrate the combined kinematics of bone anchor 400 combine with compound spinal rod 500 in a dynamic stabilization prosthesis 600.

FIG. 4A shows an exploded view of bone anchor 400. FIG. 4B shows a perspective view of bone anchor 400, as assembled. FIG. 4C shows a sectional view of bone anchor 400. Referring first to FIG. 4A, bone anchor 400 includes, in this embodiment, three components: bone screw 420, deflectable post 440, and cap 410. Bone screw 420 comprises a threaded shaft 422 with a housing 430 at one end. Housing 430 may in some embodiments be cylindrical as previously described and is in some embodiments provided with splines/flutes. Housing 430 is preferably formed in one piece with threaded shaft 422. Housing 430 has a cavity 432 oriented along the axis of threaded shaft 422. Cavity 422 is open at the proximal end of housing 430 and is configured to receive deflectable post 440.

In a preferred embodiment, deflectable post 440 is a titanium post 5 mm in diameter. Deflectable post 440 has a retainer 442 at one end. At the other end of deflectable post 440 is a mount 444. Retainer 442 is a ball-shaped or spherical structure in order to form part of a linkage connecting deflectable post 440 to bone screw 420. Mount 444 is a low profile mount configured to connect deflectable post 440 to a vertical rod component (not shown, but see, e.g. FIGS. 5A-5C). Mount 444 comprises a threaded cylinder 446 to which the vertical rod component may be secured. Mount 444 in some embodiments also comprises a polygonal section 445 to prevent rotation of a component relative to mount 444.

Mount 444 includes a male hex extension 448 which may be engaged by a tool to hold stationary mount 444 during attachment to a vertical rod. At the proximal end of male hex extension is a nipple 449 for securing male hex extension 448 into a tool. Hex extension 448 is breakaway component. Between hex extension 448 and threaded cylinder 446 is a groove 447. Groove 447 reduces the diameter of deflectable post 440 such that hex extension 448 breaks away from threaded cylinder 446 when a desired level of torque is reached during attachment of a vertical rod. The breakaway torque is determined by the diameter of remaining material and the material properties. In a preferred embodiment the breakaway torque is approximately 30 foot pounds. Thus, hex extension 448 breaks away during implantation and is removed. Nipple 449 is engaged by the tool in order to remove hex extension 448. Deflectable post 440 is also provided with flats 443 immediately adjacent mount 444. Flats 417 allow deflectable post 440 to be engaged by a tool after hex extension 448 has been removed.

Referring again to FIG. 4A, a cap 410 is designed to perform multiple functions including securing retainer 442 in cavity 432 of bone anchor 420. Cap 410 has a central aperture 412 for receiving deflectable post 440. In the embodiment of FIG. 4A, cap 410 has surface features 414, for example splines or flutes, adapted for engagement by an implantation tool or mounting a component, e.g. an offset connector. Surface features 414 may be, for example, engaged by a driver that mates with surface features 414 for implanting bone anchor 400 in a bone. As shown in FIG. 4A, cap 410 comprises a cylindrical shield section 418 connected to a collar section 416. Shield section 418 is designed to mate with cavity 432 of housing 430. Shield section 418 is threaded adjacent collar section 416 in order to engage threads at the proximal end of cavity 432 of housing 430. The distal end of shield section 418 comprises a flange 419 for securing retainer 442 within cavity 432 of housing 430.

Bone anchor 400 is assembled prior to implantation in a patient. FIG. 4B shows a perspective view of bone anchor 400 as assembled. When assembled, deflectable post 440 is positioned through cap 410. Cap 410 is then secured to the threaded end of cavity 432 (see FIGS. 4A and 4C) of housing 430 of bone anchor 420. Cap 410 has surface features 414 for engagement by a wrench to allow cap 410 to be tightened to housing 430. For example, cap 410 may be hexagonal or octagonal in shape or may have splines and/or flutes and/or other registration elements. Cap 410 may alternatively or additionally be laser welded to housing 430 after installation. Cap 410 secures deflectable post 440 within cavity 432 of bone anchor 420. Deflectable post 440 extends out of housing 430 and cap 410 such that mount 444 is accessible for connection to a vertical rod. Bone anchor 400 is implanted in a bone in the configuration shown in FIG. 4B and prior to attachment of a vertical rod or other spinal rod. A special tool may be used to engage the surface features 414 of cap 410 during implantation of bone anchor 400 into a bone (See, e.g. FIGS. 13A-13D).

FIG. 4C shows a sectional view of a bone anchor 400. Retainer 442 fits into a hemispherical pocket 439 in the bottom of cavity 432 of housing 430. The bottom edge of cap 410 includes the curved flange 419 which secures ball-shaped retainer 442 within hemispherical pocket 439 while allowing ball-shaped retainer 442 to pivot and rotate. Accordingly, in this embodiment, a ball-joint is formed. FIG. 4C also illustrates deflection of deflectable post 440—dashed lines. Applying a force to mount 444 causes deflection of deflectable post 440 of bone anchor 400. Deflectable post 440 pivots about a pivot point 403 indicated by an X. Deflectable post 440 may pivot about pivot point 403 in any direction, as shown by arrow 450. Concurrently or alternatively, deflectable post 440 can rotate, as shown by arrow 452, about the long axis of deflectable post 440 (which also passes through pivot point 403). In this embodiment, pivot point 403 is located at the center of ball-shaped retainer 442. In a preferred embodiment, deflectable post 440 may deflect from 0.5 mm to 2 mm in any direction before making contact with limit surface 413. More preferably, deflectable post 440 may deflect approximately 1 mm before making contact with limit surface 413. After a fixed amount of deflection, deflectable post 440 comes into contact with limit surface 413 of cap 410. Limit surface 413 is oriented such that when deflectable post 440 makes contact with limit surface 413, the contact is distributed over an area to reduce stress on deflectable post 440. In this embodiment, the deflectable post 440 contacts the entire sloping side of the conically-shaped limit surface 413. In another embodiment, the deflectable post may only contact a limit ring that is located distally from the flange 419 of cap 410. After deflectable post 440 comes into contact with limit surface 413, further deflection requires deformation (bending) of deflectable post 440.

Figure 5A:
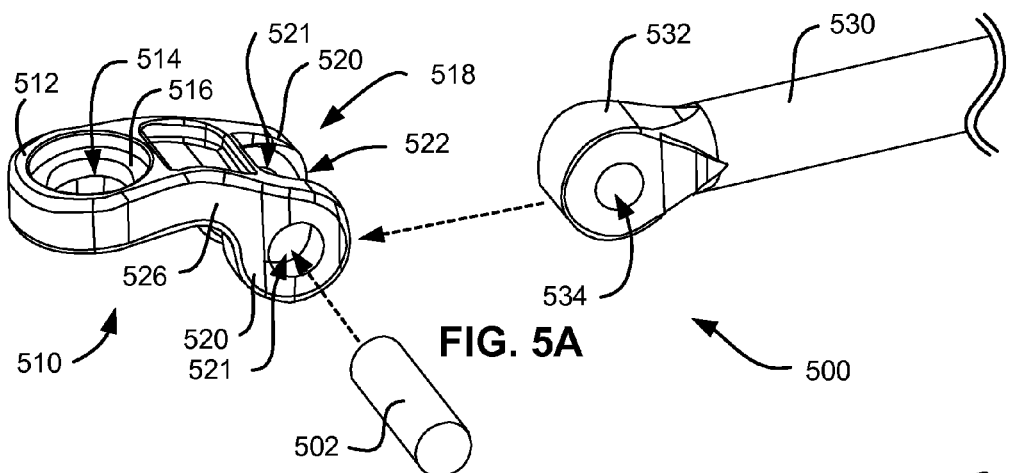
FIG. 5A shows an exploded view of an alternative spinal rod according to an embodiment of the invention.
Figure 5B:
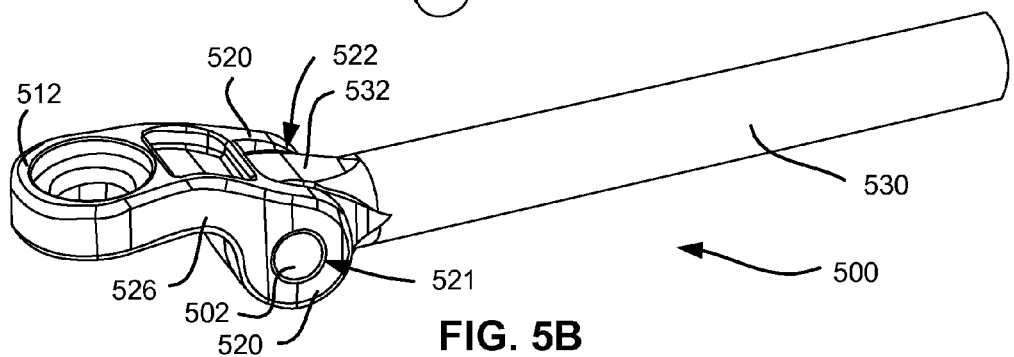
FIG. 5B shows a perspective view of the alternative spinal rod of FIG. 5A as assembled.
Figure 5C:
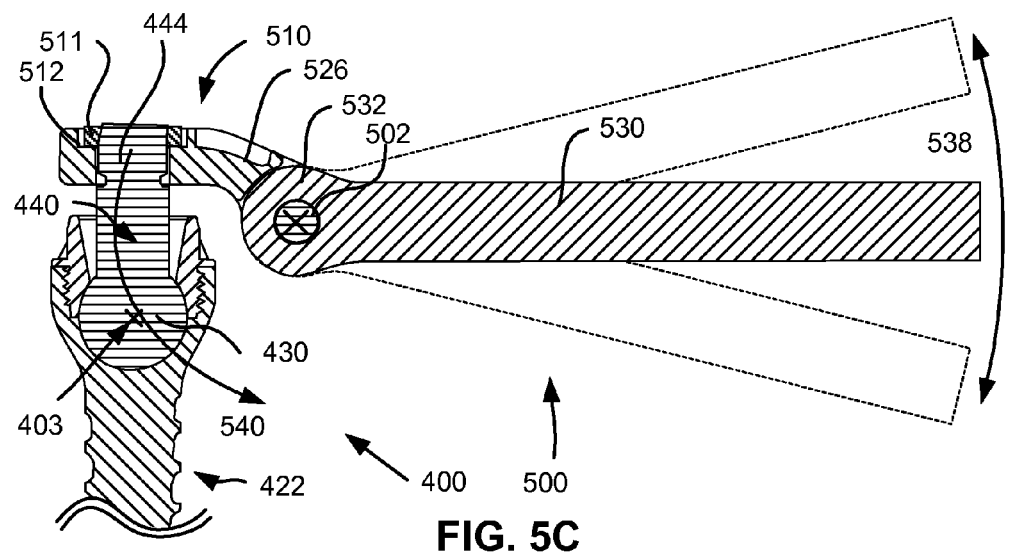
FIG. 5C shows a sectional view of the alternative spinal rod of FIG. 5A as assembled.
Figure 6A:
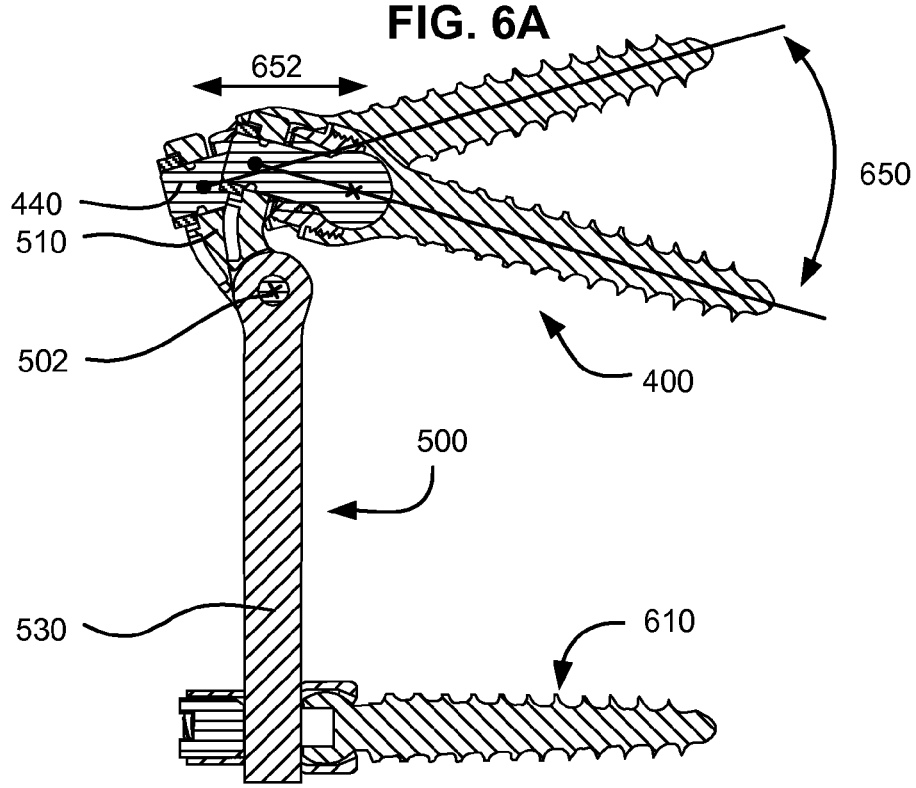
FIG. 6A illustrates an aspect of the kinematics of a spinal prosthesis incorporating the bone anchor of FIGS. 4A-4C and spinal rod of FIGS. 5A-5C according to an embodiment of the present invention.
Figure 6B:
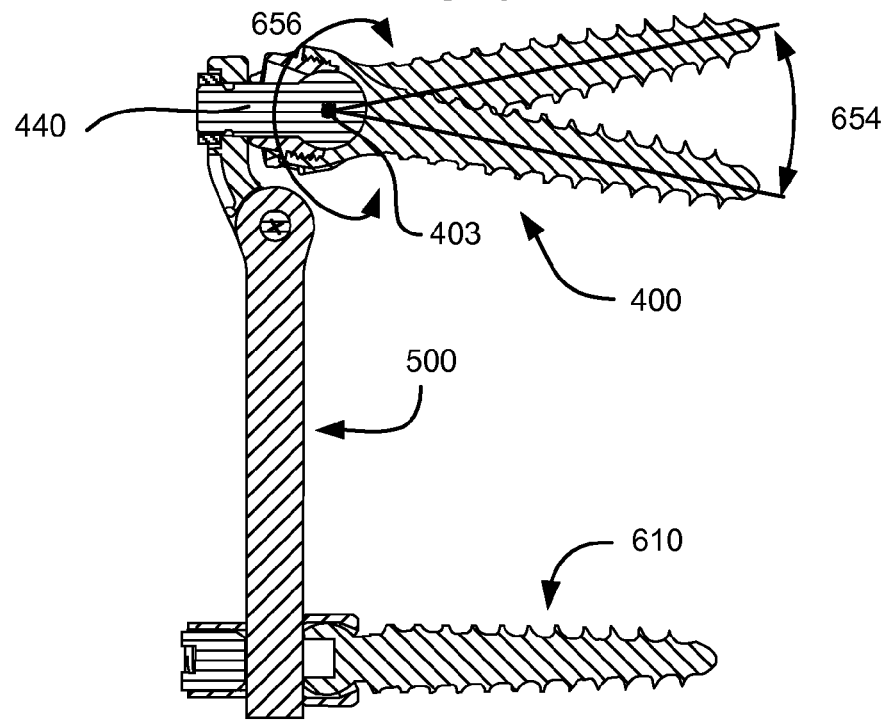
FIG. 6B illustrates an aspect of the kinematics of the spinal prosthesis of FIG. 6A.
Figure 6C:
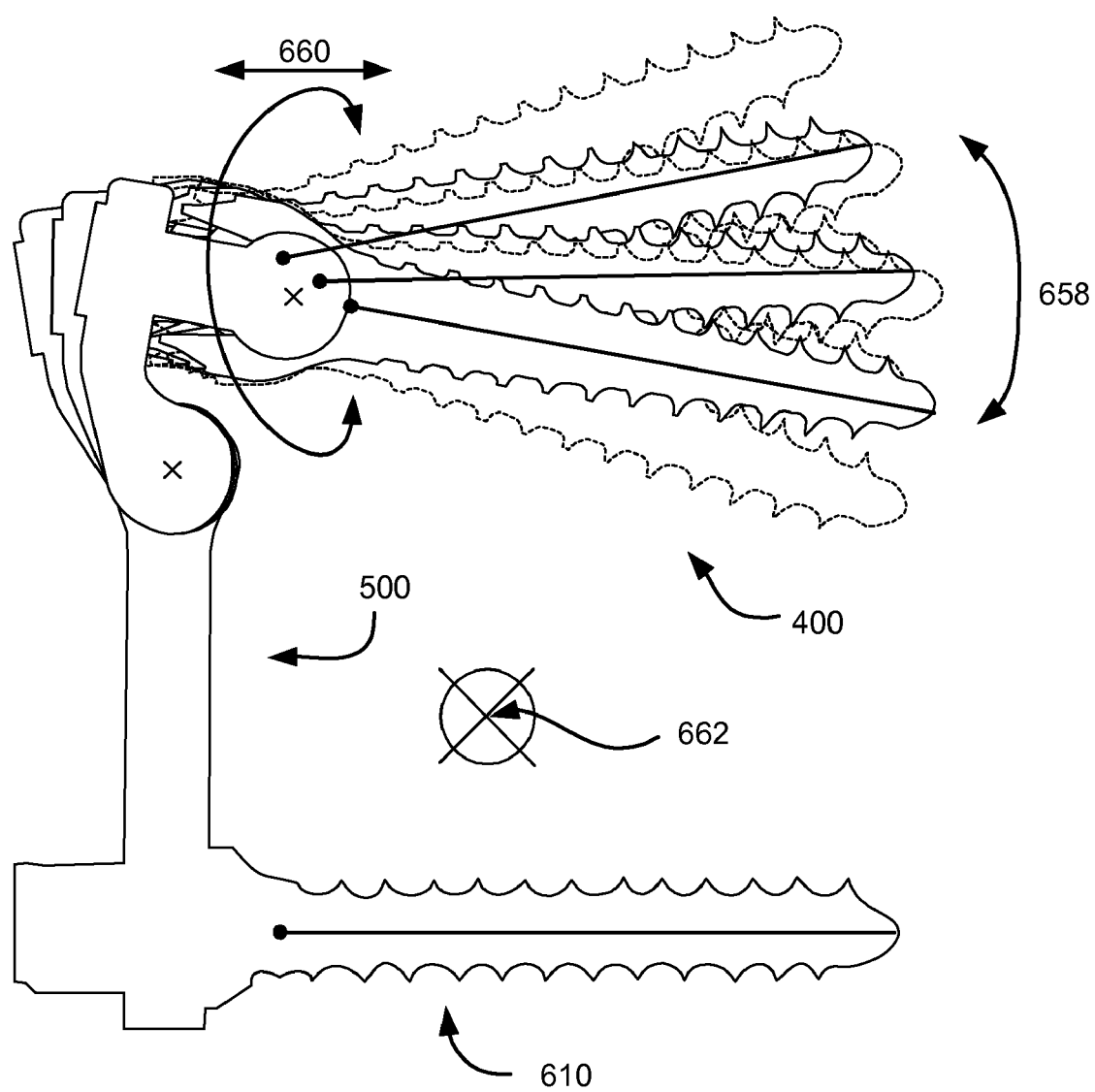
FIG. 6C illustrates an aspect of the kinematics of the spinal prosthesis of FIG. 6A.

FIGS. 5A-5C show exploded, perspective, and sectional views of an alternative embodiment of a compound spinal/vertical rod. Referring first to FIG. 5A, compound rod 500 includes a coupling 510 joined by a pin 502 to a rod 530. As shown in FIG. 5A, coupling 510 has a mount 512 at one end and a clevis 518 at the other end. Mount 512 is configured to be secured to a bone anchor. Mount 512 includes a bore 514 therethrough sized to receive the mount of a bone anchor (see e.g. mount 444 of FIGS. 4A and 4B). Bore 514 is in some embodiments configured to mate with the mount of a bone anchor to preclude rotation—for example by being polygonal in section. However, in alternative embodiments bore 514 is circular in section. Coupling 510 is adapted to be secured to a bone anchor using, for example a threaded nut. Coupling 510 is, in some embodiments, provided with a recess 516 to reduce the profile of a nut above coupling 510.

Coupling 510 is connected to clevis 518 by offset or dogleg connector 526. The dogleg connector 526, in addition to the other components, provides for enhanced motion of a spinal prosthesis so that the prosthesis can model the natural kinetics of the spine (See, e.g. FIG. 5C). Clevis 518 has two arms 520 separated by a slot 522. Each arm 520 has an aperture 521 for receiving pin 502. Slot 522 is size to receive a disc 532 formed at one end of rod 530. Disc 532 also has an aperture 534 for receiving pin 502. Thus rod 530 may rotate relative to coupling 510 about the axis of rotation of pin 502. The axis of rotation of pin 502, in this embodiment, is substantially perpendicular to the axis of bore 514 except that the pin axis is offset from the bore axis.

FIG. 5B shows compound rod 500 as assembled. Compound rod 500 is assembled prior to implantation in a patient. Disc 532 is placed in slot 522 between arms 520. Aperture 534 is aligned with apertures 521. Pin 502 is then inserted between arms 520, across slot 522 and through aperture 534 thereby securing disc 532 within slot 522. Pin 502 can be secured mechanically or bonded to clevis 518 by e.g. laser welding.

FIG. 5C shows a sectional view of compound rod 500 as assembled and mounted to the mount 444 of bone anchor 400 of FIGS. 4A-4C. As shown in FIG. 5C mount 512 of coupling 510 is secured to mount 444 of deflectable post 440 by a nut 511. Coupling 510 is also joined by pin 502 to rod 530. Mount 512 of coupling 510 has a bore 514 for receiving the mount 444 of a bone anchor 400. After assembly, rod 530 is free to pivot relative to coupling 510 around the axis of pin 502 as shown by arrow 538. Further, it is noted that the pivot pin 502 and the pivot axis is located to the side of the housing 430 and substantially perpendicular to and offset from the longitudinal axis of the threaded shaft 422 of the bone anchor 400. Further, the pivot pin 502 is located below the level where the compound rod 500 is connected to the deflectable post 440 of the bone anchor 400. The mount 444 and pin 502 are approximately equidistant from pin 502 of compound rod 500 and pivot about pivot point 403. However, dogleg connector 526 changes the position of pin 502 relative to mount 444. The shape of the dogleg connector 526 controls the angle between the mount 444 and pivot point 403 relative to pin 502 and thus can be designed to modulate the direction of movement of pivot point 403. The length of the dogleg connector controls the distance between the pin 502 and pivot point 403 and thus can be designed to modulate the amount of movement of pivot point 403 for a given amount of deflection of coupling 510. The kinematics of pivot point 403 enabled by pin 502 and dogleg connector 526 permits a spinal prosthesis to more closely approximate the natural kinematics of the spine by coupling rotation or coupling 510 with translation of pivot point 403 as shown by arrow 540.

Figure 5D:
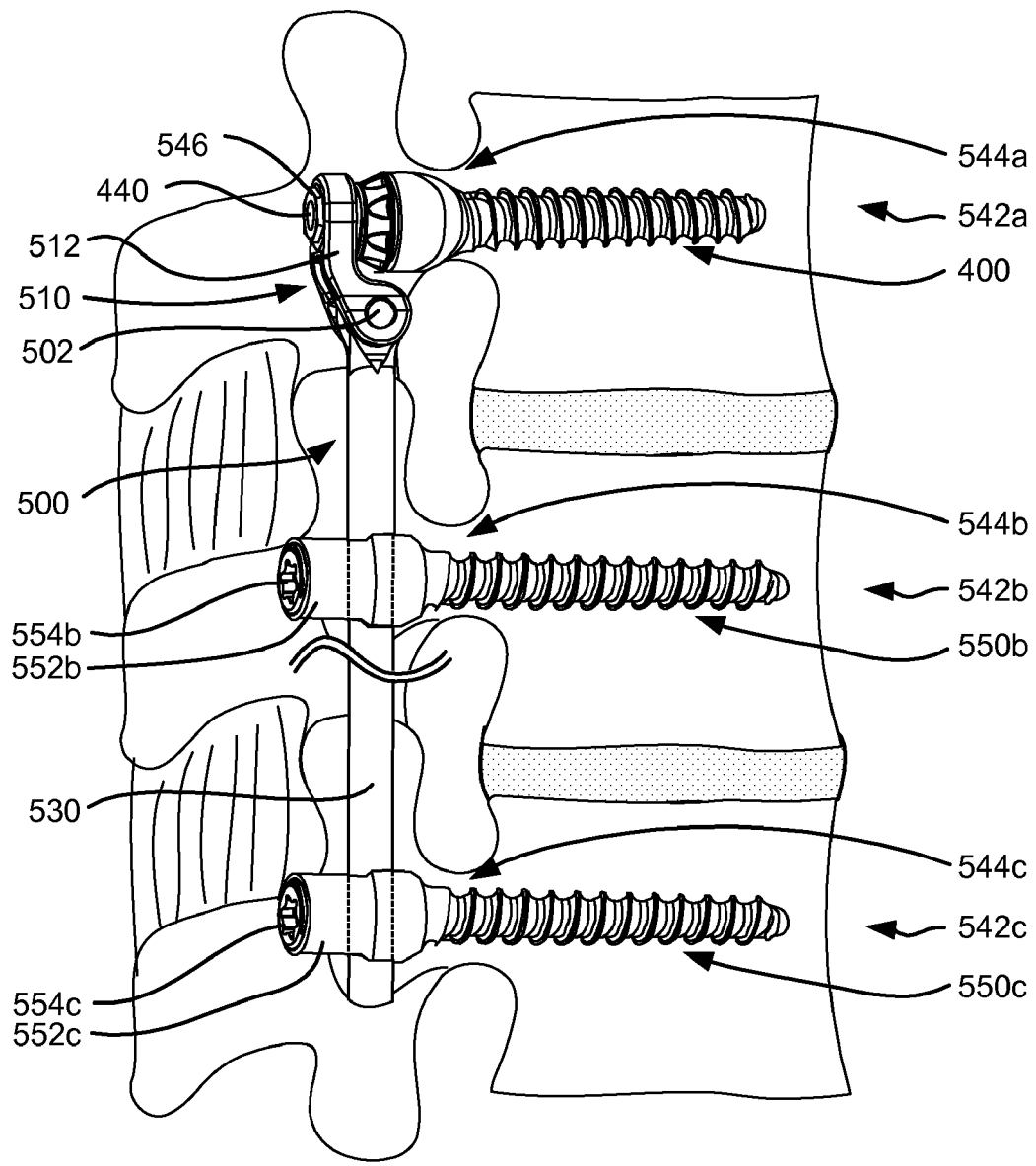
FIG. 5D shows a lateral of a spinal prosthesis incorporating the bone anchor of FIGS. 4A-4C and spinal rod of FIGS. 5A-5C according to an embodiment of the present invention.

FIG. 5D shows a lateral view of a spinal stabilization prosthesis 540 utilizing the bone anchor 400 of FIGS. 4A-4C in combination with the compound rod 500 of FIGS. 5A-5C. As shown in FIG. 5D, a spinal prosthesis 540 can be used to stabilize three vertebrae 542a, 542b, and 542c. Bone anchor 400 is implanted in pedicle 544a of vertebra 542a. Conventional pedicle screws 550b, 550c are implanted in pedicles 544b, 544c of vertebrae 542b, and 542c. Coupling 512 of compound rod 500 is secured to mount 444 of deflectable post 440 of bone anchor 400 by nut 546. Rod 530 is positioned in the heads 552b, 552c or pedicle screws 550b, 550c and secured with set screws 554b, 554c. The spinal stabilization prosthesis 540 secures vertebra 542b in fixed relationship to vertebra 542c and is suitable for posterior stabilization of fusion between vertebra 542b and 544c. Rod 530 is also in fixed relationship with vertebra 542b and 544c. Likewise pin 502 is in fixed relationship to rod 530. The spinal stabilization prosthesis permits controlled movement of vertebra 542a relative to 542b while providing load sharing. Controlled movement of vertebra 542a relative to vertebra 542b is enabled by pivoting of coupling 510 relative to rod 530 (see FIG. 5 C) in combination with pivoting and rotation of deflectable post 440 relative to bone anchor 420 (see FIG. 4 C).

In an alternative embodiment of a spinal prosthesis, a shorter rod 530 is used and compound rod 500 spans two vertebra from a bone anchor 400 to a single conventional pedicle screw implanted in an adjacent vertebra. Typically, identical or similar stabilization structures are implanted on each side of the spinal column. Furthermore, although compound rod 500 has been shown in combination with bone anchor 400 of FIGS. 4A-4C, compound rod 500 can, in other embodiments, be utilized with any other of the bone anchors having deflectable posts described herein.

The bone anchor 400 has a low profile. As a result, compound rod 500 is mounted closer to the surface of the vertebrae. Moreover, the shape of compound rod 500 places rod 530 several millimeters closer to the surface of the vertebrae. Often, the level of the vertical rod is used to guide the depth of placement of the pedicle screw in the adjacent vertebrae. Although the vertical rods can be bent by the surgeon to compensate for any height offset this process is technically difficult. Thus, the surgeons often prefer to arrange the various pedicle screws with the mounting points in alignment the vertical rod without bending. The low profile of bone anchor 400 and compound rod 500 allow conventional pedicle screw used in conjunction therewith to be mounted with all of threaded shaft implanted in the vertebra and head abutting the surface of the vertebra. This is the preferred location as it reduces stress on the vertebra and conventional pedicle screw by increasing the contact area between pedicle screw and vertebra and reducing the moment arm.

Thus, one of the advantages of bone anchor 400 of FIGS. 4A-4C is the low profile which causes less trauma to tissue and a better position of the system and better alignment with a pedicles screw fully implanted in an adjacent vertebra. The compound rod 500 of FIGS. 5A-5C enhances the low profile configuration which causes less trauma to tissue and a better position of the system and better alignment with a pedicles screw fully implanted in an adjacent vertebra. In a preferred embodiment the top of the cap of bone anchor 400 is approximately 10 mm above the surface of the vertebra when implanted and the proximal side (furthest from vertebrae) of rod 530 is approximately 11 mm above the surface of the vertebra. Also in the preferred embodiment the coupling 510 is no more than about 15 mm from the surface of the vertebrae when implanted.

FIGS. 6A-6C illustrate the kinetics of a spinal prosthesis 600 having a conventional pedicle screw 610 joined by a compound rod 500 to a bone anchor 400. As shown in FIG. 6A, coupling 510 of compound rod 500 is secured in fixed relationship to deflectable post 440. Coupling 510 and deflectable post 440 thus move as one unit. Likewise rod 530 is secured in fixed relationship to pedicle screw 610. Rod, 530 and pedicle screw 610 thus move as one unit. Bone anchor 400 can move in a controlled manner with respect to pedicle screw 610 by pivoting of coupling 510 (and deflectable post 440) relative to rod 530 (and pedicle screw 610) in combination with pivoting and rotation of bone screw 420 relative to deflectable post 440 (and coupling 510). In a preferred embodiment, the gap between the distal surface of rod 530 and a line joining the pedicle surface on adjacent vertebra is less than about 10 mm. More preferably the gap between the distal surface of rod 530 and a line joining the pedicle surface on adjacent vertebra is less than about 10 mm.

FIG. 6A shows the movement of bone screw 420 relative to pedicle screw 610 assuming no motion within bone anchor 400. As shown in FIG. 6A, bone screw 420 can pivot relative to pedicle screw 610 as shown by arrow 650. Bone screw 420 can move over a wide range of movement, e.g. ±90 degrees from parallel with pedicle screw 610. However, the axis of the rotation is the axis of pin 502 which is offset from the axis of bone screw 420 by a distance controlled by the length of coupling 510. The length and shape of coupling 510 causes pivoting of coupling 510 to produce pivoting of bone screw 420 and also net translation of bone screw 420 relative to pedicle screw 610 as shown by arrow 652.

FIG. 6B shows the movement of bone screw 420 relative to pedicle screw 610 assuming no motion within compound rod 500. As shown in FIG. 6B, bone screw 420 can pivot ±10 degrees from the axis of deflectable post 440 (and pedicle screw 610) as shown by arrow 654. The bone screw pivots about pivot point 403 within deflectable post 440. Bone screw 420 can also rotate around its long axis relative to deflectable post 440 as shown by arrow 656.

FIG. 6C is a simplified graph illustrate the combined kinetics enabled by bone anchor 400 when combined with compound rod 500. As shown in FIG. 6C, bone anchor 400 and compound rod 500, when combined, allow complex kinetics that more closely approximate the natural kinetics of the spine than either component alone. For example, as shown in FIG. 6C, spinal stabilization prosthesis 600 supports coupling of spinal flexion/extension (arrow 658) with dorsal-ventral translation (arrow 660). Moreover, spinal stabilization prosthesis 600 also supports movement of bone screw 420 about a natural center of rotation 662. Although not shown, spinal stabilization prosthesis 600 also supports coupling of other movement axes, for example, the coupling of lateral bending with axial rotation.

Figure 7A:
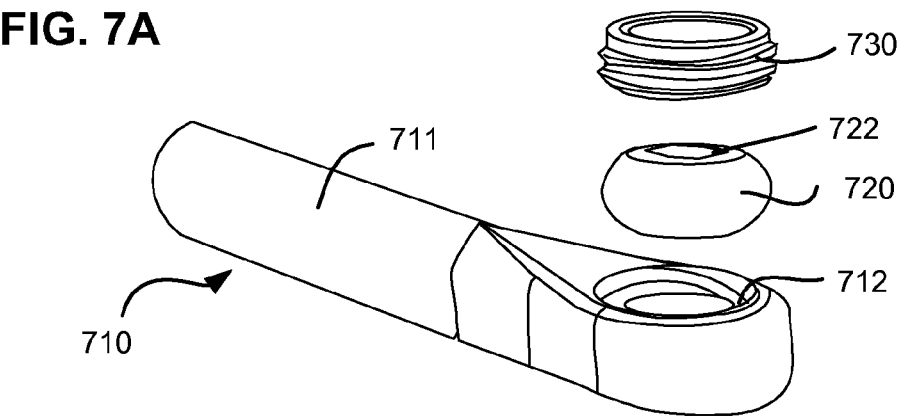
FIGS. 7A-7C show views of an alternative vertical rod.

FIG. 7A illustrates a preferred embodiment of a vertical rod 710 for use with deflection rod 300. As shown in FIG. 7A, vertical rod 710 comprises a rod 711 which is preferably a 5.5 mm diameter titanium rod. Vertical rod 710 has a pocket 712 at one end sized to receive a ball 720. Ball 720 is preferably a cobalt chrome ball. Ball 720 has a polygonal aperture 722 designed to closely engage the polygonal section 702 of mount 314. Ball 720 is inserted into pocket 712 and secured into place with threaded cap 730. Pocket 712 is threaded to receive cap 730. Ball 720 is placed in pocket 712 and then cap 730 is screwed into the threaded portion of pocket 712. Cap 730 is preferably titanium and may be laser welded or otherwise secured to vertical rod 710 after assembly. The components of vertical rod 710—titanium rod 711, titanium cap 730 and cobalt chrome ball 720 are assembled prior to use.

Figure 7B:
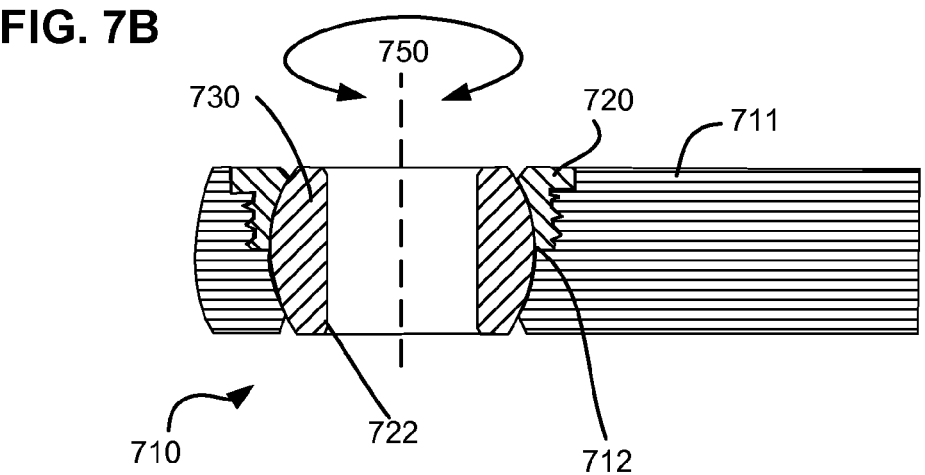
Figure 7C:
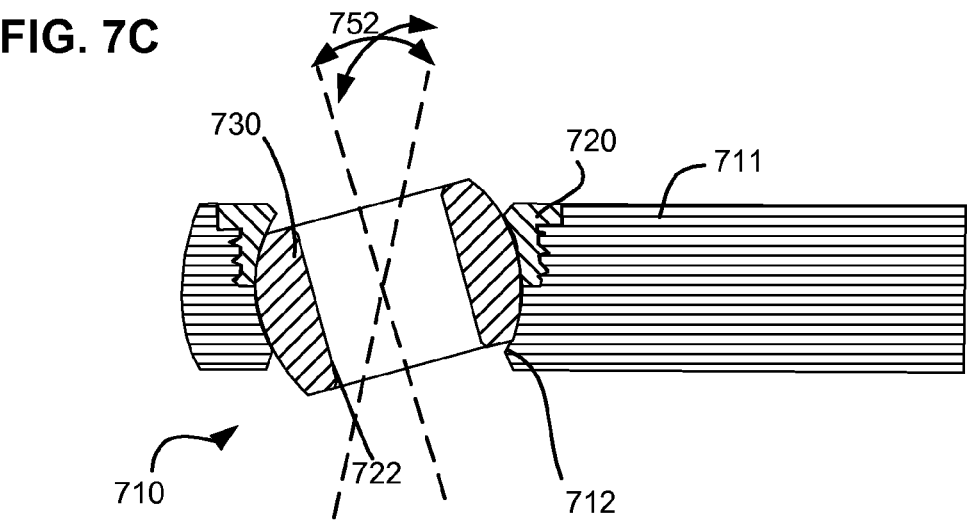

FIGS. 7B and 7C shows a sectional view through vertical rod 710. FIG. 7B shows ball 720 positioned within pocket 712 of rod 711. As shown in FIG. 7B cap 730 and pocket 712 capture ball 730 such that it cannot be removed from vertical rod 710. Ball 730 can, however, rotate 360 degrees around the axis of aperture 722 as shown by arrow 750. This allows vertical rod 710 to rotate 360 degrees around the long axis of the deflection rod or bone anchor to which ball 730 is mounted. Ball 730 can also tilt from the position shown in FIG. 7B as shown in FIG. 7C by arrows 752. In a preferred embodiment ball 730 can tilt 7 degrees in any direction therefore allowing vertical rod 710 to tilt 7 degrees from perpendicular relative to the deflection rod or bone anchor to which ball 730 is mounted. Note that the mount 314 and a nut to secure the vertical rod 710 to mount 314 are designed so not as to interfere with the range of motion either in rotation or tilting (See FIG. 3A).

Vertical rod 710 may be used with a standard bone anchor, a deflection rod and bone anchor (for example bone anchor 320 and deflection rod 300 of FIG. 3A), or a polyaxial screw. Likewise, the assembly of deflection rod 300 and bone anchor 320 of FIG. 3A may be utilized with vertical rod 710, but may also be utilized in conjunction with a vertical rod not having a ball joint.

Alternative Bone Anchor and Compound Spinal Rod

FIGS. 8A-8D illustrate another alternative bone anchor 800. FIG. 8A shows an exploded view of bone anchor 800. FIG. 8B shows a perspective view of bone anchor 800, as assembled. FIG. 8C shows a sectional view of bone anchor 800. FIG. 8D illustrates deflection of the deflectable post of bone anchor 800.

Referring first to FIG. 8A, bone anchor 800 includes, in this embodiment, four components: bone screw 820, deflectable post 840, centering rod 860, and cap 810. Bone screw 820 comprises a threaded shaft 822 with a housing 830 at one end. Housing 830 may in some embodiments be cylindrical as previously described and is in some embodiments provided with splines/flutes. Housing 830 is preferably formed in one piece with threaded shaft 822. Housing 830 has a cavity 832 oriented along the axis of threaded shaft 822. Cavity 832 is open at the proximal end of housing 830 and is configured to receive deflectable post 840.

Centering rod 860 is, in a preferred embodiment, a cylindrical rod made of a superelastic metal—for example nitinol. The proximal end 862 of centering rod 860 is sized and configured to be received within deflectable post 840. The distal end 864 of centering rod 860 is sized and configured to be received within bone screw 820. In a preferred embodiment both centering rod 860 is cylindrical in shape. However, in alternative embodiments, the proximal end 862 and distal end of rod 860 may have other than a circular section, for example, square, oval, rectangular, or other polygonal. Note that the distal end 864 and proximal end 862 of centering rod 860 can have the same, or different, sectional shapes. The center section 866 of centering rod 860 is designed to bend in response to deflection of deflectable post 840 relative to bone screw 820 and exert a restorative centering force upon deflectable post 840. The restorative force tends to align the longitudinal axis of the deflectable post 840 with the longitudinal axis of the bone screw 820. The force increases as the angle between the deflectable post 840 and bone screw 820 increases. The diameter and shape of center section 866 of centering rod 860 can be designed/selected to achieve a desired restorative force for a given deflection. Center section 866 can be cylindrical but may have other than a circular section, for example, square, oval, rectangular, or other polygonal. The force/deflection response can accordingly be isotropic or anisotropic depending upon the shape of center section 866. In one embodiment, centering rod 860 is a superelastic nitinol wire having a diameter between 0.060 and 0.080 inches. In an exemplary embodiment centering rod is a superelastic nitinol wire having a diameter of 0.063 inches.

A hemispherical pocket 839 (shown by dashed lines) is formed in the bottom of cavity 832 of housing 830. A bore 834 extends distally from the bottom of hemispherical pocket 839 along the longitudinal axis of bone screw 820. Bore 834 is sized and configured to receive the distal end 864 of centering rod 860. Bore 834 is chamfered where it meets hemispherical pocket 839 to allow for bending of centering rod 860. In a preferred embodiment both centering rod 860 and bore 834 are cylindrical in shape such that the distal end 864 of centering rod 860 may rotate about its longitudinal axis within bore 834. However, in alternative embodiments, the distal end 864 of rod 860 and bore 834 may have other than a circular section, for example, square, oval, rectangular, or other polygonal.

In a preferred embodiment, deflectable post 840 is a titanium post 5 mm in diameter. Deflectable post 840 is alternatively made of cobalt chrome. Deflectable post 840 has a retainer 842 at one end. At the other end of deflectable post 840 is a mount 844. Retainer 842 is a ball-shaped or spherical structure in order to form part of a linkage connecting deflectable post 840 to bone screw 820. Mount 844 is a low profile mount configured to connect deflectable post 840 to a vertical rod component (not shown, but see, e.g. FIGS. 5A-5C).

Mount 844 comprises a threaded cylinder 846 to which the vertical rod component may be secured. Mount 844 in some embodiments also comprises a polygonal section 845 to prevent rotation of a component relative to mount 844.

A bore 870 (show by dashed lines) extends proximally from the bottom of ball-shaped retainer 842 along the longitudinal axis of deflectable post 840. Bore 870 includes a proximal bore 872 sized and configured to receive the proximal end 862 of centering rod 860. Bore 870 has a larger distal bore 876. Distal bore 876 is sized to allow bending of centering rod 860 and deflection of deflectable post 840. In some embodiments, distal bore 876 is sized such that center section 866 does not contact the sides of distal bore 876 over the full range of motion of deflectable post 840. In alternative embodiments, distal bore 876 is sized and shaped such that center section 866 comes into contact progressively with the sides of distal bore 876 over the range of motion of deflectable post 840 thereby modulating the centering force. Distal bore 876 is chamfered where it intersects the surface of retainer 842. In a preferred embodiment both centering rod 860 and proximal bore 872 are cylindrical in shape such that the proximal end 862 of centering rod 860 may rotate about its longitudinal axis within proximal bore 872. However, in alternative embodiments, the proximal end 862 of rod 860 and proximal bore 872 may have other than a circular section, for example, square, oval, rectangular, or other polygonal. Note that the distal end 864 and proximal end 862 of centering rod 860 can have the same, or different, sectional shapes.

On the proximal end of deflectable post 840 is a mount 844 for connecting deflectable post 840 to a vertical rod or other component. Mount 844 includes a male hex extension 848 which may be engaged by a tool to hold stationary mount 844 during attachment to a vertical rod. At the proximal end of male hex extension is a nipple 849 for securing male hex extension 848 into a tool. Hex extension 848 is breakaway component. Between hex extension 848 and threaded cylinder 846 is a groove 847. Groove 847 reduces the diameter of deflectable post 840 such that hex extension 848 breaks away from threaded cylinder 846 when a desired level of torque is reached during attachment of a vertical rod. The breakaway torque is determined by the diameter of remaining material and the material properties. In a preferred embodiment the breakaway torque is approximately 30 foot pounds. Thus, hex extension 848 breaks away during implantation and is removed. Nipple 849 is engaged by the tool in order to remove hex extension 848. Deflectable post 840 is also provided with a pair of flats 843 immediately adjacent mount 844. Flats 843 allow deflectable post 840 to be engaged by a tool if necessary after hex extension 848 has been removed (for example to disconnect a vertical rod during revision of the implant).

Referring again to FIG. 8A, a cap 810 is designed to perform multiple functions including securing retainer 842 in cavity 832 of bone screw 820. Cap 810 has a central aperture 812 for receiving deflectable post 840. In the embodiment of FIG. 8A, cap 810 has surface features 814, for example splines or flutes, adapted for engagement by an implantation tool or mounting a component, e.g. an offset connector. Surface features 814 may be, for example, engaged by a driver that mates with surface features 814 for implanting bone anchor 800 in a bone. As shown in FIG. 8A, cap 810 comprises a cylindrical shield section 818 connected to a collar section 816. Shield section 818 is designed to mate with cavity 832 of housing 830. Shield section 818 is threaded adjacent collar section 816 in order to engage threads at the proximal end of cavity 832 of housing 830. The distal end of shield section 818 comprises a curved flange 819 for securing retainer 842 within cavity 832 of housing 830.

Bone anchor 800 is assembled prior to implantation in a patient. FIG. 8B shows a perspective view of bone anchor 800 as assembled. During assembly, centering rod 860 (not shown) is received in bore 870 and bore 834. As bore 870 and bore 834 are closed, it is not necessary to attach centering rod 860 to either of deflectable post 840 or bone screw 820. However, if desirable centering rod 860 can be attached to either or both of deflectable post 840 or bone screw 820 by mechanical means (e.g. pins), welding or other fastening mechanism. Retainer 842 (not shown) is received in hemispherical pocket 839 (not shown). Deflectable post 840 is then positioned through cap 810. Cap 810 is then secured to the threaded end of cavity 832 (see FIGS. 8A and 8C) of housing 830 of bone screw 820. Cap 810 has surface features 814 for engagement by a wrench to allow cap 810 to be tightened to housing 830. For example, cap 810 may be hexagonal or octagonal in shape or may have splines and/or flutes and/or other registration elements. Cap 810 may alternatively or additionally be laser welded to housing 830 after installation. Cap 810 secures retainer 842 within cavity 832 of bone screw 820. Deflectable post 840 extends out of housing 830 and cap 810 such that mount 844 is accessible for connection to a vertical rod. Bone anchor 800 is implanted in a bone in the configuration shown in FIG. 8B and prior to attachment of a vertical rod or other spinal rod. A special tool may be used to engage the surface features 814 of cap 810 during implantation of bone anchor 800 into a bone (See, e.g. FIGS. 13A-13D).

FIG. 8C shows a sectional view of a bone anchor 800 after assembly. Retainer 842 fits into a hemispherical pocket 839 in the bottom of cavity 832 of housing 830. The bottom edge of cap 810 includes the curved flange 819 which secures ball-shaped retainer 842 within hemispherical pocket 839 while allowing ball-shaped retainer 842 to pivot and rotate. Accordingly, in this embodiment, a ball-joint is formed. Deflectable post 840 pivots about a pivot point 803 indicated by an X. In a preferred embodiment the pivot point 803 is positioned on the center of the section of centering rod 860. Deflectable post 840 may pivot about pivot point 803 in any direction, as shown by arrow 850. Concurrently or alternatively, deflectable post 840 can rotate, as shown by arrow 852, about the long axis of deflectable post 840 (which also passes through pivot point 803).

As shown in FIG. 8C, distal end 864 of centering rod 860 is received within bore 834 of bone screw 820. Proximal end 862 of centering rod 860 is received within proximal bore 872 of deflectable post 840. Center section 866 of centering rod 860 is received within distal bore 876 of bone screw 820. Note that an annular cavity 874 exists around center section 866 leaving center section free to flex when deflectable post 840 pivots about pivot point 803.

FIG. 8D illustrates deflection of deflectable post 840—dashed lines. Applying a force to mount 844 causes deflection of deflectable post 840 of bone anchor 800. Deflectable post 840 pivots about pivot point 803 located at the center of ball-shaped retainer 842. Proximal end 862 of centering rod 860 remains aligned with deflectable post 840 whereas distal end 864 remains aligned with bone screw 820. Thus center section 866 of centering rod 860 bends elastically in response to deflection of deflectable post 840. Centering rod 860 thus applies a centering force upon deflectable post 840 pushing back into alignment with bone screw 820. The magnitude of the force increases as the deflection increases. The magnitude of the force can be selected based on the configuration and material of centering rod 860. For example a larger diameter cylindrical nitinol rod will provide a larger centering force than a smaller diameter rod for the same amount of deflection.

Note that, in this embodiment, distal bore 876 is sufficiently large that center section 866 of centering rod 860 does not contact the sides of distal bore 876 over the range of deflection of deflectable post 840 as limited by contact with limit surface 813 of cap 810.

In a preferred embodiment, deflectable post 840 may deflect from 0.5 mm to 2 mm in any direction before making contact with limit surface 813. More preferably, deflectable post 840 may deflect approximately 1 mm before making contact with limit surface 813. After a fixed amount of deflection, deflectable post 840 comes into contact with limit surface 813 of cap 810. Limit surface 813 is oriented such that when deflectable post 840 makes contact with limit surface 813, the contact is distributed over an area to reduce stress on deflectable post 840. In this embodiment, the deflectable post 840 contacts the entire sloping side of the conically-shaped limit surface 813. After deflectable post 840 comes into contact with limit surface 813, further deflection requires deformation (bending) of deflectable post 840. Bending of deflectable post 840 requires significantly more force than bending of centering rod 860.

Moving contact between centering rod 860 and deflectable post 840 can cause wearing of the surface of the deflectable post 840 and/or centering rod 860. FIG. 8E illustrates an optional component which can be incorporated into deflectable post 840 to reduce such wear. FIG. 8E shows a sleeve 878 designed to fit within bore 870 (see FIG. 8A) of deflectable post 840. Sleeve 878 forms an intermediate layer between deflectable post 840 and centering rod 860. Sleeve 878 is made of a material which protects centering rod 860 and deflectable post 840 from wear during moving contact. In a preferred embodiment, sleeve 878 is made of cobalt chrome or PEEK, however, other biocompatible wear resistant materials and/or coatings can be used. Deflectable post 840 can be made, for example of cobalt chrome, titanium, titanium alloy and/or titanium coated with cobalt chrome.

FIG. 8F shows a sectional view of a bone anchor 800*f* which includes sleeve 878 of FIG. 8E. Sleeve 878 is placed into bore 870 of deflectable post 840 prior to assembly with housing 830. Sleeve 878 can be press fit into bore 870 and/or can be secured within bore 870 using conventional mechanical or bonding techniques suitable for the material used. As shown in FIG. 8F, distal end 864 of centering rod 860 is received within bore 834 of bone screw 820. Proximal end 862 of centering rod 860 is received within proximal bore 872 of deflectable post 840. Sleeve 878 is positioned between deflectable post 840 and the walls of bore 870. Center section 866 of centering rod 860 is received within distal bore 876 of bone screw 820. Note that an annular cavity 874 exists around center section 866 between center section 866 and sleeve 878 leaving center section 866 free to flex when deflectable post 840 pivots about pivot point 803. As previously described, retainer 842 fits into a hemispherical pocket 839 in the bottom of cavity 832 of housing 830. The bottom edge of cap 810 includes the curved flange 819 which secures ball-shaped retainer 842 within hemispherical pocket 839 while allowing ball-shaped retainer 842 to pivot and rotate.

Deflectable post 840 pivots about a pivot point 803 indicated by an X. In a preferred embodiment the pivot point 803 is positioned on the center of the section of centering rod 860. Deflectable post 840 may pivot about pivot point 803 in any direction. Concurrently or alternatively, deflectable post 840 can rotate about the long axis of deflectable post 840 (which also passes through pivot point 803). As shown in FIG. 8F, sleeve 878 is positioned between centering rod 860 and the walls of bore 870 of deflectable post 840 such that if there is moving contact between the parts during deflection and/or rotation, the parts are protected from wear.

FIGS. 9A-9D illustrate another alternative bone anchor 900. FIG. 9A shows an exploded view of bone anchor 900. FIG. 9B shows a perspective view of bone anchor 900, as assembled. FIG. 9C shows a sectional view of bone anchor 900. FIG. 9D illustrates deflection of the deflectable post of bone anchor 900.

Referring first to FIG. 9A, bone anchor 900 includes, in this embodiment, four components: bone screw 920, deflectable post 940, centering rod 960, and cap 910. Bone screw 920 comprises a threaded shaft 922 with a housing 930 at one end. Housing 930 is provided with tool engagement features 936 which are adapted to be engaged by a wrench (not shown) to drive threaded shaft 922 into a bone. Housing 930 is preferably formed in one piece with threaded shaft 922. Housing 930 has a cavity 932 oriented along the axis of threaded shaft 922. Cavity 932 is open at the proximal end of housing 930 and is configured to receive deflectable post 940.

Centering rod 960 is, in a preferred embodiment, a cylindrical rod made of a superelastic metal—for example nitinol. The proximal end 962 of centering rod 960 is sized and configured to be received within deflectable post 940. The distal end 964 of centering rod 960 is sized and configured to be received within bone screw 920. In a preferred embodiment both ends of centering rod 960 are cylindrical in shape. However, in alternative embodiments, the proximal end 962 and distal end of rod 960 may have other than a circular section, for example, square, oval, rectangular, or other polygonal. Note that the distal end 964 and proximal end 962 of centering rod 960 can have the same, or different, sectional shapes. The center section 966 of centering rod 960 is designed to bend in response to deflection of deflectable post 940 relative to bone screw 920 and exert a restorative centering force upon deflectable post 940. The restorative force tends to align the longitudinal axis of the deflectable post 940 with the longitudinal axis of the bone screw 920. The force increases as the angle between the deflectable post 940 and bone screw 920 increases. The diameter and shape of center section 966 of centering rod 960 can be designed/selected to achieve a desired restorative force for a given deflection. Center section 966 can be cylindrical but may have other than a circular section, for example, square, oval, rectangular, or other polygonal. The force/deflection response can accordingly be isotropic or anisotropic depending upon the shape of center section 966. In one embodiment, centering rod 960 is a superelastic nitinol wire having a diameter between 0.060 and 0.080 inches. In an exemplary embodiment centering rod is a superelastic nitinol wire having a diameter of 0.063.

In one embodiment, centering rod 960 is 0.063 inch diameter nitinol wire.

A hemispherical pocket 939 (shown by dashed lines) is formed in the bottom of cavity 932 of housing 930. A bore 934 (shown by dashed lines) extends distally from the bottom of hemispherical pocket 939 along the longitudinal axis of bone screw 920. Bore 934 is sized and configured to receive the distal end 964 of centering rod 960. Bore 934 is chamfered where it meets hemispherical pocket 939 to allow for bending of centering rod 960. In a preferred embodiment both centering rod 960 and bore 934 are cylindrical in shape such that the distal end 964 of centering rod 960 may rotate about its longitudinal axis within bore 934.

Deflectable post 940 is a post 5 mm in diameter. Deflectable post 940 can be made, for example, from cobalt chrome or titanium. Deflectable post 940 has a retainer 942 at the distal end. Retainer 942 is a ball-shaped or spherical structure in order to form part of a linkage connecting deflectable post 940 to bone screw 920. At the proximal end of deflectable post 940 is a mount 944. Mount 944 is a low profile mount configured to connect deflectable post 940 to a vertical rod component (not shown, but see, e.g. FIGS. 5A-5C). Mount 944 comprises a threaded section 946 to which the vertical rod component may be secured. Mount 944 has at the proximal end a socket 949 which can be engaged by a wrench during the securing of a vertical rod to mount 944.

A bore 970 (show by dashed lines) extends proximally from the bottom of ball-shaped retainer 942 along the longitudinal axis of deflectable post 940. Bore 970 includes a proximal bore 972 sized and configured to receive the proximal end 962 of centering rod 960. Bore 970 has a larger distal bore 976. Distal bore 976 is sized to allow bending of centering rod 960 and deflection of deflectable post 940. In some embodiments, distal bore 976 is sized such that center section 966 does not contact the sides of distal bore 976 over the full range of motion of deflectable post 940. In alternative embodiments, distal bore 976 is sized and shaped such that center section 966 comes into contact progressively with the sides of distal bore 976 over the range of motion of deflectable post 940 thereby modulating the centering force. Distal bore 976 is chamfered where it intersects the surface of retainer 942. In a preferred embodiment both centering rod 960 and proximal bore 972 are cylindrical in shape such that the proximal end 962 of centering rod 960 may rotate about its longitudinal axis within proximal bore 972.

Referring again to FIG. 9A, a cap 910 is designed to perform multiple functions including securing retainer 942 in cavity 932 of bone screw 920. Cap 910 has a central aperture 912 for receiving deflectable post 940. As shown in FIG. 9A, cap 910 comprises a cylindrical shield section 918 connected to a collar section 916. Shield section 918 is designed to mate with cavity 932 of housing 930. The distal end of shield section 918 comprises a curved flange 919 for securing retainer 942 within cavity 932 of housing 930. Shield section 918 is threaded adjacent collar section 916 in order to engage threads at the proximal end of cavity 932 of housing 930. Cap 910 can be provided with surface features for engagement by tool during attachment of cap 910 to housing 930. For example, cap 910 may be hexagonal or octagonal in shape or may have splines, sockets and/or flutes and/or other registration elements.

Bone anchor 900 is assembled prior to implantation in a patient. FIG. 9B shows a perspective view of bone anchor 900 as assembled. During assembly, centering rod 960 (shown by dashed lines) is received in bore 970 and bore 934 (see FIGS. 9A and 9C). Because bore 970 and bore 934 are closed, it is not necessary to attach centering rod 960 to either of deflectable post 940 or bone screw 920. However, if desired, centering rod 960 can be attached to either or both of deflectable post 940 or bone screw 920 by mechanical means (e.g. pins), welding or other fastening method/device. Retainer 942 (not shown) is received in hemispherical pocket 939 (not shown). Deflectable post 940 is then positioned through aperture 912 of cap 910. Cap 910 is then secured to the threaded end of cavity 932 (see FIGS. 9A and 9C) of housing 930 of bone screw 920. Cap 910 may alternatively or additionally be laser welded to housing 930 after installation. Cap 910 secures retainer 942 within cavity 932 of bone screw 920. Deflectable post 940 extends out of housing 930 and cap 910 such that mount 944 is accessible for connection to a vertical rod. Bone anchor 900 is typically implanted in a bone in the configuration shown in FIG. 9B and prior to attachment of a vertical rod or other spinal rod. A special tool may be used to engage the surface features 936 of housing 930 during implantation of bone anchor 900 into a bone (See, e.g. FIGS. 13A-13D).

FIG. 9C shows a sectional view of a bone anchor 900 after assembly. Retainer 942 fits into a hemispherical pocket 939 in the bottom of cavity 932 of housing 930. The distal edge of cap 910 includes the curved flange 919 which secures ball-shaped retainer 942 within hemispherical pocket 939 while allowing ball-shaped retainer 942 to pivot and rotate. Accordingly, in this embodiment, a ball-joint is formed. Deflectable post 940 pivots about a pivot point 903 indicated by an X. In a preferred embodiment the pivot point 903 is positioned on the center of the section of centering rod 960 (at least when the longitudinal axis of the deflectable post 940 and bone screw 920 are aligned). Deflectable post 940 may pivot about pivot point 903 in any direction, as shown by arrow 950. Concurrently or alternatively, deflectable post 940 can rotate, as shown by arrow 952, about the long axis of deflectable post 940 (which also passes through pivot point 903).

As shown in FIG. 9C, distal end 964 of centering rod 960 is received within bore 934 of bone screw 920. Proximal end 962 of centering rod 960 is received within proximal bore 972 of deflectable post 940. Center section 966 of centering rod 960 is received within distal bore 976 of deflectable post 940. Note that an annular cavity 974 exists around center section 966 leaving center section 966 free to flex when deflectable post 940 pivots about pivot point 903.

Where flexible components are incorporated in a spinal device, one important consideration is the possibility of failure of the flexible element during the life of the device. One advantage of the present design of bone anchor 900 is that the centering rod 960 is not relied upon for securing mount 944 to bone screw. 920. Thus, if centering rod 960 fails at some point, mount 944 and any spinal components connected to it remain attached to bone screw 920. Thus it is an advantage of the present design of bone anchor 900 that, the failure mode for the "flexible element" of this design is fundamentally safe.

It is also advantageous that, in the present design centering rod 960 is fully enclosed within bore 970 and bore 934. Thus, where centering rod 960 is nitinol, the nitinol is not in direct contact with tissues of the body. Furthermore, even if centering rod 960 fails, no parts of centering rod 960 can migrate past ball 942 into the tissues surrounding bone anchor 900. Thus it is an advantage of the present design of bone anchor 900 that the flexible nitinol element is entirely enclosed within the device and not exposed to contact with tissues.

FIG. 9D shows a sectional view of bone anchor 900 and illustrates deflection of deflectable post 940. Applying a force to mount 944 causes deflection of deflectable post 940 of bone anchor 900. Deflectable post 940 pivots about pivot point 903 located at the center of ball-shaped retainer 942. Proximal end 962 of centering rod 960 remains aligned with deflectable post 940 whereas distal end 964 remains aligned with bone screw 920. Thus center section 966 of centering rod 960 bends elastically in response to deflection of deflectable post 940. Centering rod 960 thus applies a centering force upon deflectable post 940 pushing it back into alignment with bone screw 920. The magnitude of the force increases as the deflection increases. The magnitude of the force can be selected based on the configuration and material of centering rod 960. For example a larger diameter cylindrical nitinol rod will provide a larger centering force than a smaller diameter rod for the same amount of deflection. In a preferred embodiments centering rod 960 is floating, that is to say that it is not fixed to one or both of deflectable post 940 and bone screw 920. Thus, upon deflection of deflectable post 940, centering rod 960 can slide somewhat in one or both of proximal bore 972 and bore 934 such that the centering rod 960 is not placed under longitudinal tension during deflection of deflectable post 940.

In a preferred embodiment, deflectable post 940 may deflect from 0.5 mm to 2 mm in any direction before making contact with limit surface 913. More preferably, deflectable post 940 may deflect approximately 1 mm before making contact with limit surface 913. After a fixed amount of deflection, deflectable post 940 comes into contact with limit surface 913 of cap 910. Limit surface 913 is oriented such that when deflectable post 940 makes contact with limit surface 913, the contact is distributed over an area to reduce stress on deflectable post 940. In this embodiment, the deflectable post 940 contacts the entire sloping side of the conically-shaped limit surface 913. After deflectable post 940 comes into contact with limit surface 913, further deflection requires deformation (bending) of deflectable post 940. Bending of deflectable post 940 requires significantly more force than bending of centering rod 960.

As previously stated, the deflection/force response of a centering rod (and a ball-joint incorporating such a centering rod) can be customized based on the choice of design, dimensions and materials. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine for providing in a kit for a doctor to use. After a selected amount of deflection a deflectable post (see e.g. deflectable post 940 of FIGS. 9A-9D) will make contact with a limit surface (for example 1 mm of deflection. Further deflection then requires bending of the deflectable post 940. The deflectable post 940 therefore responds more stiffly as the load increases. As the deflection increases, the stiffness of the deflectable post 940 to further deflection is increased such that the force required per unit of additional deflection increases in response to the load placed on the spine and deflection rod.

Initially, as load or force is first applied to the deflectable post by the spine, the deflection of the deflectable post rod responds about linearly to the increase in the load. After the post makes contact with the limit surface, the deflection rod responds more stiffly. In this region, a greater amount of load or force needs to be placed on the deflection rod in order to obtain the same amount of deflection that was realized prior to this point. Accordingly, the deflectable post of this example provides a range of motion where the load supported increases about linearly as the deflection increases and then with increased deflection the load supported increases more rapidly in a non-linear manner. The transition from lower stiffness to higher stiffness region depends upon the distance between the deflectable post and the limit surface of the cap. This distance may be customized as previously described so that the transition occurs after the desired amount of deflection, for example after about 1 mm of deflection or after about 2 mm of deflection.

Referring again to FIG. 9D, note that, in this embodiment, distal bore 976 is sufficiently large that center section 966 of centering rod 960 does not contact the sides of distal bore 976 over the range of deflection of deflectable post 940 as limited by contact with limit surface 913 of cap 910. FIG. 9E shows an alternative embodiment in which the distal bore 976e makes contact with centering rod 960 as deflection increases. This contact reduces the effective length of flexible section 966 thereby increasing the stiffness of centering rod 960. Thus, centering rod becomes effectively stiffer as the deflection increase. Thus, the shape of distal bore 976 can be utilized to modulate the force/deflection response of the centering rod and a bone anchor/device which incorporates the centering rod. In the embodiment of FIG. 9E, distal bore 976e has a progressive trumpet like shape. However in alternative embodiments the diameter of bore 976e can be change continuously or more rapidly in some regions than in others.

FIG. 9F shows a further alternative embodiment in which distal bore 976 is lined with a sheath 980 of a wear resistant material. Sheath 980 is secured within distal bore 976 prior to introduction of centering rod 960 and before assembly with housing 930. Note that, in this embodiment, sheath 980 does not extend along the full length of proximal end 962 of centering rod 960. Sheath 980 reduces wear caused by moving contact between centering rod 960 and the walls of distal bore 976 during deflection of deflectable post 940. In a preferred embodiment sheath 980 is made of cobalt chrome and is press fit into retainer 942 and centering rod 940. In alternative embodiments sheath 980 can be secured to retainer 942 and centering rod 940 using conventional mechanical fasteners or bonding techniques e.g. laser welding. In an alternative embodiment sheath 980 is made of PEEK or another biocompatible wear-resistant material. Alternatively, instead of using a separate sheath component, a cobalt chrome or other wear-resistant coating can be deposited, spayed, or coated on the surface of the distal bore 976 to reduce wear from moving contact.

Figure 10A:
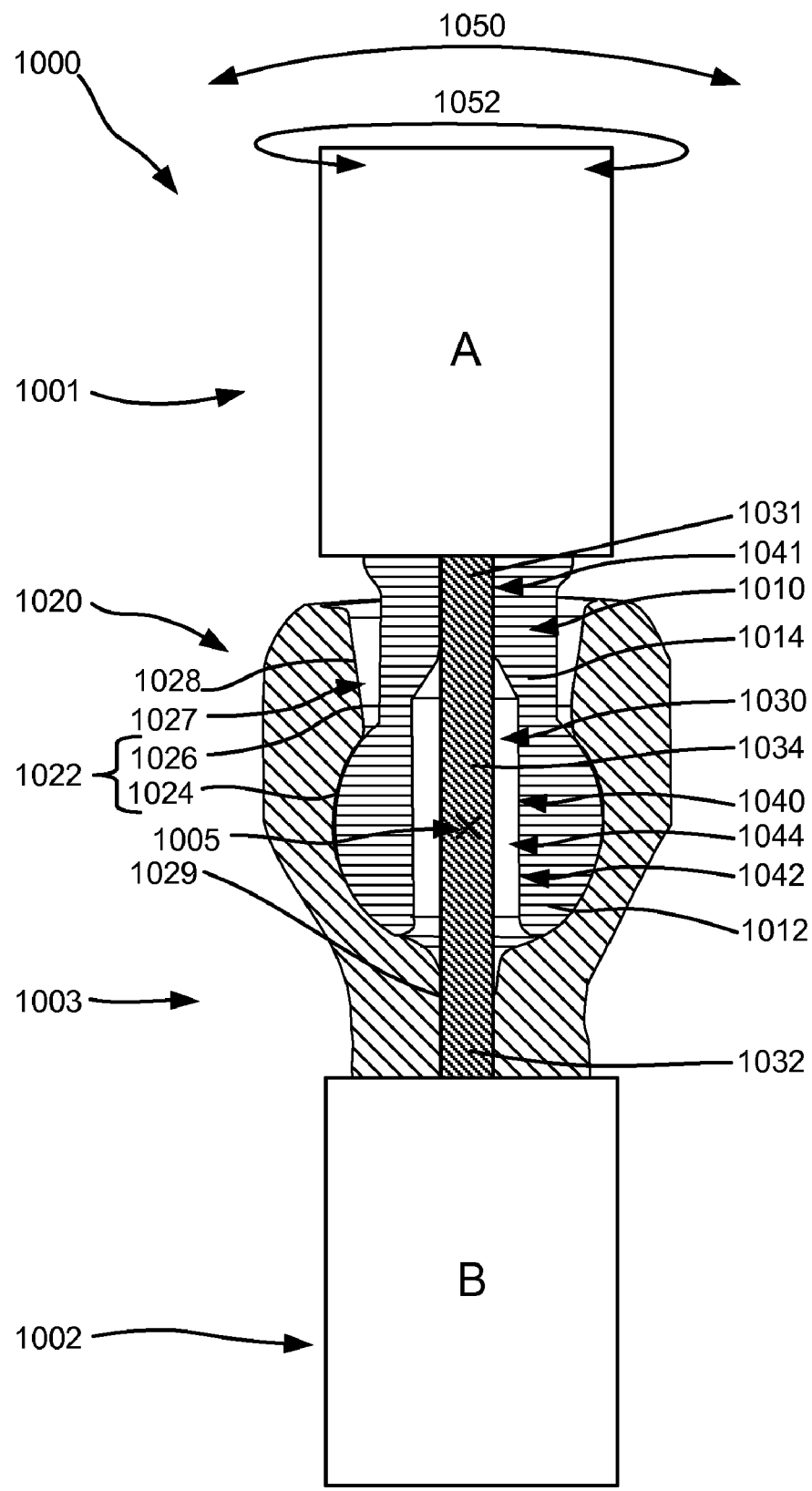
FIG. 10A shows a schematic view of a spinal implant component utilizing a self-centering ball-joint according to an embodiment of the invention.

FIG. 10A illustrates schematically an implant component 1000 utilizing a self-centering ball-joint of the type illustrated with respect to FIGS. 8A-8D and 9A-9D. FIG. 10A shows a partial sectional view exploded view of implant component 1000. Referring first to FIG. 10A, implant component 1000 includes, first element 1001, second element 1002, and self-centering ball-joint 1003. Referring to FIG. 10A, first element 1001 is illustrated by box A. First element 1001 can be, for example, one of a rod, a coupling, a fastener, a mount, a bone anchor, a bone hook, and a bone screw. Second element 1002 is illustrated by Box B. Second element 1002 can be, for example, one of a rod, a coupling, a fastener, a mount, a bone anchor, a bone hook, and a bone screw. First element 1001 is connected to second element 1002 by self-centering ball-joint 1003. Self-centering ball-joint 1003 allows first element 1001 to pivot relative to second element 1002 as shown by arrow 1050. Self-centering ball-joint 1003 allows first element 1001 to rotate relative to second element 1002 as shown by arrow 1052. Self-centering ball-joint 1003 constrains the range of pivoting of first element 1001 relative to second element. Self-centering ball-joint 1003 also exerts a centering force in response to pivoting and/or rotation of first element 1001 relative to second element 1002. Self-centering ball-joint 1003 includes a ball-rod 1010, a housing 1020 and a centering rod 1030.

Ball-rod 1010 includes a ball 1012 and a rod 1014. Ball-rod 1010 can be made, for example, from cobalt chrome or titanium. Ball 1012 is a ball-shaped or spherical structure in order to form part of a linkage connecting ball-rod 1010 to housing 1020. First element 1001 is connected to rod 1014 at the opposite end from ball 1012. Ball 1012, rod 1014 and first element 1001 are in some embodiments made in one piece. In alternative embodiments, ball 1012, rod 1014 and first element 1001 are made in two or more pieces and subsequently attached and/or bonded to one another.

A bore 1040 passes along the longitudinal axis of rod 1014 and passes through ball 1012. Bore 1040 includes a first bore 1041 communicating with a center bore 1042. First bore 1041 is sized and configured to receive first end 1031 of centering rod 1030. In a preferred embodiment both centering rod 1030 and first bore 1041 are cylindrical in shape such that the first end 1031 of centering rod 1030 may rotate about its longitudinal axis within first bore 1041. Center bore 1042 is sized and configured to create a space 1044 around center section 1034 of centering rod 1030. Space 1044 is sized to allow bending of centering rod 1030 and deflection of ball-rod 1010 relative to housing 1020. In some embodiments, space 1044 is sized such that center section 1034 of centering rod 1030 does not contact the sides of center bore 1042 over the full range of motion of ball-rod 1010. In alternative embodiments, space 1044 is sized and shaped such that center section 1034 comes into contact progressively with the sides of center bore 1042 over the range of motion of ball-rod 1010 thereby modulating the centering force/deflection response. Center bore 1042 is chamfered where it intersects the surface of ball 1012.

Housing 1020 forms a socket 1022 in which ball-rod 1010 is received. Socket 1022 includes a partial-spherical pocket 1024. Partial-spherical pocket 1024 is sized to receive ball 1012 of ball-rod 1010. A channel 1026 passes out of partial-spherical pocket 1024 through the surface of housing 1020. Channel 1026 is sized to receive rod 1014 of ball-rod 1010. Channel 1026 provides a space 1027 around rod 1014 which allows ball-rod 1010 to pivot relative to housing 1020. Channel 1026 also provides a limit surface 1028 which contacts rod 1014 when rod 1014 has pivoted through a pre-selected angle. Channel 1026 thereby permits pivoting of ball-rod 1010 relative to housing 1020 within constraints determined by the positioning of limit surface 1028. Housing 1020 can be formed in one or more pieces.

Housing 1020 also includes a second bore 1029 which extends from the partial-spherical pocket 1024 opposite channel 1026. Second bore 1029 is sized and configured to receive second end 1032 of centering rod 1030. Second bore 1029 is preferably chamfered where it meets partial-spherical pocket 1024.

Second element 1002 is connected to housing 1020. Housing 1020 and second element 1002 are in some embodiments made in one piece. In alternative embodiments, housing 1020 and second element 1002 are made in two or more pieces and subsequently attached and/or bonded to one another.

Centering rod 1030 is, in a preferred embodiment, a cylindrical rod made of a superelastic metal—for example nitinol. The first end 1031 of centering rod 1030 is sized and configured to be received within first bore 1041 of ball-rod 1010. The second end 1032 of centering rod 1030 is sized and configured to be received within second bore 1029 of housing 1020. In a preferred embodiment both ends of centering rod 1030 are cylindrical in shape. However, in alternative embodiments, the first end 1031 and second end 1032 may have other than a circular section, for example, square, oval, rectangular, or other polygonal. Note that the first end 1031 and second end 1032 of centering rod 1030 can have the same, or different, sectional shapes.

The center section 1034 of centering rod 1030 is designed to bend in response to deflection of ball-rod 1010 relative to housing 1020 and exert a restorative centering force upon ball-rod 1010. The restorative force tends to align the longitudinal axis of the ball-rod 1010 with the longitudinal axis of the housing 1020. The force increases as the angle between the ball-rod 1010 and housing 1020 increases. The diameter and shape of center section 1034 of centering rod 1030 can be designed/selected to achieve a desired restorative force for a given deflection. Center section 1034 can be cylindrical but may have other than a circular section, for example, square, oval, rectangular, or other polygonal. The force/deflection response can accordingly be isotropic or anisotropic depending upon the shape of center section 1034. In one embodiment, centering rod 1030 is 0.063 inch diameter nitinol wire. In alternative embodiment, centering rod 1030 is a superelastic nitinol wire having a diameter between 0.060 and 0.080 inches. However centering rod 1030 can be sized and shaped as necessary to achieve the desired force/deflection response for the system.

Implant component 1000 is assembled prior to implantation in a patient. During assembly, centering rod 1030 (shown by dashed lines) is received in bore 1040 and second bore 1029 (see FIGS. 10A and 10C). As shown in FIG. 10C, first end 1031 of centering rod 1030 is received in first bore 1041 of ball-rod 1010. Second end 1032 of centering rod 1030 is received within second bore 1029 of housing 1020. Center section 1034 of centering rod 1030 is received within center bore 1042 of ball-rod 1010. Note that a space 1044 exists around center section 1034 leaving center section 1034 free to flex when ball-rod 1010 pivots about pivot point 1005.

Because bore 1040 and second bore 1029 are closed, it is not necessary to attach centering rod 1030 to either of ball-rod 1010 or housing 1020. However, if desired, centering rod 1030 can be attached to either or both of ball-rod 1010 and housing 1020 by mechanical means (e.g. pins), welding or other fastening method/device. Ball 1012 is received in partial-spherical pocket 1024. Partial-spherical pocket 1024 is shaped to secure ball 1012 within partial-spherical pocket 1024 while allowing ball 1012 to pivot and rotate. Accordingly, in this embodiment, a ball-joint is formed. Ball-rod 1010 extends through and out of channel 1026 such that first element 1001 is external to housing 1020. Ball-rod 1010 pivots about a pivot point 1005 indicated by an X. In a preferred embodiment the pivot point 1005 is positioned on the center of the section of centering rod 1030 (at least when the longitudinal axis of the ball-rod 1010 and housing 1020 are aligned). Ball-rod 1010 may pivot about pivot point 1005 in any direction, as shown by arrow 1050. Concurrently or alternatively, ball-rod 1010 can rotate, as shown by arrow 1052, about the long axis of ball-rod 1010 (which also passes through pivot point 1005).

Figure 10B:
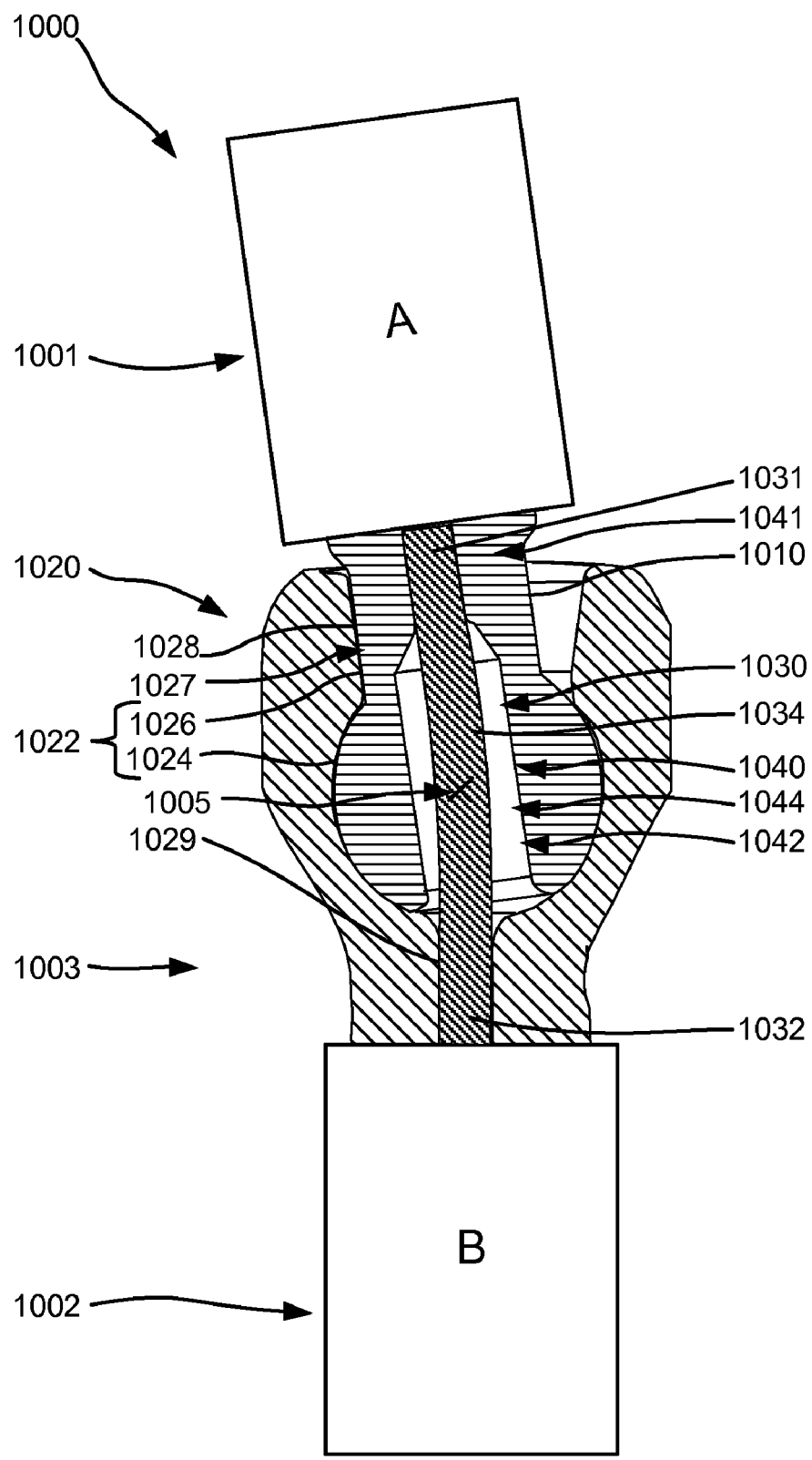
FIG. 10B shows a schematic view of the spinal implant component of FIG. 10A illustrating deflection of the ball-joint.

FIG. 10B illustrates deflection of ball-rod 1010. Applying a force to first element 1001 causes deflection of ball-rod 1010 of implant component 1000. Ball-rod 1010 pivots about pivot point 1005 located at the center of ball 1012. First end 1031 of centering rod 1030 remains aligned with ball-rod 1010 whereas second end 1032 remains aligned with housing 1020. Thus center section 1034 of centering rod 1030 bends elastically in response to deflection of ball-rod 1010. Centering rod 1030 thus applies a centering force upon ball-rod 1010 pushing it back into alignment with housing 1020. The magnitude of the force increases as the deflection increases. The magnitude of the force can be selected based on the configuration and material of centering rod 1030. For example a larger diameter cylindrical nitinol rod will provide a larger centering force than a smaller diameter rod for the same amount of deflection. Note that, in this embodiment, center bore 1042 is sufficiently large that center section 1034 of centering rod 1030 does not contact the sides of center bore 1044 over the range of deflection of ball-rod 1010 as limited by contact with limit surface 1028 of housing 1020. In a preferred embodiment, centering rod 1030 is floating, that is to say that it is not fixed to one or both of ball-rod 1010 and housing 1020. Thus, upon deflection of ball-rod 1010, centering rod 1030 can slide somewhat in one or both of first bore 1041 and second bore 1029 such that the centering rod 1030 is not placed under longitudinal tension during deflection of ball-rod 1010.

In a preferred embodiment, ball-rod 1010 may deflect from 0.5 mm to 2 mm in any direction before making contact with limit surface 1028. More preferably, ball-rod 1010 may deflect approximately 1 mm before making contact with limit surface 1028. After a fixed amount of deflection, ball-rod 1010 comes into contact with limit surface 1028 of housing 1020. Limit surface 1028 is oriented such that when ball-rod 1010 makes contact with limit surface 1028, the contact is distributed over an area to reduce stress on ball-rod 1010. In this embodiment, the ball-rod 1010 contacts the entire sloping side of the conically-shaped limit surface 1028. After ball-rod 1010 comes into contact with limit surface 1028, further deflection requires deformation (bending) of ball-rod 1010. Bending of ball-rod 1010 requires significantly more force than bending of centering rod 1030.

FIG. 10C illustrates an alternative configuration of an implant component 1000c. As shown in FIG. 10C, first element 1001, second element 1002 and self-centering ball-joint 1003 need not be arranged in line with one another. In implant component 1000c, second element 1002 is offset from the axis of ball-rod 1010.

Figure 10D:
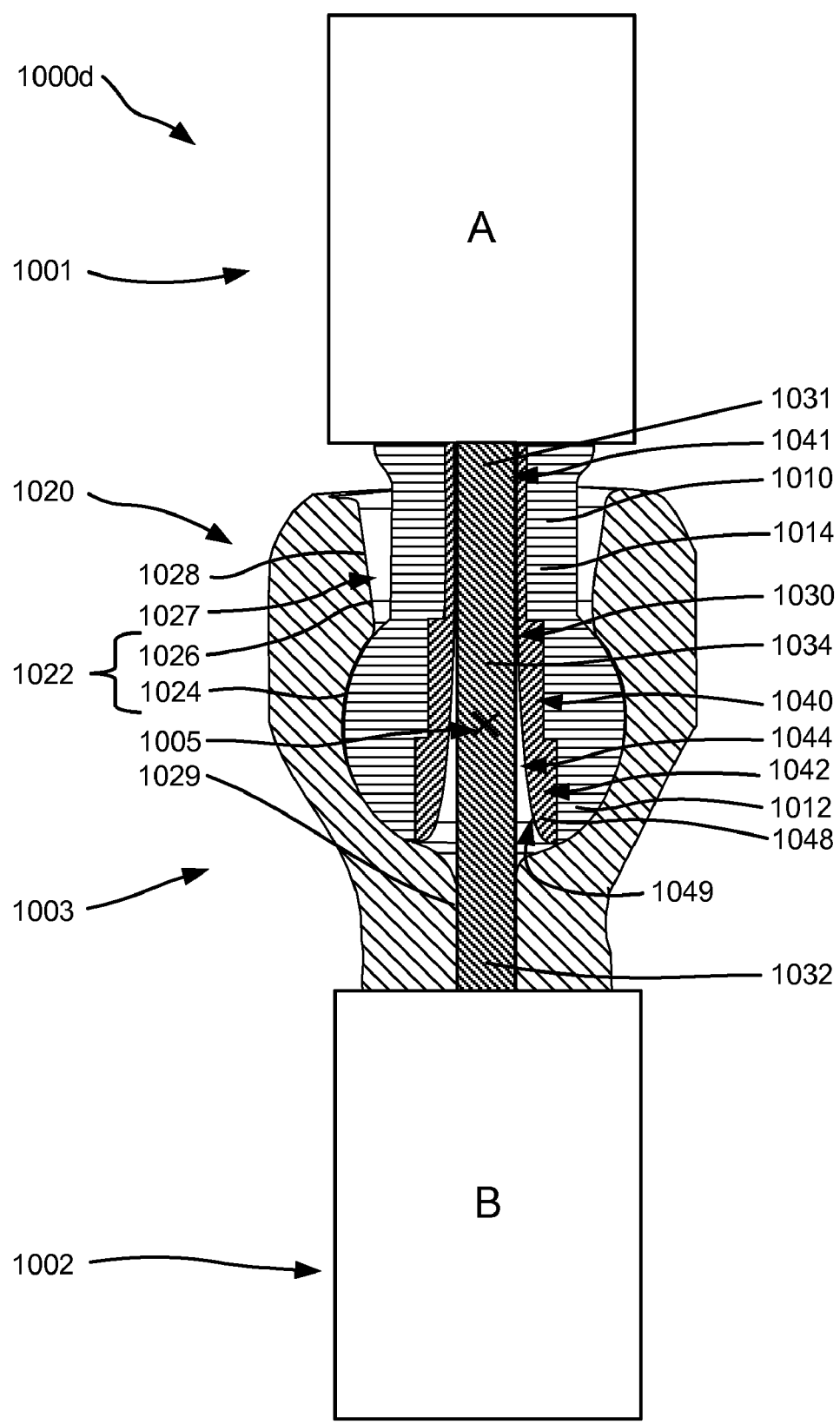
FIG. 10D shows a schematic view of the spinal implant component of FIG. 10A incorporating an additional component.

Moving contact between centering rod 1030 and ball-rod 1010 can cause wearing of the surface of the ball-rod 1010 and/or centering rod 1030. FIG. 10D illustrates an optional component which can be incorporated into ball-rod 1010 to reduce such wear. FIG. 10D shows a sleeve 1048 designed to fit within bore 1040 of ball-rod 1010. Sleeve 1048 forms in intermediate layer between ball-rod 1010 and centering rod 1030. Sleeve 1048 is made of a material which protects centering rod 1030 and ball-rod 1010 from wear during moving contact. In a preferred embodiment, sleeve 1048 is made of cobalt chrome or PEEK, however, other biocompatible wear resistant materials and/or coatings can be used. Ball-rod 1010 can be made of titanium, titanium alloy, cobalt chrome or cobalt chrome coated titanium.

FIG. 10D shows a sectional view of an implant component 1000d which includes sleeve 1048. Sleeve 1048 is placed into bore 1040 of ball-rod 1010 prior to assembly with housing 1020. Sleeve 1048 can be press fit into bore 1040 and/or can be secured within bore 1040 using conventional mechanical or bonding techniques appropriate for the selected material. As shown in FIG. 10D, sleeve 1048 is positioned between centering rod 1030 and the walls of bore 1040. Center section 1034 of centering rod 1030 is received within center bore 1042 of ball-rod 1010. Note that an annular space 1044 exists around center section 1034 and sleeve 1048 leaving center section 1034 free to flex when ball-rod 1010 pivots about pivot point 1005. As previously described ball 1012 fits into a partial-spherical pocket 1024 of housing 1020. Partial-spherical pocket 1024 is shaped to secure ball 1012 within partial-spherical pocket 1024 while allowing ball 1012 to pivot and rotate. Accordingly, in this embodiment, a ball-joint is formed.

Ball-rod 1010 pivots about a pivot point 1005 indicated by an X. In a preferred embodiment the pivot point 1005 is positioned on the center of the section of centering rod 1030. Ball-rod 1010 may pivot about pivot point 1005 in any direction. Concurrently or alternatively, ball-rod 1010 can rotate, about the long axis of ball-rod 1010 (which also passes through pivot point 1005). Sleeve 1048 is positioned between centering rod 1030 and the walls of bore 1040 of ball-rod 1010 such that if there is moving contact between the parts during deflection and/or rotation, the parts are protected from wear. In the embodiment of FIG. 10D, sleeve 1048 has a curved interior bore 1049 shaped to accommodate flexing of centering rod 1030 during pivoting of ball-rod 1010 relative to housing 1020.

Figure 10E:
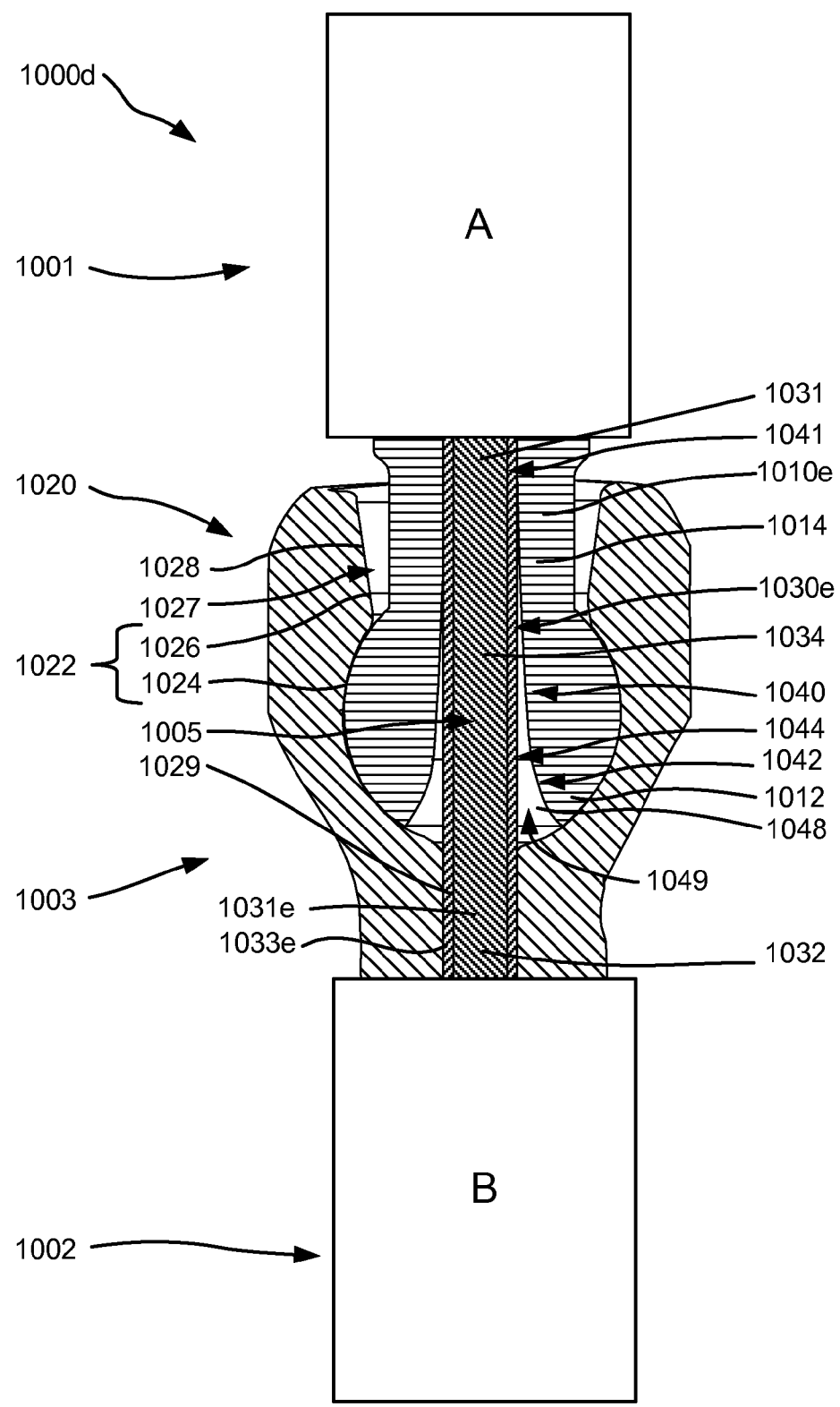
FIG. 10E shows a schematic view of the spinal implant component of FIG. 10A having a centering rod with an inner core and outer sheath.

FIG. 10E illustrates an alternative implant component 1000e which includes a centering rod 1030e having an inner metal core and an outer polymer sheath which can be used to reduce such wear. Moving contact between centering rod 1030 and ball-rod 1010 can cause wearing of the surface of the ball-rod 1010 and/or centering rod 1030. As shown in FIG. 10E centering rod 1030e includes an inner metal core 1031e and an outer polymer sheath 1033e. Sheath 1033e forms in intermediate layer between ball-rod 1010e and centering rod 1030e. Sheath 1033e is made of a biocompatible polymer which protects centering rod 1030e and ball-rod 1010e from wear during moving contact. In a preferred embodiment, sheath 1033e is made of PEEK, however, other flexible and resilient biocompatible materials and/or coatings can be used. In all other ways alternative implant component 1000e is similar or identical to implant component 1000 as previously described.

Centering Rods

As illustrated in FIGS. 8A to 10C, in preferred embodiments of the present invention, the centering rod is a cylinder of a superelastic metal—for example nitinol. However, centering rods can be manufactured in a range of different configurations and materials depending upon the desired force deflection characteristics desired for the ball-joint in which they are used. For example, in some embodiments, by adjusting the properties of the centering rod, the deflection characteristics of a bone anchor can be configured to approach the natural dynamic motion of the spine, while giving dynamic support to the spine in that region. It is contemplated, for example, that the flexible bone anchor can replicate a 70% range of motion and flexibility of the natural intact spine, a 50% range of motion and flexibility of the natural intact spine and a 30% range of motion and flexibility of the natural intact spine. In some cases, a kit is provided to a doctor having a set of flexible bone anchors with different force/deflection characteristics from which the doctor may select the flexible bone anchors most suitable for a particular patient. In other cases, the surgeon may select bone anchors prior to the procedure based upon pre-operative assessment. In embodiments centering rod is designed to maintain a deflectable post coaxial with the bone anchor during implantation of the bone anchor thereby ensuring that a desirable range of motion/load sharing is provided.

The stiffness of the centering rod may thus be varied or customized according to the needs of a patient or application. Furthermore, one feature of the present invention is to allow the efficient manufacture of a range of deflectable bone anchors having a range of different force-deflection characteristics. This can readily be accomplished by manufacturing a range of centering rods having different force-deflection characteristics and leaving the remainder of the components unchanged. In this way, the range of deflectable bone anchors is adapted to be manufactured with a minimum number of unique parts.

FIGS. 11A-11F illustrate alternative designs for centering rods which can be utilized in any of the self-centering ball-joints described herein. In some embodiments, the centering rods of FIGS. 11A-11F are provided with a wear-resistant coating and/or sheath on surfaces subject to moving contact in order to reduce wear. Alternatively, the centering rods of FIGS. 11A-11F can be manufactured in whole of in part from materials resistant to wear—for example cobalt chrome. Alternatively, the centering rods are not provided with a wear resistant coating.

Figure 11A:
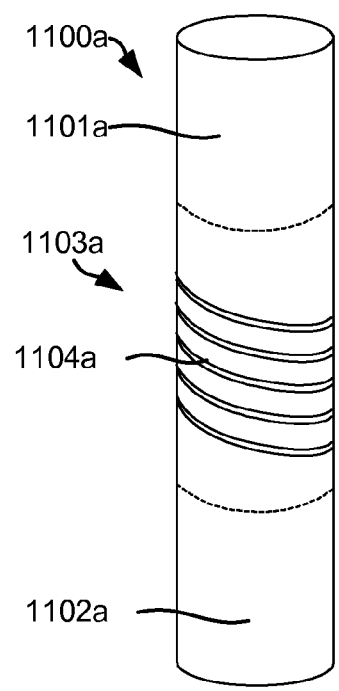

FIG. 11A shows a first example of an alternative centering rod 1100a for use in a self-centering ball-joint. Centering rod 1100a has a first end 1101a sized and configured to be received within a bore of a ball-rod (see, e.g. ball-rod 1010 of FIG. 10A). Centering rod 1100a has a second end 1102a sized and configured to be received within a bore of housing (see, e.g. housing 1020 of FIG. 10A). In a preferred embodiment both ends of centering rod 1100a are cylindrical in shape.

However, in alternative embodiments, the ends of centering rod 1100*a* may have other than a circular section, for example, square, oval, rectangular, or other polygonal to match the bore of the housing and ball-rod. Note that the first end 1101*a* and second end 1102*a* of centering rod 1100*a* can have the same, or different, sectional shapes.

Referring again to FIG. 11A, centering rod 1100*a* has a flexible section 1103*a* between the first end 1101*a* and the second end 1102*a*. Flexible section 1103*a* is designed to bend to allow deflection of the axis of first end 1101*a* relative to the axis of the second end 1102*a*. Flexible section 1103*a* is designed to elastically deform over the designed range of motion and exert a restorative centering force to bring the axis of first end 1101*a* back into alignment with the axis of the second end 1102*a*. The magnitude of the centering force can be selected based on the design of flexible section 1103*a* and the choice of material for flexible section 1103*a*. In the embodiment of FIG. 11A, flexible section 1103*a* is a portion of centering rod 1100*a* which has enhanced elasticity or flexibility compared to the rest of centering rod 1100*a* by the introduction of a slot or groove 1104*a*. Groove 1104*a* has a spiral configuration or may have some other configuration adapted to increase the flexibility of flexible section 1103*a*. Flexible section 1103*a* is in some embodiments formed in one piece with first end 1101*a* and second end 1102*a*, but may alternatively be formed separately and attached by laser welding, soldering or other bonding technology. Centering rod 1100*a* can be formed, for example, from an implantable metal such as steel, titanium or nitinol.

Groove 1104*a* leaves the material of flexible section 1103*a* in the shape of a coil spring. By changing the dimensions of the flexible section 1103*a* and groove 1104*a*, the deflection characteristics of the centering rod 1100*a* can be changed. The stiffness of components of the centering rod can be, for example, increased by increasing the diameter of centering rod 1100*a*. Additionally, increasing the amount of material removed in groove 1104*a* will decrease the stiffness of the centering rod 1100*a*. Alternatively and/or additionally, changing the materials which comprise the components of the centering rod 1100*a* can also affect the stiffness of the centering rod. For example, making centering rod 1100*a* out of stiffer material reduces deformation of centering rod 1100*a* for the same amount of load—all other factors being equal.

The centering rod 1100*a* may have the same force deflection response in each direction of deflection of the centering rod (isotropic). The centering rod 1100*a* may alternatively have different force/deflection properties in different directions (anisotropic). For example, the centering rod 1100*a* can have different effective spring constant in different directions by adjusting, for example, the thickness of the groove 1104*a* in one region compared to another region.

Figure 11B:
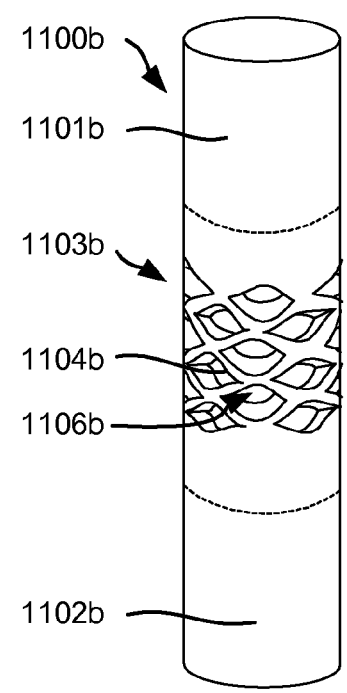

FIG. 11B shows another example of an alternative centering rod 1100*b* for use in a self-centering ball-joint. Centering rod 1100*b* has a first end 1101*b* sized and configured to be received within a bore of a ball-rod (see, e.g. ball-rod 1010 of FIG. 10A). Centering rod 1100*b* has a second end 1102*b* sized and configured to be received within a bore of housing (see, e.g. housing 1020 of FIG. 10A). In a preferred embodiment both ends of centering rod 1100*b* are cylindrical in shape. However, in alternative embodiments, the ends of centering rod 1100*b* may have other than a circular section, for example, square, oval, rectangular, or other polygonal to match the bore of the housing and ball-rod. Note that the first end 1101*b* and second end 1102*b* of centering rod 1100*b* can have the same, or different, sectional shapes.

Referring again to FIG. 11B, centering rod 1100*b* has a flexible section 1103*b* between the first end 1101*b* and the second end 1102*b*. Flexible section 1103*b* is designed to bend to allow deflection of the axis of first end 1101*b* relative to the axis of the second end 1102*b*. Flexible section 1103*b* is designed to elastically deform over the designed range of motion and exert a restorative centering force to bring the axis of first end 1101*b* back into alignment with the axis of the second end 1102*b*. The magnitude of the centering force can be selected based on the design of flexible section 1103*b* and the choice of material for flexible section 1103*b*. In the embodiment of FIG. 11B, Flexible section 1103*b* is cylindrical in shape with an internal cavity 1106*b*. Internal cavity 1106*b* is made, for example, by drilling from one end of centering rod 1100*b*. A plurality of apertures 1104*b* pierces the wall of flexible section 1103*b* into cavity 1106*b*. The apertures 1104*b* are designed to increase the flexibility of flexible section 1103*b* as compared to other regions centering rod 1100*b*. In the embodiment shown in FIG. 1100B, apertures 1104*b* are shaped to leave material of flexible section 1103*b* in the form of a multi-level wave spring. Flexible section 1103*b* is in some embodiments formed in one piece with first end 1101*b* and second end 1102*b*, but may alternatively be formed separately and attached by laser welding, soldering or other bonding technology. Centering rod 1100*b* can be formed, for example, from an implantable metal such as steel, titanium or nitinol. In alternative embodiments, the apertures 1104*b* and cavity 1106*b* are filled with a compliant material, for example a biocompatible polymer such as PEEK or BIONATE™.

Figure 11C:
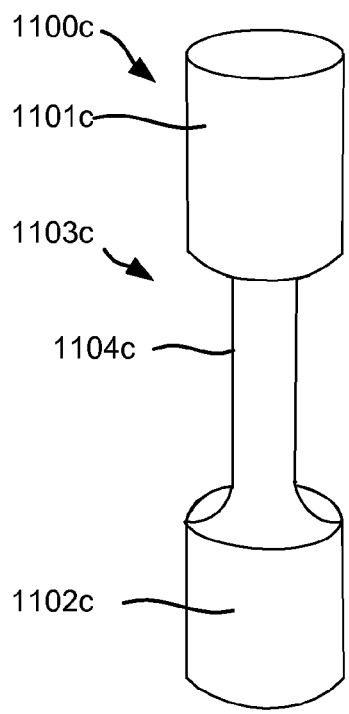

FIG. 11C shows another example of an alternative centering rod 1100*c* for use in a self-centering ball-joint. Centering rod 1100*c* has a first end 1101*c* sized and configured to be received within a bore of a ball-rod (see, e.g. ball-rod 1010 of FIG. 10A). Centering rod 1100*c* has a second end 1102*c* sized and configured to be received within a bore of housing (see, e.g. housing 1020 of FIG. 10A). In a preferred embodiment both ends of centering rod 1100*c* are cylindrical in shape. However, in alternative embodiments, the ends of centering rod 1100*c* may have other than a circular section, for example, square, oval, rectangular, or other polygonal to match the bore of the housing and ball-rod. Note that the first end 1101*c* and second end 1102*c* of centering rod 1100*c* can have the same, or different, sectional shapes.

Referring again to FIG. 11C, centering rod 1100*c* has a flexible section 1103*c* between the first end 1101*c* and the second end 1102*c*. Flexible section 1103*c* is designed to bend to allow deflection of the axis of first end 1101*c* relative to the axis of the second end 1102*c*. Flexible section 1103*c* is designed to elastically deform over the designed range of motion and exert a restorative centering force to bring the axis of first end 1101*c* back into alignment with the axis of the second end 1102*c*. The magnitude of the centering force can be selected based on the design of flexible section 1103*c* and the choice of material for flexible section 1103*c*. In the embodiment of FIG. 11C, flexible section 1103*c* is a portion of centering rod 1100*c* enhanced elasticity or flexibility compared to the rest of centering rod 1100*c* because it has reduced cross-sectional area by removal of material in the region 1104*c*. A range of centering rods 1100*c* can be created having different cross-sectional areas in flexible section 1103*c* and thus having differing spring constants. By keeping first end 1101*c* and second end 1102*c* with a standard diameter while changing only flexible section 1103*c*, it is possible to create a range of spinal implant components having different force/deflection characteristics while only having to change one part—the centering rod—of the component. In alternative some embodiments flexible section 1103*c* is larger in diameter than first end 1101c and second end 1102c resulting in an increased spring constant relative to a cylinder of the same material.

Figure 11D:
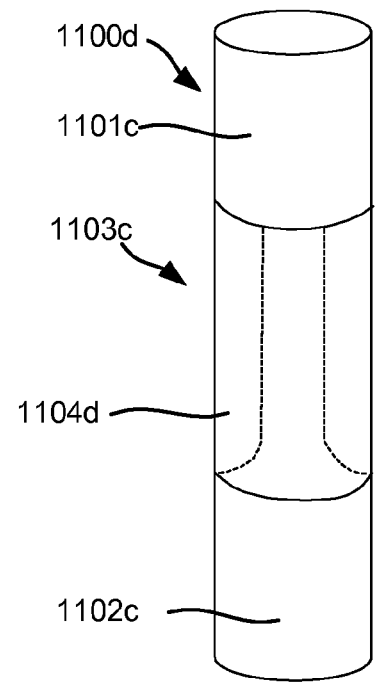

In the embodiment of a centering rod 1100d shown in FIG. 11D, flexible section 1103c of FIG. 11C is also provided with a sleeve 1104d. Sleeve 1104d can be formed of a compliant material, for example a biocompatible polymer such as PEEK or BIONATE™. A sleeve 1104d can be used to modulate the spring constant of flexible section 1103c, reduce wear of metal components, and/or make contact and or fill the space surrounding the flexible section 1103c when installed in a bore of a ball-rod. A range of centering rods 1100d can be created having differing spring constants by changing the diameter of the flexible section 1103c and the sleeve 1104d. In some embodiments sleeve 1104d is larger or smaller in diameter than first end 1101c and second end 1102c.

FIG. 11E shows another example of an alternative centering rod 1100e for use in a self-centering ball-joint. Centering rod 1100e has a first end 1101e sized and configured to be received within a bore of a ball-rod (see, e.g. ball-rod 1010 of FIG. 10A). Centering rod 1100e has a second end 1102e sized and configured to be received within a bore of housing (see, e.g. housing 1020 of FIG. 10A). As shown in FIG. 11E, both ends of centering rod 1100e are hexagonal in section. When received in matching bores, the hexagonal first end 1101e and second end 1102e engage prevent rotation of the first end first end 1101e and second end 1102e within the bore. Thus, for example, rotation of a ball-rod relative causes twisting of flexible section 1103e of the centering rod. As a consequence, centering rod 1100e flexibly resists rotation of e.g. a ball-rod within a socket. the provides a restoring force to return the ball-rod Although a hexagonal section is shown in FIG. 11e, the ends of centering rod 1100e may have sections designed to engage the bore in which they are received, for example, square, oval, rectangular, or other polygonal to match the bore of the housing and ball-rod. Note that the first end 1101e and second end 1102e of centering rod 1100e can have the same, or different, sectional shapes.

FIG. 11F shows another example of an alternative centering rod 1100f for use in a self-centering ball-joint. Centering rod 1100f has a first end 1101f sized and configured to be received within a bore of a ball-rod (see, e.g. ball-rod 1010 of FIG. 10A). Centering rod 1100f has a second end 1102f sized and configured to be received within a bore of housing (see, e.g. housing 1020 of FIG. 10A). As shown in FIG. 11F, both ends of centering rod 1100f are rectangular in section. When received in matching bores, the rectangular first end 1101f and second end 1102f engage prevent rotation of the first end first end 1101f and second end 1102e within the bore. Thus, for example, rotation of a ball-rod relative causes twisting of flexible section 1103f of the centering rod. As a consequence, centering rod 1100f flexibly resists rotation of e.g. a ball-rod within a socket.

Flexible section 1103f connects first end 1101f and second end 1102f. Flexible section 1103f is designed to permit movement of first end 1101f relative to second end 1102f. For example, flexible section 1103f may by a portion of centering rod 1100f which has enhanced elasticity or flexibility compared to the rest of centering rod 1100f. Flexible section 1103f is preferably formed in one piece with second end 1102f and first end 1101f or may alternatively be formed separately and attached by laser welding, soldering or other bonding technology. Flexible section 1103f has a rectangular cross-section which is wider in one direction than the other. Flexible section 1103f is thus more flexible bending in a direction parallel to the short axis of the rectangular section (see arrow 1140) than in a direction parallel to the long axis of the rectangular section (see arrow 1142). Thus flexible section has an anisotropic force-deflection profile. The centering rod 1100f has different force/deflection properties in different directions (anisotropic). The disparity between the thicknesses of the flexible section 1103f in one direction compared to another can be used to control the anisotropic force/deflection profile of the centering rod 1100f. The anisotropic force/deflection profile of a bone anchor utilizing centering rod 110f may be useful where it is necessary or desirable to provider greater or lesser load-sharing and/or stabilization on one axis of spinal motion as compared to another.

Accordingly, the devices of the present invention provide in some embodiments the ability to control stiffness for extension, flexion, lateral bending and axial rotation, and to control stiffness for each of these motions independently of the other motions. The characteristics of the deflectable post can be changed, for example, by adjusting the diameter of post and/ or the properties of the centering rod and/or the distance between the deflectable post and the limit surface. These deflection characteristics need not be isotropic. A bias can be introduced in the deflectable post by varying the shape of the bore, the shape of the centering rod and the space between the deflectable post and the limit surface.

For example, by varying the shape of the cap/socket the distance between the deflectable post and the limit surface may also be varied. By making the distance shorter, the amount of deflection can be reduced that occurs before the increase in stiffness caused by contact with the limit surface. The cap/socket may be shaped to reduce the gap between the post and the limit surface uniformly or may be shaped to reduce the gap between the post and the limit surface more in some directions than in others (anisotropically).

In embodiments where the deflectable post has anisotropic force-deflection response, it is important to ensure that the deflectable post is implanted in the correct orientation. The deflectable post is therefore provided with discernable visual or physical characteristics (e.g. an arrow, color, indentation or other observable indicator) which guide the surgeon to the correct orientation of implantation. When correctly installed, a deflectable post with anisotropic force-deflection response may be used to control stiffness for extension, flexion, lateral bending and axial rotation independently. For example, if a deflectable post is more flexible in the upward direction (relative to the spine after implantation—the head direction being up), the post can deflect more when the spine is placed in flexion and can deflect less when the spine is placed in extension. In effect, this arrangement is more restrictive with respect to movement of the spine with the spine in extension and less restrictive with respect to the movement of the spine with the spine in flexion. Conversely, if the deflectable post is more compliant in the down direction (relative to the spine after implantation—the head direction being up), the post can deflect more when the spine is placed in extension and can deflect less when the spine is placed in flexion. In effect, this arrangement is more restrictive with respect to movement of the spine in flexion and less restrictive with respect to the movement of the spine in extension.

In some embodiments it is desirable for the centering rod to have a sheath made of a material selected to reduced wear caused by moving contact between the centering rod and the deflectable post and/or bone anchor. Thus, for example, the centering rod is, in some embodiments, provided with a sheath made from a wear resistant biocompatible polymer. FIG. 11G shows an alternative centering rod 1100g which uses as a core 1105g centering rod 1100a of FIG. 11A and adds a sheath 1107g. Centering rod 1100g has a first end 1101g sized and configured to be received within a bore of a ball-rod (see, e.g. ball-rod 1010 of FIG. 10A). Centering rod 1100*g* has a second end 1102*g* sized and configured to be received within a bore of housing (see, e.g. housing 1020 of FIG. 10A). In a preferred embodiment both ends of centering rod 1100*g* are cylindrical in shape.

As previously described, centering rod 1100*g* has a flexible section 1103*g* between the first end 1101*g* and the second end 1102*g*. Flexible section 1103*g* is a portion of centering rod 1100*a* which has enhanced elasticity or flexibility compared to the rest of centering rod 1100*a* by the introduction of a slot or groove 1104*a*. Groove 1104*g* has a spiral configuration or may have some other configuration adapted to increase the flexibility of flexible section 1103*g*. Flexible section 1103*g* is in some embodiments formed in one piece with first end 1101*g* and second end 1102*g*, but may alternatively be formed separately and attached by laser welding, soldering or other bonding technology. Core 1105*g* can be formed, for example, from an implantable metal such as steel, titanium or nitinol. In a preferred embodiment sheath 1107*g* is made from PEEK, however, other biocompatible wear resistant polymers can be used in alternative embodiments. A sheath can similarly be added to any of the centering rods described herein in order to decrease wear at the interface between the centering rod and the ball-rod/deflectable post and/or modulate the force deflection response of the centering rod.

Figure 12A:
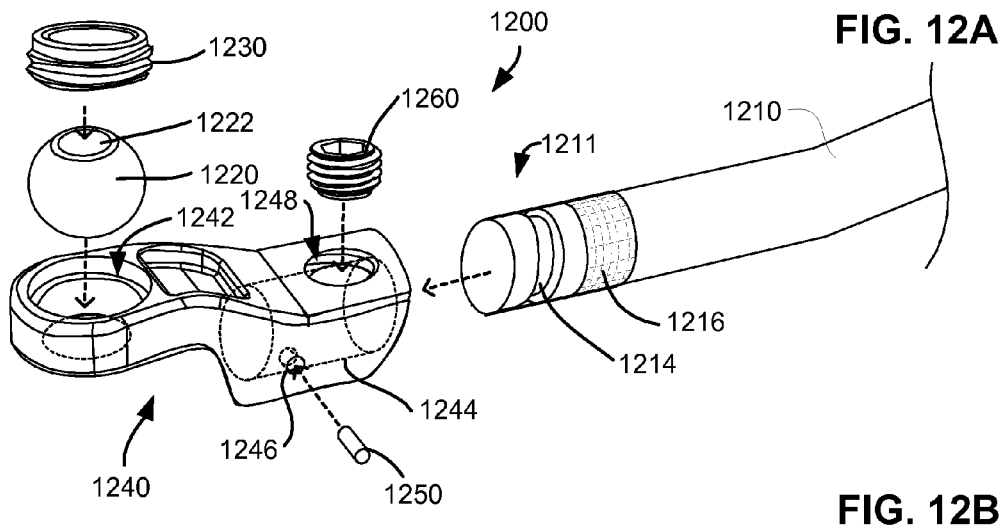
FIG. 12A shows an exploded view of a compound spinal rod according to an embodiment of the present invention.

FIG. 12A illustrates a preferred embodiment of a compound spinal rod 1200 for use with bone anchor such as bone anchor 800 of FIGS. 8A-8D or bone anchor 900 of FIGS. 9A-9D. As shown in FIG. 12A, compound spinal rod 1200 comprises a rod 1210 and a rod-end 1240.

Rod 1210 is preferably a 5.5 mm diameter titanium rod. Rod 1210 is from 50 mm to 150 mm in length. First end 1211 of rod 1210 is design to mate with rod-end 1240. A groove 1214 runs around rod 1210 at first end 1211. Adjacent groove 1214 has a band 1216 around rod 1210 can be knurled or provided with grooves/ribs to enhance engagement by a set screw 1260.

Rod-end 1240 has a pocket 1242 at one end sized to receive a ball 1220. Ball 1220 is preferably a cobalt chrome ball. Ball 1220 has an aperture 1222 designed to engage the mount of a bone anchor. Pocket 1212 is threaded to receive cap 1230. Cap 1230 is preferably titanium and may be laser welded or otherwise secured to rod-end 1240 after assembly. Ball 1220 is inserted into pocket 1212 and secured into place with threaded cap 1230.

Rod end 1240 has a substantially-cylindrical bore 1244 (see dashed lines) at the end opposite pocket 1242. Bore 1244 is configured to receive first end 1211 of rod 1210. A channel 1246 passes through rod-end 1240 perpendicular to bore 1244 and intersecting the edge of bore 1244. Channel 1246 is positioned to correspond with the position of groove 1214 when rod 1210 is inserted in bore 1244. Channel 1246 is sized to receive a locking pin 1250. When inserted in channel 1246, locking pin 1250 projects into groove 1214 preventing rod-end 1240 from being removed from rod 1210. Rod-end 1240 can still rotate around first end 1211 of rod 1210 and can also slide along rod 1210 with a range limited by contact between locking pin 1250 and the sides of groove 1214.

Rod-end 1240 also has a threaded bore 1248 which is perpendicular to bore 1244 and intersect bore 1244. Threaded bore 1248 is configured to receive a set screw 1260. In a preferred embodiment, threaded bore 1248 is positioned such that set screw 1260 engages rod 1210 with band 1216. Set screw 1260 is in some embodiments pivotally connected at its distal end to a curved driver element in order to better engage the surface of rod 1210. Set screw 1260 when tightened is configured to engage first end 1211 of rod 1210 to lock the position of rod-end 1240 relative to rod 1210. To put it another way, set screw 1260 is adapted to engage rod 1210 to prevent further rotation and sliding of first end 1211 within bore 1244.

Figure 12B:
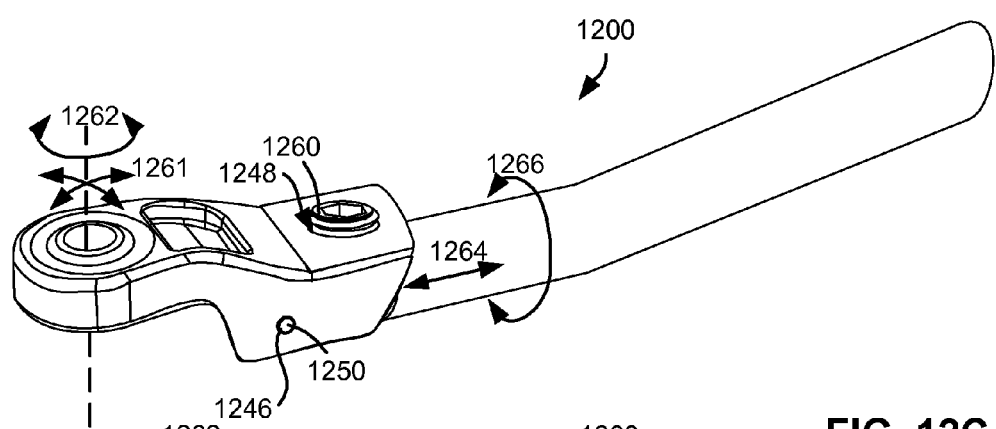
FIG. 12B shows a perspective view of the compound spinal rod of FIG. 12A as assembled.

FIG. 12B shows a perspective view of compound spinal rod 1200 as assembled. As shown in FIG. 12B, ball 1220 has been inserted into pocket 1242 of rod-end 1240. Cap 1230 has been installed in pocket 1242 securing ball 1220 and forming a ball-joint. Note that ball 1220 can pivot within pocket 1242 as shown by arrows 1261 and can also rotate within pocket 1242 as shown by arrow 1262. The aperture 1222 is accessible from both sides of ball 1220 to allow ball 1220 to be mounted to the mount of a bone anchor.

Referring again to FIG. 12B, first end 1211 of rod 1210 has been inserted in bore 1244. Locking pin has been inserted through channel 1246 to intersect groove 1214. Set screw 1260 has been inserted in threaded bore 1248. With set screw 1260 loose, rod 1210 can slide longitudinally within bore 1244 as shown by arrow 1264 within limits imposed by contact between pin 1250 and the sides of grove 1214 (see FIG. 12C). In embodiments, rod 1210 has a range of sliding movement between 2 and 10 mm. Rod 1210 can also rotate freely within bore 1244 if groove 1214 passes around the entire circumference of rod 1210. However, if groove 1214 passes only partway around rod 1210, the rotation of rod 1210 within bore 1244 will be constrained by contact between locking pin 1250 and the ends of groove 1214. Set screw 1260 when tightened is configured to engage first end 1211 of rod 1210 to lock the position of rod-end 1240 relative to rod 1210.

Figure 12C:
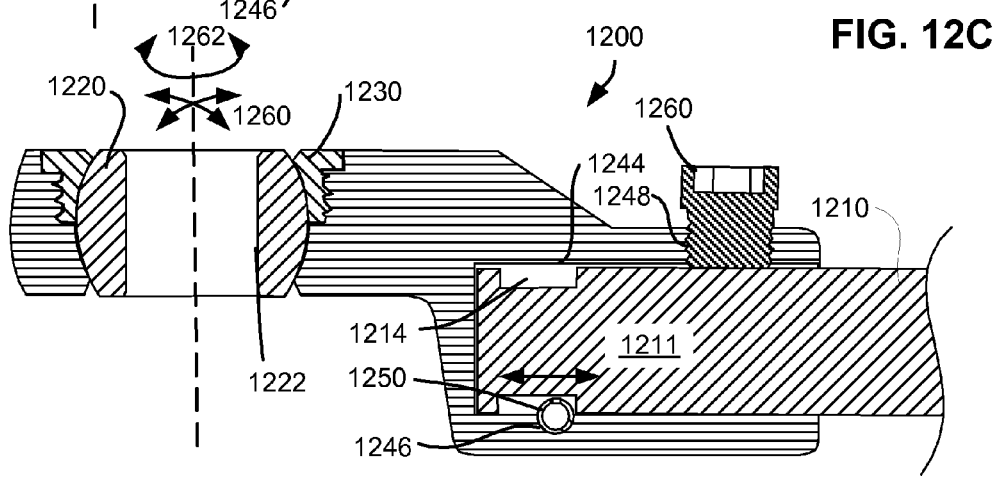
FIG. 12C shows a sectional view of the compound spinal rod of FIG. 12A as assembled.

FIG. 12C shows sectional view of compound spinal rod 1200 as assembled. As shown in FIG. 12C, ball 1220 is held in pocket 1242 of rod-end 1240 by cap 1230. Ball 1220 can, however, rotate 360 degrees around the axis of aperture 1222 as shown by arrow 1262. This allows compound spinal rod 1200 to rotate 360 degrees around the long axis of the bone anchor to which ball 1220 is mounted. Ball 1220 can also tilt from the position shown in FIG. 12B as shown in FIG. 12C by arrows 1260. In a preferred embodiment ball 1220 can tilt 12 degrees in any direction therefore allowing rod-end 1240 to tilt 12 degrees from perpendicular relative to the bone anchor to which ball 1220 is mounted. Note that mount and nut used to secure the ball 1220 to a bone anchor are designed so not as to interfere with the range of motion either in rotation or tilting (See, e.g. FIG. 3A). Locking pin is received in channel 1246 and intersects groove 1214 preventing rod-end 1240 from sliding off first end 1211 of rod 1210. Note that groove 1214 is wider than locking pin 1250 so that rod end 1240 can slide along rod 1210 until locking pin 1250 contacts the walls of groove 1214. As shown in FIG. 12C, set screw 1260 is positioned in threaded bore 1248. The distal end of set screw 1260 enters bore 1244 where is can engage rod 1210 to secure the position of rod-end 1240 relative to rod 1210.

Figure 12D:
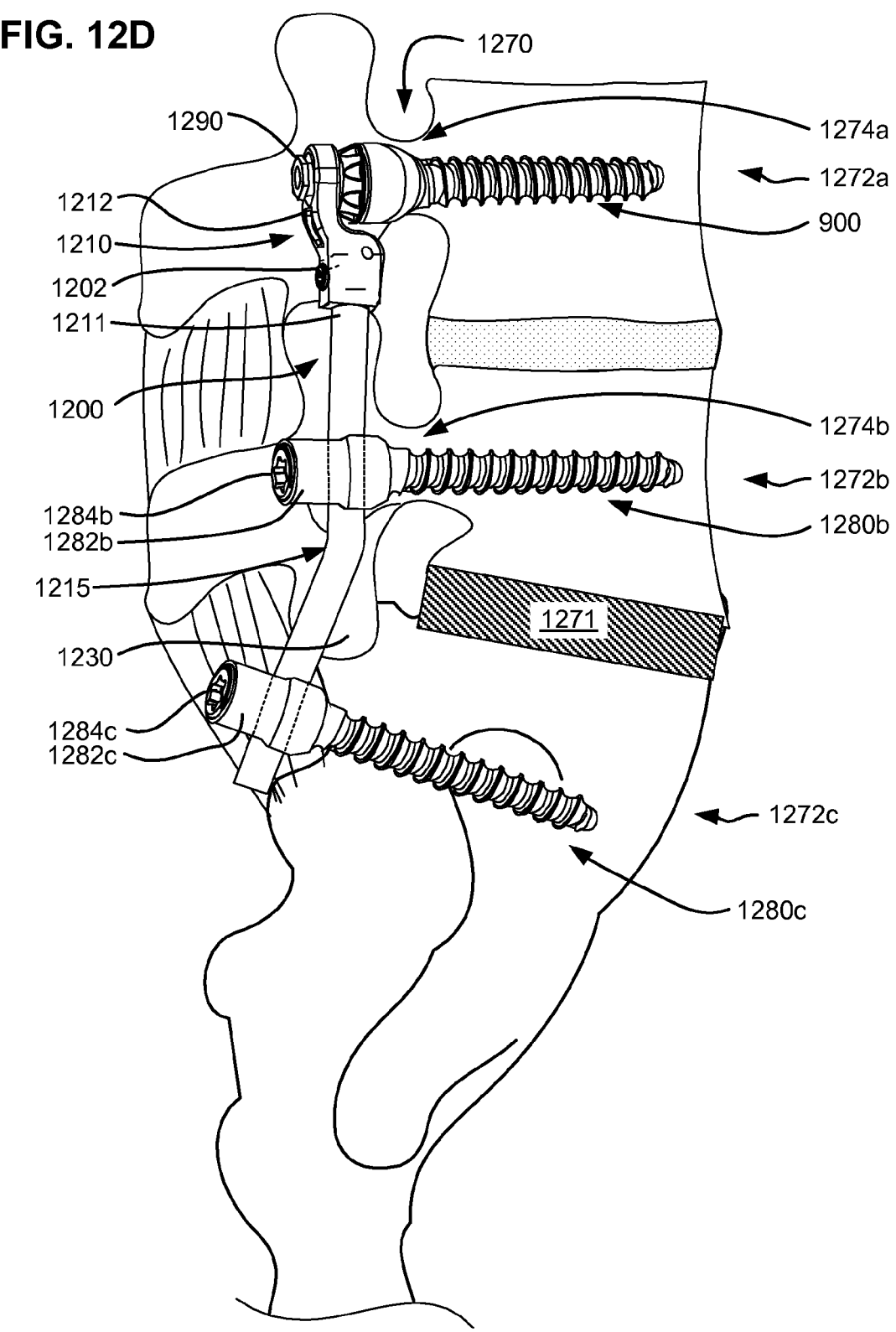
FIG. 12D shows a view of spinal implant prosthesis utilizing the compound spinal rod of FIGS. 12A-12C in conjunction with the bone anchor of FIGS. 9A-9D.

Compound spinal rod 1200 may be used with standard bone anchors, polyaxial screws and/or bone anchors including ball-rods/deflection rods/deflectable posts as described herein. (See, e.g. bone anchor 800 of FIGS. 8A-8D and bone anchor 900 of FIGS. 9A-9D). Likewise, bone anchor 800 of FIGS. 8A-8D and bone anchor 900 of FIGS. 9A-9*d* may be utilized with compound spinal rod 1200, but may also be utilized in conjunction with any of the spinal rods described herein and/or spinal rods not having a ball joint. FIG. 12D shows, for example, a lateral view of a spinal stabilization prosthesis 1270 utilizing the bone anchor 900 of FIGS. 9A-9D in combination with the compound spinal rod 1200 of FIGS. 12A-12C. As shown in FIG. 12D, a spinal prosthesis 1270 can be used to stabilize the L4 and L5 vertebrae 1272*a*, 1272*b* in conjunction with a fusion of L5 to the sacrum 1272*c*.

A fusion of L5 to the sacrum is illustrated schematically by box 1271. Spinal prosthesis 1270 creates a static posterior support of the fusion segment L5-sacrum. Spinal prosthesis 1270 also supports the L4-L5 segment while still permitting some movement at the L4-L5 segment. Spinal prosthesis 1270 can thus be used in a 'topping-off' procedure to support a spinal segment adjacent to a fused segment thereby reducing the likelihood of the increased rate of adjacent segment deterioration sometimes resulting from spinal fusion procedures.

As shown in FIG. 12D, bone anchor 900 is implanted in pedicle 1274a of L4 vertebra 1272a. Conventional pedicle screw 1280b is implanted in pedicle 1274b of L5 vertebrae 1272b. Conventional pedicle screw 1280c is implanted in sacrum 1272c. Ball 1220 of rod-end 1240 is secured to bone anchor 900 by nut 1290. Rod 1210 is positioned in the heads 1282b, 1282c of pedicle screws 1280b, and 1280c. Note that rod 1210 is shaped/bent to support the L4 and L5 vertebrae 1272a, 1272b and sacrum 1272c in the desired positions. As shown in FIG. 12D, rod 1210 has a bend 1215. Rod 1210 is next secured with set screws to heads 1282b, and 1282c of pedicle screws 1280b, 1280c. The spinal stabilization prosthesis 1270 thus posteriorly secures L5 vertebra 1272b in fixed relationship to sacrum 1272c and is suitable for posterior stabilization of fusion between L5 vertebra 1272b and 1274c.

Owing to the shape of rod 1210, the act of tightening set screws 1284b, 1284c to secure rod 1210 to heads 1282b, 1282c of pedicle screws 1280b, 1280c may cause movement of first end 1211 of rod 1210. With some spinal rods this would apply a load to the post of bone anchor 900 pushing it away from center. However, rod-end 1240 is free to slide somewhat relative to rod 1210 and rotate around rod 1210. These movements of rod-end 1240 compensate for any change in position of first end 1211 of rod 1210 and allow ball 1220 to be positioned directly in line with the longitudinal axis of bone anchor 900. Moreover the centering rod of bone anchor 900 maintains the deflectable in the center position during installation. When rod-end 1240 is properly positioned, set screw 1260 can be tightened as a last step allowing bone anchor 900 to be set up in an ideal position for subsequent support of the L4-L5 segment. Bone anchor 900— when properly implanted as part of spinal prosthesis 1270 permits controlled movement of L4 vertebra 1272a relative to L5 1272b while providing load sharing. Controlled movement of vertebra 1272a relative to vertebra 1272b is enabled by pivoting/rotation of ball 1220 within rod end 1240 in combination with pivoting/rotation of the deflectable post relative to the bone anchor. (See FIG. 12 E).

Figure 12E:
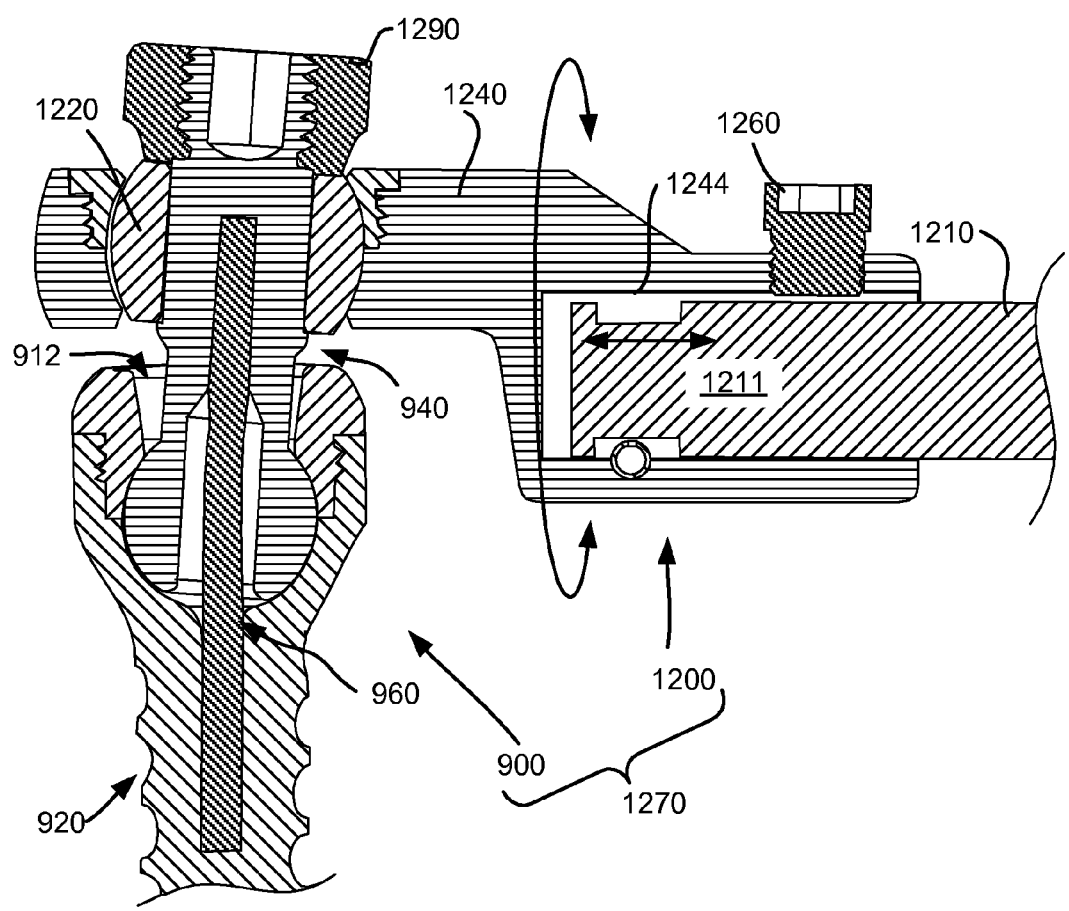
FIG. 12E shows a partial sectional view of a spinal implant prosthesis utilizing the compound spinal rod of FIGS. 12A-12C in conjunction with the bone anchor of FIGS. 9A-9D.

FIG. 12E shows a partial sectional view of a spinal implant prosthesis utilizing the compound spinal rod 1200 of FIGS. 12A-12C in conjunction with the bone anchor 900 of FIGS. 9A-9D. FIG. 12E, illustrates spinal implant prosthesis after securing rod 1210 to pedicle screws 1280b, 1280c (see FIG. 12D) and after securing rod end 1240 to bone anchor 900 with a nut 1290. At this point in implantation the position of first end 1211 of rod 1210 is locked in place. Furthermore, the position of bone screw 920 of bone anchor 900 is also locked in place relative to first end 1211 of rod 1210. Note however, that deflectable post 1240 of bone anchor 900 may pivot away from the neutral position in which it is coaxial with bone screw 920 due to movement of first end 1211 of rod 1210 during securing of rod 1210. However, rod end 1240 can slide and rotate relative to first end 1211 this allows centering rod 960 to push deflectable post 940 back into the neutral position where it is coaxial with bone screw 920 and centered within aperture 912. Once deflectable post 940 is in the neutral/central position, set screw 1260 is tightened against rod 1210 locking rod-end 1240 in position relative to rod 1210. The movements of rod-end 1240 compensate for any change in position of first end 1211 of rod 1210 and allow ball 1220 to be positioned directly in line with the longitudinal axis of bone anchor 900. Moreover the centering rod 1260 of bone anchor 900 helps maintain the deflectable post 1240 in the neutral/center position during installation.

In an alternative embodiment of a spinal prosthesis, a shorter rod 1210 is used and compound spinal rod 1200 spans two vertebra from bone anchor 900 to a single conventional pedicle screw implanted in an adjacent vertebra. Typically, identical or similar stabilization structures are implanted on each side of the spinal column. Furthermore, although compound spinal rod 1200 has been shown in combination with bone anchor 900 of FIGS. 9A-9D, compound spinal rod 1200 can, in other embodiments, be utilized with any other of the bone anchors having deflectable posts described herein.

The bone anchor 900 has a low profile. As a result, compound spinal rod 1200 is mounted closer to the surface of the vertebrae. Moreover, the shape of compound spinal rod 1200 places rod 1210 several millimeters closer to the surface of the vertebrae. Often, the level of the spinal rod is used to guide the depth of placement of the pedicle screw in the adjacent vertebrae. Although the spinal rods can be bent by the surgeon to compensate for any height offset this process is technically difficult. Thus, the surgeons often prefer to arrange the various pedicle screws with the mounting points in alignment the spinal rod without bending. The low profile of bone anchor 900 and compound spinal rod 1200 allow conventional pedicle screw used in conjunction therewith to be mounted with all of threaded shaft implanted in the vertebra and head abutting the surface of the vertebra. This is the preferred location as it reduces stress on the vertebra and conventional pedicle screw by increasing the contact area between pedicle screw and vertebra and reducing the moment arm.

Thus, one of the advantages of bone anchor 900 of FIGS. 9A-9D is the low profile which causes less trauma to tissue and a better position of the system and better alignment with a pedicles screw fully implanted in an adjacent vertebra. The compound spinal rod 1200 of FIGS. 12A-12C enhances the low profile configuration which causes less trauma to tissue and a better position of the system and better alignment with a pedicles screw fully implanted in an adjacent vertebra. In a preferred embodiment, the top of the cap of bone anchor 900 is approximately 10 mm or less above the surface of the vertebra when implanted and the proximal side (furthest from vertebrae) of rod 1210 is approximately 11 mm above the surface of the vertebra. Also in the preferred embodiment, the nut 1290 is no more than about 15 mm from the surface of the vertebrae when implanted. To further reduce the profile, in an alternative embodiment, ball 1220 is threaded to engage a threaded mount (not shown) of deflectable post 940, obviating the need for a separate nut 1290.

Implantation and Assembly Tools

FIGS. 13A-13D and 14A-14F show various steps in the implantation and connection of a dynamic stabilization assembly utilizing embodiments of the bone anchors and spinal rods described herein. Similar methods and devices can be utilized for the various spinal rods and bone anchors described herein as modified for the particular tool engagement features and fasteners provided thereon.

The implantation and assembly is preferably performed in a minimally invasive manner and, thus, tools are provided to facilitate installation and assembly through cannulae. These tools can also be used in open procedures. One suitable minimally invasive approach to the lumbar spine is the paraspinal intermuscular approach. This approach is described for example in "The Paraspinal Sacraspinalis-Splitting Approach to the Lumbar Spine," by Leon L. Wiltse et al., *The Journal of Bone & Joint Surgery*, Vol. 50-A, No. 5, July 1968, which is incorporated herein by reference. In general the patient is positioned prone. Incisions are made posterior to the vertebrae to be stabilized. The dorsal fascia is opened and the paraspinal muscle is split to expose the facet joints and lateral processes of the vertebra. Dynamic bone anchors according to embodiments of the present invention and conventional pedicle screws are placed in the vertebrae as necessary for the selected assembly. The screws are placed lateral to the facet joints and angled in towards the vertebral body. The dynamic rods according to embodiments of the present invention are then inserted into position adjacent the dynamic bone anchors according to embodiments of the present invention, screws and conventional pedicle screws. The balls of the dynamic rods according to embodiments of the present invention are then secured to the deflectable posts of the dynamic bone anchors according to embodiments of the present invention the other end of the dynamic rod is then connected to the conventional screws with the desired interpediclular distance. The implantation of the dynamic bone anchors and connection of the dynamic rods can be facilitated by the implantation tool (FIGS. 13A-13D) and connection tool (FIGS. 14A-14F) described below.

FIG. 13A shows a perspective view of an implantation tool 1350 for use in implanting a dynamic bone anchor 1300. Dynamic bone anchor 1300 may for example bone anchor 800 of FIGS. 8A-8D of bone anchor 900 of FIGS. 9A-9D. Implantation tool 1350 includes an inner shaft 1360 received within a tubular sleeve 1370. Inner shaft 1360 is free to rotate within sleeve 1370. Sleeve 1370 may also be slid towards the proximal end of inner shaft 1360 by pulling on grip 1374. A coil spring 1372 is connected between the sleeve 1370 and inner shaft 1360 to hold sleeve 1370 in its more distal position relative to shaft 1360. The length and diameter of implantation tool 1350 is selected so as to allow use through a cannula in a minimally invasive surgical technique thereby reducing disruption of tissues adjacent the implantation site, reducing patient recovery and improving surgical outcomes.

Referring again to FIG. 13A, shaft 1360 has at a proximal end a quick release mount 1362 to which a handle (not shown) may be attached for turning inner shaft 1360. Suitable handles for attachment to shaft 1360 include ratcheting handles, torque sensing handles and torque limiting handles. In alternative embodiments, a handle may be permanently connected to or integrated with the proximal end of shaft 1362. Inner shaft has at a distal end a head 1364. Head 1364 includes means for engaging and securing dynamic bone anchor 1300 during implantation as is described below.

As also shown in FIG. 13A, head 1364 can be received over the proximal portion of dynamic bone anchor 1300 with the ball rod 1306 received within shaft 1360 (see dashed line). In use, dynamic bone anchor 1300 is inserted into the head 1364 of shaft 1360 with the cap 1310 engaged by head 1364 and the ball rod 1306 secured within head 1364. Dynamic bone anchor 1300 is thus secured to implantation tool 1350. Dynamic bone anchor 1300 will not be released unless and until the surgeon pulls back on grip 1374. Thus, dynamic bone anchor 1300 and implantation tool can be inserted as one unit through a cannula to the implantation location in the spine facilitating the positioning and implantation of dynamic bone anchor 1300.

FIG. 13B shows a detailed sectional view of the head 1364 of the implantation tool 1350 of FIG. 13A engaged with a dynamic bone anchor 1300. As shown in FIG. 13B, head 1364 includes a socket 1365 for receiving and engaging cap 1310 of dynamic bone anchor 1300. Socket 1365 is designed to mate with cap 1310 in order to rotate the threaded shank 1320 of dynamic bone anchor 1300. Thus, the interior of socket 1365 may be hexagonal, octagonal or provided with flutes/splines etc., depending on the particular configuration of the cap 1310. Socket 1365 should be able to apply sufficient torque to cap 1310 to implant the dynamic bone anchor 1300 in a pedicle.

Referring again to FIG. 13B, head 1364 also includes a bore 1366 for receiving ball rod 1306 of dynamic bone anchor. As shown in FIG. 13B, ball rod 1306 includes a nipple 1318 at the proximal end. A ball 1352 is positioned within an aperture 1367 which passes from the exterior of shaft 1360 intersecting bore 1366 adjacent nipple 1318. Ball 1352 is held by sleeve 1370 in a position in which ball 1352 protrudes into bore 1366 so as to trap nipple 1352 within bore 1365. In a preferred embodiment, there are three such balls, however, only one is shown in this sectional view. Thus, cap 1310 is received in socket 1365 and dynamic bone anchor 1300 is locked to implantation tool 1350 by the interaction of nipple 1318 and ball(s) 1352.

FIG. 13C shows a detailed sectional view of the head 1364 of the implantation tool 1350 of FIG. 13A configured to release a dynamic bone anchor 1300. After implantation of dynamic bone anchor 1300 it is necessary to remove implantation tool 1350. The first step is to slide sleeve 1370 proximally relative to shaft 1360 as shown by arrow A. This is achieved by pulling back on grip 1374 against the force of spring 1372 (See FIG. 13A). As sleeve 1360 is pulled proximally, ball(s) 1352 enters a portion of sleeve 1360 with a larger internal diameter. Ball(s) 1352 can move away from engagement with ball rod 1306 as they pass ramp 1368 releasing nipple 1318. At this stage both shaft 1360 and sleeve 1370 can be pulled together away from dynamic bone anchor 1300.

Figure 13D:
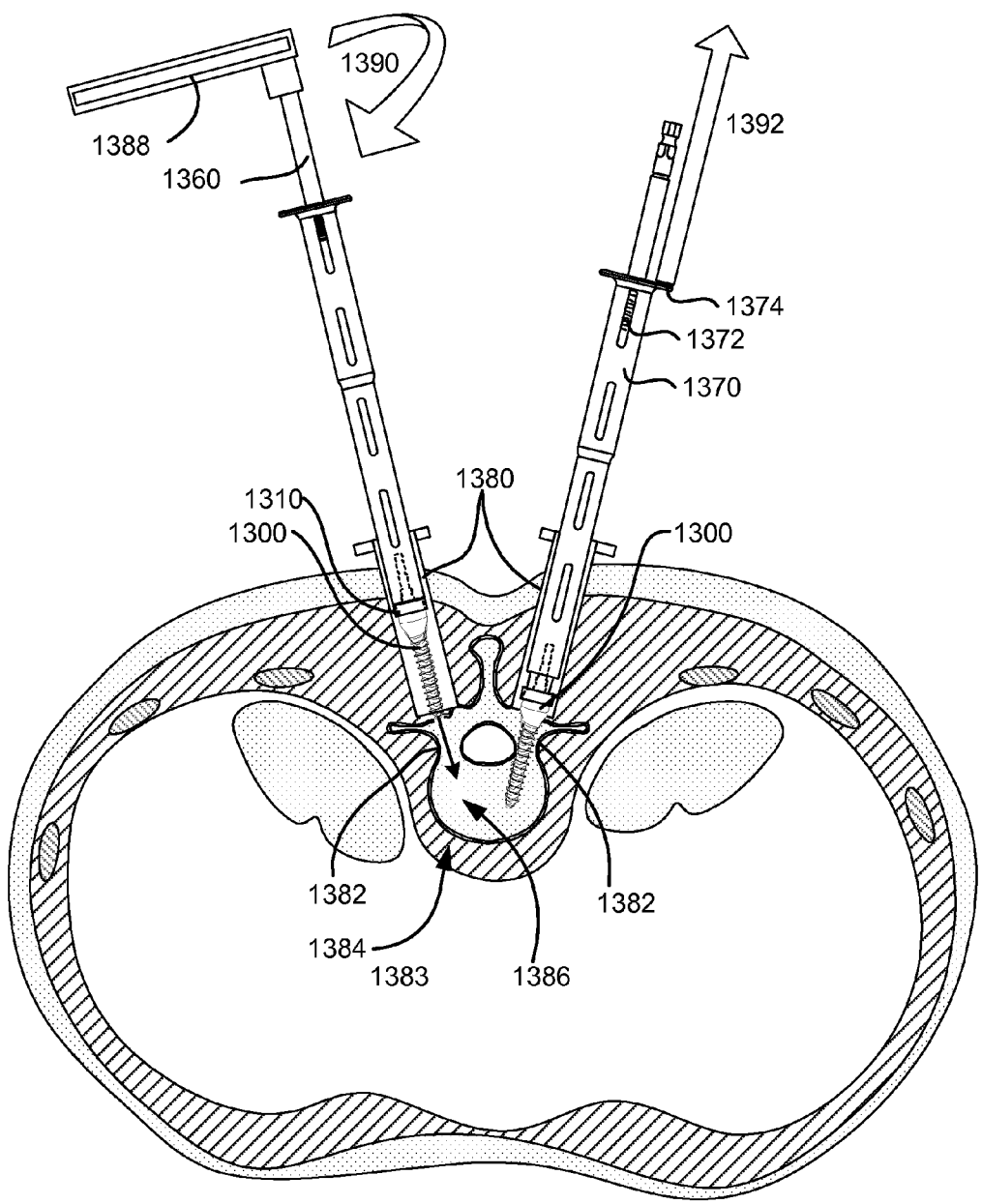
FIG. 13D is a transverse view of the lumbar spine illustrating use of the implantation tool of FIG. 13A to implant a dynamic bone anchor in the pedicles of a lumbar vertebra according to an embodiment of the invention.

FIG. 13D shows a transverse view of the lumbar spine illustrating use of the implantation tool 1350 of FIG. 13A to implant dynamic bone anchors 1300 in the pedicles 1382 of a lumbar vertebra 1384 according to an embodiment of the invention. As shown in FIG. 13D, implantation tool 1350 may be used through a cannula 1380 to implant the dynamic bone anchor in a minimally invasive procedure. The cannula 1380 is introduced to the patient to approach the pedicles posteriorly. The pedicle 1382 of the vertebra is 1384 is exposed in the conventional fashion. A hole 1386 is then drilled through the pedicle 1382 into the vertebral body 1383 of the vertebra. Next a dynamic bone anchor 1300 is selected having of suitable length, diameter and force/deflection characteristics is selected for implantation. The cap 1310 of the selected dynamic bone anchor 1300 is inserted into the head 1364 of implantation tool 1350 and secured in place.

Referring now to the left side of FIG. 13D, dynamic bone anchor 1300 and implantation tool 1350 are inserted as one assembly through cannula 1380 to the implantation site. Then dynamic bone anchor is implanted by turning a handle 1388 attached to the quick release on the proximal end of shaft 1360. The dynamic bone anchor 1300 is driven into hole 1386 until the housing is at the surface of the vertebra 1384 (see arrow 1390). The torque to drive dynamic bone anchor 1300 is provided by handle 1388 through shaft 1360 to cap 1310 of dynamic bone anchor 1300.

Referring now to the right side of FIG. 13D, when dynamic bone anchor 1300 is correctly positioned in pedicle 1382, the physician pulls back on grip 1374 against the force of spring 1372. Sleeve 1370 moves proximally relative to shaft 1360. Shaft 1360 releases the grip on dynamic bone screw 1300 and the both shaft 1360 and sleeve 1370 move away from cannula 1380 and out of the patient (see arrow 1392). Dynamic bone anchor 1300 is now correctly implanted and prepared for attachment to spinal rod and/or other spinal stabilization assembly components.

Figure 14A:
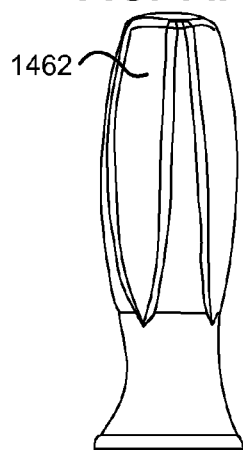
FIG. 14A shows a perspective view of an attachment tool for securing a dynamic spinal rod to a dynamic bone anchor according to an embodiment of the invention.

FIGS. 14A-14D show views of an attachment tool for securing a spinal rod 1400 to a dynamic bone anchor 1300 according to an embodiment of the invention. FIG. 14A shows a perspective view of an attachment tool 1450 for securing a dynamic spinal rod 1400 to a dynamic bone anchor 1300 (shown in FIG. 14C) according to an embodiment of the invention. Dynamic spinal rod 1400 may be, for example, the compound spinal rod 500 of FIGS. 5A-5C, or spinal rod 710 of FIGS. 7A-7C, or compound spinal rod 1200 of FIGS. 12A-12E. Dynamic bone anchor 1300 may be, for example, bone anchor 800 of FIGS. 8A-8D or bone anchor 900 of FIGS. 9A-9D.

Referring first to FIG. 14A, attachment tool 1450 includes an inner shaft 1460 received within a tubular sleeve 1470. The length and diameter of attachment tool 1450 is selected so as to allow use through a cannula in a minimally invasive surgical technique thereby reducing disruption of tissues adjacent the implantation site, reducing patient recovery time and improving surgical outcomes. Inner shaft 1460 is free to rotate and slide within sleeve 1470. Inner shaft 1460 has at a proximal end an attached handle 1462. In alternative embodiments shaft 1460 may have a fitting to which a handle might be attached, for example, ratcheting handles, torque sensing handles and torque limiting handles Inner shaft has at a distal end a head 1464 for engaging and securing the hex extension of a dynamic spinal rod 1400 (see FIG. 14B).

Figure 14B:
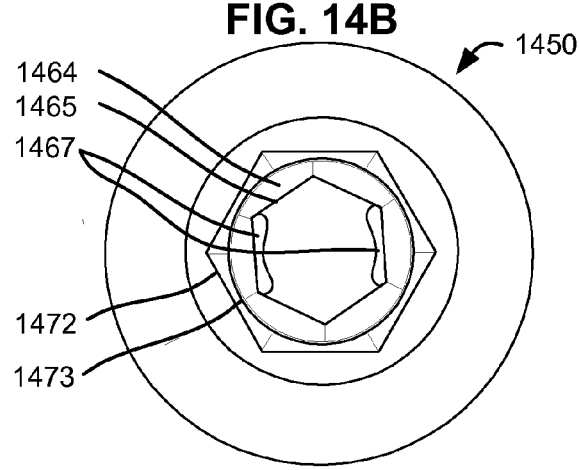
FIG. 14B shows a detailed view of the head of the attachment tool of FIG. 14A.

Referring again to FIG. 14A, sleeve 1470 includes a butterfly grip 1474 at the proximal end thereof. Sleeve 1470, has at the distal end thereof, means for engaging and securing the female hex socket of a ball of a dynamic spinal rod 1400 during connection to a dynamic bone anchor as is described below. In a preferred embodiment head 1464 includes a male hex fitting 1472 with a central aperture 1473. FIG. 14B shows an enlarged view of head 1464 from the distal end of attachment tool 1450. FIG. 14B shows male hex fitting 1472 with central aperture 1473. Through central aperture 1473 is visible female hex socket 1465 of head 1464. Protruding into female hex socket 1465 are two spring tabs 1467.

Figure 14C:
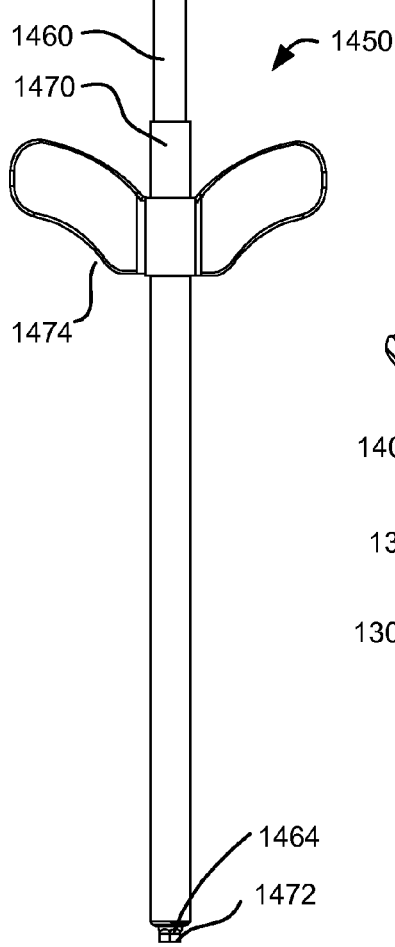
FIGS. 14C and 14D show detailed sectional views of the head of the attachment tool of FIG. 14A in relation to a dynamic spinal rod and bone anchor.
Figure 14D:
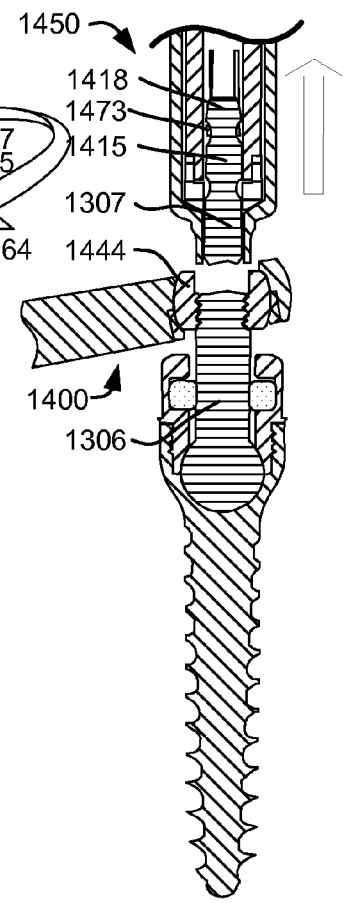

FIGS. 14C and 14D show detailed sectional views of the distal end attachment tool 1450 in relation to a dynamic spinal rod 1400 and dynamic bone anchor 1300. Referring first to FIG. 14C, which shows a detailed sectional view of the distal end of the attachment tool 1450 of FIG. 14A, engaged with a dynamic spinal rod 1400 and a dynamic bone anchor 1300. As shown in FIG. 14C, male hex fitting 1472 of head 1464 of outer sleeve 1470 fits into the female hex socket of ball 1444. At the same time a hex extension 1307 of ball rod 1306 is received within female hex socket 1465 of inner shaft 1460. When thus engaged, turning handle 1462 (Seen in FIG. 14A) relative to butterfly grip 1474 (Seen in FIG. 14A) can rotate ball rod 1306 relative to ball 1444. Attachment tool 1450 is designed to apply sufficient torque to ball rod 1306 relative to ball 1444 to secure ball rod 1306 to ball 1444 and breakaway the hex extension 1307 of ball rod 1306. In a preferred embodiment, attachment tool 1450 should be able to provide greater than 30 foot pounds of torque.

FIG. 14D shows a detailed sectional view of the distal end of the attachment tool 1450 of FIG. 14A after break away of hex extension 1307 of ball rod 1306. As shown in FIG. 14D, when ball 1444 has been tightened onto ball rod 1306, tabs 1467 (Seen in FIG. 14B) on central aperture 1473 engage either side of a nipple 1418 of hex extension 1307 to secure hex extension 1307 within female hex socket 1465. Thus, when hex extension 1307 beaks away it can be removed from the patient with connection tool 1450 as shown.

FIGS. 14E-14H are lateral views of the lumbar spine illustrating steps of attaching a dynamic spinal rod 1400 to a dynamic bone anchor 1300 utilizing the attachment tool of FIG. 14A according to an embodiment of the invention. As shown in FIG. 14E, the dynamic spinal rod 1400 is implanted after the dynamic bone anchor 1300 and a polyaxial screw 1440 have already been implanted. Dynamic spinal rod 1400 is implanted in a cranially direction—preferably in a minimally invasive manner until dynamic spinal rod 1400 is positioned adjacent dynamic bone anchor 1300 and polyaxial screw 1440. The hex extension 1307 of dynamic bone anchor 1300 is then fed through ball 1444 (not shown) of dynamic spinal rod 1400 as shown.

Next, as shown in FIG. 14F, connection tool 1450 is inserted through a cannula 1380 to engage ball 1444 and hex extension 1307. Ball 1444 is then turned relative to hex extension 1307 until it is fully secured to ball rod 1306. When ball 1444 is fully secured to ball rod 1306, further torque is applied until hex extension 1307 (not shown) is sheared off. In a preferred embodiment, this requires 30 foot pounds of torque and is sufficient to lock ball 1444 to ball rod 1306. Next, as shown in FIG. 14G, connection tool 1450 can be removed from cannula 1380. As previously described, hex extension 1307 (not shown) is retained inside attachment tool 1450 for easy removal from the patient. As shown in FIG. 14H a conventional tool 1484 is then inserted through cannula 1480 to operate polyaxial screw 1440 to secure the other end of dynamic spinal rod 1400.

FIGS. 15A-15D illustrate another alternative bone anchor 1500. FIG. 15A shows an exploded view of bone anchor 1500. FIG. 15B shows a perspective view of bone anchor 1500, as assembled. FIG. 15C shows a sectional view of bone anchor 1500. FIG. 15D illustrates deflection of the deflectable post of bone anchor 1500. Referring first to FIG. 15A, bone anchor 1500 includes, in this embodiment, four components: bone screw 1520, deflectable post 1540, centering rod 1560, and cap 1510. Bone screw 1520 comprises a threaded shaft 1522 with a housing 1530 at one end. Housing 1530 is provided with tool engagement features 1536 which are adapted to be engaged by a wrench (not shown) to drive threaded shaft 1522 into a bone. Housing 1530 is preferably formed in one piece with threaded shaft 1522. Housing 1530 has a cavity 1532 oriented along the axis of threaded shaft 1522. Cavity 1532 is open at the proximal end of housing 1530 and is configured to receive deflectable post 1540.

Centering rod 1560 is a cylindrical rod having a metal core 1561 covered with a tubular polymer sleeve 1563. In a preferred embodiment core 1561 is made of a superelastic metal—for example nitinol. In one embodiment, core 1561 is a superelastic nitinol wire having a diameter between 0.060 and 0.080 inches. In an exemplary embodiment core 1561 is a superelastic nitinol wire having a diameter of 0.063 inches. In a preferred embodiment sleeve 1563 is made of a wear-resistant biocompatible polymer—for example PEEK.

The proximal end 1562 of centering rod 1560 is sized and configured to be received within deflectable post 1540. The distal end 1564 of centering rod 1560 is sized and configured to be received within bone screw 1520. In a preferred embodiment both ends of centering rod 1560 are cylindrical in shape. However, in alternative embodiments, the proximal end 1562 and distal end of rod 1560 may have other than a circular section, for example, square, oval, rectangular, or other polygonal. Note that the distal end 1564 and proximal end 1562 of centering rod 1560 can have the same, or different, sectional shapes.

The center section 1566 of centering rod 1560 is designed to bend in response to deflection of deflectable post 1540 relative to bone screw 1520 and exert a restorative centering force upon deflectable post 1540. The restorative force tends to align the longitudinal axis of the deflectable post 1540 with the longitudinal axis of the bone screw 1520. The force increases as the angle between the deflectable post 1540 and bone screw 1520 increases. The diameter and shape of center section 1566 of centering rod 1560 can be designed/selected to achieve a desired restorative force for a given angle and/or direction of deflection. Also, the diameter of core 1361 and thickness of sleeve 1363 can be selected to achieve a desired restorative force. Center section 1566 can be cylindrical but may have other than a circular section, for example, square, oval, rectangular, or other polygonal. The force/deflection response can accordingly be isotropic or anisotropic depending upon the shape of center section 1566.

A hemispherical pocket 1539 (shown by dashed lines) is formed in the bottom of cavity 1532 of housing 1530. A bore 1534 (shown by dashed lines) extends distally from the bottom of hemispherical pocket 1539 along the longitudinal axis of bone screw 1520. Bore 1534 is sized and configured to receive the distal end 1564 of centering rod 1560. Bore 1534 is chamfered where it meets hemispherical pocket 1539 to allow for bending of centering rod 1560. In a preferred embodiment both centering rod 1560 and bore 1534 are cylindrical in shape such that the distal end 1564 of centering rod 1560 may rotate about its longitudinal axis within bore 1534.

Deflectable post 1540 can be made, for example, from cobalt chrome or titanium. In a preferred embodiment deflectable post 1540 is between 4.5 and 6.5 mm in diameter and made in one piece from cobalt chrome. Deflectable post 1540 has a retainer 1542 at the distal end. Retainer 1542 is a ball-shaped or spherical structure in order to form part of a linkage connecting deflectable post 1540 to bone screw 1520. At the proximal end of deflectable post 1540 is a mount 1544. Mount 1544 is a low profile mount configured to connect deflectable post 1540 to a vertical rod component (not shown, but see, e.g. FIGS. 5A-5C). Mount 1544 comprises a threaded section 1546 to which the vertical rod component may be secured. Mount 1544 has at the proximal end a socket 1549 which can be engaged by a wrench during the securing of a vertical rod to mount 1544.

A bore 1570 (show by dashed lines) extends proximally from the bottom of ball-shaped retainer 1542 along the longitudinal axis of deflectable post 1540. Bore 1570 includes a proximal bore 1572 sized and configured to receive the proximal end 1562 of centering rod 1560. Bore 1570 has a larger distal bore 1576. Distal bore 1576 is sized to allow bending of centering rod 1560 and deflection of deflectable post 1540. In some embodiments, distal bore 1576 is sized such that center section 1566 does not contact the sides of distal bore 1576 over the full range of motion of deflectable post 1540. In alternative embodiments, distal bore 1576 is sized and shaped such that center section 1566 comes into contact progressively with the sides of distal bore 1576 over the range of motion of deflectable post 1540 thereby modulating the centering force. The sleeve 1563 protects the core 1561 of centering rod 1560 from wear during moving contact with distal bore 1576. Distal bore 1576 is chamfered where it intersects the surface of retainer 1542. In a preferred embodiment both centering rod 1560 and proximal bore 1572 are cylindrical in shape such that the proximal end 1562 of centering rod 1560 may rotate about its longitudinal axis within proximal bore 1572.

Referring again to FIG. 15A, a cap 1510 is designed to perform multiple functions including securing retainer 1542 in cavity 1532 of bone screw 1520. Cap 1510 has a central aperture 1512 for receiving deflectable post 1540. As shown in FIG. 15A, cap 1510 comprises a cylindrical shield section 1518 connected to a collar section 1516. Shield section 1518 is designed to mate with cavity 1532 of housing 1530. The distal end of shield section 1518 comprises a curved flange 1519 for securing retainer 1542 within cavity 1532 of housing 1530. Shield section 1518 is threaded adjacent collar section 1516 in order to engage threads at the proximal end of cavity 1532 of housing 1530. Cap 1510 can be provided with surface features for engagement by a tool during attachment of cap 1510 to housing 1530 (such surface features can also be used to drive bone screw 1520 into a bone). For example, cap 1510 may be hexagonal or octagonal in shape or may have splines, sockets and/or flutes and/or other registration elements.

Bone anchor 1500 is assembled prior to implantation in a patient. FIG. 15B shows a perspective view of bone anchor 1500 as assembled. During assembly, centering rod 1560 (shown by dashed lines) is received in bore 1570 and bore 1534 (see FIGS. 15A and 15C). Because bore 1570 and bore 1534 are closed, it is not necessary to fix centering rod 1560 to either of deflectable post 1540 or bone screw 1520. However, if desired, centering rod 1560 can be attached to either or both of deflectable post 1540 or bone screw 1520 by mechanical means (e.g. pins), welding or other fastening method/device. Retainer 1542 (not shown) is received in hemispherical pocket 1539 (not shown). Deflectable post 1540 is then positioned through aperture 1512 of cap 1510. Cap 1510 is then secured to the threaded end of cavity 1532 (see FIGS. 15A and 15C) of housing 1530 of bone screw 1520. Cap 1510 may alternatively or additionally be laser welded to housing 1530 after installation. Cap 1510 secures retainer 1542 within cavity 1532 of bone screw 1520. Deflectable post 1540 extends out of housing 1530 and cap 1510 such that mount 1544 is accessible for connection to a vertical rod. Bone anchor 1500 is typically implanted in a bone in the configuration shown in FIG. 15B and prior to attachment of a vertical rod or other spinal rod. A tool may be used to engage the surface features 1536 of housing 1530 during implantation of bone anchor 1500 into a bone (See, e.g. FIGS. 13A-13D).

FIG. 15C shows a sectional view of a bone anchor 1500 after assembly. Retainer 1542 fits into a hemispherical pocket 1539 in the bottom of cavity 1532 of housing 1530. The distal edge of cap 1510 includes the curved flange 1519 which secures ball-shaped retainer 1542 within hemispherical pocket 1539 while allowing ball-shaped retainer 1542 to pivot and rotate. Accordingly, in this embodiment, a ball-joint is formed. Deflectable post 1540 pivots about a pivot point 1503 indicated by an X. In a preferred embodiment the pivot point 1503 is positioned on the center of the section of centering rod 1560 (at least when the longitudinal axis of the deflectable post 1540 and bone screw 1520 are aligned). Deflectable post 1540 may pivot about pivot point 1503 in any direction, as shown by arrow 1550. Concurrently or alternatively, deflectable post 1540 can rotate, as shown by arrow 1552, about the long axis of deflectable post 1540 (which also passes through pivot point 1503).

As shown in FIG. 15C, distal end 1564 of centering rod 1560 is received within bore 1534 of bone screw 1520. Proximal end 1562 of centering rod 1560 is received within proximal bore 1572 of deflectable post 1540. Center section 1566 of centering rod 1560 is received within distal bore 1576 of deflectable post 1540. Note that an annular cavity 1574 exists around center section 1566 leaving center section 1566 free to flex when deflectable post 1540 pivots about pivot point 1503.

Where flexible components are incorporated in a spinal device, one important consideration is the possibility of failure of the flexible element during the life of the device. One advantage of the present design of bone anchor 1500 is that the centering rod 1560 is not relied upon for securing mount 1544 to bone screw. 1520. Thus, if centering rod 1560 fails at some point, mount 1544 and any spinal components connected to it remain attached to bone screw 1520. Thus it is an advantage of the present design of bone anchor 1500 that, the failure mode for the "flexible element" of this design is fundamentally safe.

It is also advantageous that, in the present design centering rod 1560 is fully enclosed within bore 1570 and bore 1534. Thus, where core 1561 is nitinol and sheath 1563 is PEEK, the nitinol and PEEK are not in direct contact with tissues of the body. Furthermore, even if centering rod 1560 fails, no parts of centering rod 1560 can migrate past ball 1542 into the tissues surrounding bone anchor 1500. Thus it is an advantage of the present design of bone anchor 1500 that the flexible nitinol/PEEK element is entirely enclosed within the device and not exposed to contact with tissues.

FIG. 15D shows a sectional view of bone anchor 1500 and illustrates deflection of deflectable post 1540. Applying a force to mount 1544 causes deflection of deflectable post 1540 of bone anchor 1500. Deflectable post 1540 pivots about pivot point 1503 located at the center of ball-shaped retainer 1542. Proximal end 1562 of centering rod 1560 remains aligned with deflectable post 1540 whereas distal end 1564 remains aligned with bone screw 1520. Thus center section 1566 of centering rod 1560 bends elastically in response to deflection of deflectable post 1540. Centering rod 1560 thus applies a resilient restorative force upon deflectable post 1540 pushing it back into alignment with bone screw 1520. The magnitude of the force increases as the deflection increases. The magnitude of the force can be selected based on the configuration and material of centering rod 1560. For example a larger diameter cylindrical nitinol rod core 1561 will provide a larger centering force than a smaller diameter rod for the same amount of deflection. In a preferred embodiments centering rod 1560 is floating, that is to say that it is not fixed to one or both of deflectable post 1540 and bone screw 1520. Thus, upon deflection of deflectable post 1540, centering rod 1560 can slide somewhat in one or both of proximal bore 1572 and bore 1534 such that the centering rod 1560 is not placed under longitudinal tension during deflection of deflectable post 1540.

In a preferred embodiment, deflectable post 1540 may deflect from 0.5 mm to 2 mm in any direction before making contact with limit surface 1513. More preferably, deflectable post 1540 may deflect approximately 1 mm before making contact with limit surface 1513. After a fixed amount of deflection, deflectable post 1540 comes into contact with limit surface 1513 of cap 1510. Limit surface 1513 is oriented such that when deflectable post 1540 makes contact with limit surface 1513, the contact is distributed over an area to reduce stress on deflectable post 1540. In this embodiment, the deflectable post 1540 contacts the entire sloping side of the conically-shaped limit surface 1513. After deflectable post 1540 comes into contact with limit surface 1513, further deflection requires deformation (bending) of deflectable post 1540. Bending of deflectable post 1540 requires significantly more force than bending of centering rod 1560.

As previously stated, the deflection/force response of a centering rod (and a ball-joint incorporating such a centering rod) can be customized based on the choice of design, dimensions and materials. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine for providing in a kit for a doctor to use. After a selected amount of deflection a deflectable post (see e.g. deflectable post 1540 of FIGS. 15A-9D) will make contact with a limit surface (for example 1 mm of deflection. Further deflection then requires bending of the deflectable post 1540. The deflectable post 1540 therefore responds more stiffly as the load increases. As the deflection increases, the stiffness of the deflectable post 1540 to further deflection is increased such that the force required per unit of additional deflection increases in response to the load placed on the spine and deflection rod.

Initially, as load or force is first applied to the deflectable post by the spine, the deflection of the deflectable post rod responds about linearly to the increase in the load. After the post makes contact with the limit surface, the deflectable post responds more stiffly. In this region, a greater amount of load or force needs to be placed on the deflectable post in order to obtain the same amount of deflection that was realized prior to this point. Accordingly, the deflectable post of this example provides a range of motion where the load supported increases about linearly as the deflection increases and then with increased deflection the load supported increases more rapidly in a non-linear manner. The transition from lower stiffness to higher stiffness region depends upon the distance between the deflectable post and the limit surface of the cap. This distance may be customized as previously described so that the transition occurs after the desired amount of deflection, for example after about 1 mm of deflection or after about 2 mm of deflection.

As shown, in the embodiment of FIG. 15D, sheath 1563 of centering rod 1560 makes contact with the walls of distal bore 1576 upon deflection of deflectable post 1540. Sheath 1563 thereby protects core 1561 from wear during moving contact with the walls of distal bore 1576. Furthermore, sheath 1563, is in some embodiments compressed between core 1561 and the walls of distal bore 1576. Thus sheath 1563 being resilient will modulate and contribute to the restorative force applied to deflectable post 1540 by centering rod 1560. The effect of sheath 1563 can be adjusted by modifying the thickness and/or material of sheath 1563. For example, PEEK of different durometers can be selected for sheath 1563 thereby resulting in a different force/deflection response for deflectable post 1540.

Deflection Rod/Loading Rod Materials

Movement of the deflectable post relative to the bone anchor provides load sharing and dynamic stabilization properties to the dynamic stabilization assembly. As described above, deflection of the deflectable post deforms the material of the sleeve. In some embodiments, the characteristics of the material of the sleeve in combination with the dimensions of the components of the deflection rod assembly affect the force-deflection curve of the deflection rod. In other embodiments, the characteristics of the material of the centering rod in combination with the dimensions of the components of the assembly affect the force-deflection curve of the assembly.

The deflectable post, bone anchor, compound rods, centering rods, and spinal rods are preferably made of biocompatible implantable metals. The deflectable post can, for example, be made of titanium, titanium alloy, cobalt chrome alloy, a shape memory metal, for example, nitinol (NiTi) or stainless steel. In preferred embodiments, the deflectable post is made of cobalt chrome alloy. In preferred embodiments, the bone anchor and spinal rods are made of titanium or titanium alloy; however, other materials, for example, stainless steel may be used instead of or in addition to the titanium\titanium alloy components. Furthermore, the ball of the dynamic spinal rod is preferably made of cobalt chrome for good wear characteristics.

The material of the sleeve/compliant member/o-ring (where present) is a biocompatible and implantable polymer having the desired deformation characteristics. The material of the sleeve should also be able to maintain the desired deformation characteristics. Thus the material of the sleeve is preferably durable, resistant to oxidation and dimensionally stable under the conditions found in the human body. The sleeve may, for example be made from a polycarbonate urethane (PCU) such as Bionate®. If the sleeve is comprised of Bionate®, a polycarbonate urethane or other hydrophilic polymer, the sleeve can also act as a fluid-lubricated bearing for rotation of the deflectable post relative to the longitudinal axis of the deflectable post.

The material of the sheath of the centering rod (where present) is a biocompatible and implantable polymer having the desired deformation characteristics. The material of the sheath should also be able to maintain the desired deformation characteristics. Thus the material of the sheath is preferably durable, resistant to oxidation and dimensionally stable under the conditions found in the human body. Suitable material includes by way of example only polyetheretherketone (PEEK), polyetherketoneketone (PEKK), polyetherketone (PEK), polyetherketoneetherketoneketone (PEKEKK), and polyetheretherketoneketone (PEEKK). Still, more specifically, the material can be PEEK 450G, which is an unfilled PEEK approved for medical implantation available from Victrex of Lancashire, Great Britain. (Victrex is located at www-.matweb.com or see Boedeker www.boedeker.com). Other sources of this material include Gharda located in Panoli, India (www.ghardapolymers.com). As will be appreciated by those of skill in the art, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. Reference to other appropriate polymers that can be used in the sheath can be found in the following documents: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and PCT Publication WO 02/00270 A1, dated Jan. 3, 2002, entitled "Bio-Compatible Polymeric Materials." The sheath for the centering rod may also be made, for example, from a polycarbonate urethane (PCU) such as Bionate®.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated.

The particular dynamic stabilization assemblies shown herein are provided by way of example only. It is an aspect of preferred embodiments of the present invention that a range of components be provided and that the components may be assembled in different combinations and organizations to create different assemblies suitable for the functional needs and anatomy of different patients. Also, bone anchors and deflection rods having different force deflection characteristics may be incorporated at different spinal levels in accordance with the anatomical and functional requirements. Spinal stabilization may be provided at one or more motion segments and in some cases dynamic stabilization may be provided at one or more motion segments in conjunction with fusion at an adjacent motion segment.

Particular embodiments of stabilization assemblies may incorporate combinations of the bone anchors, spinal rods, deflection rods, deflectable posts, centering rods, compound rods, offset and coaxial connectors described herein, and in the related applications incorporated by reference, and standard spinal stabilization and/or fusion components, for example screws, pedicle screws, polyaxial screws and rods.—additionally, any of the implantation tools and methods described herein, and in the related applications incorporated by reference can be used or modified for use with such stabilization assemblies. It is intended that the scope of the invention be defined by the claims and their equivalents.

What is claimed is:

1. A spinal stabilization device comprising:
   a centering rod having an inner core and an outer sheath;
   the centering rod having a first end, a second end and a flexible section connecting the first end and the second end;
   a ball-rod including at least a partial ball-shaped retainer and a rod;
   a first bore extending along a longitudinal axis of the ball-rod and opening through the ball-shaped retainer opposite the rod, wherein the first end of the centering rod is received in the first bore;
   a housing;
   a socket within the housing, wherein the socket partially encloses the ball-shaped retainer to form a ball-joint;
   a channel extending from the socket out of the housing, wherein the rod of the ball-rod extends through the channel out of the housing; and
   a second bore in the housing extending from the socket opposite the channel, wherein the second end of the centering rod is received in the second bore;
   whereby deflection of the ball-rod bends the flexible section of the centering rod and the centering rod exerts a restoring force to center the rod of the ball-rod within the channel.

2. The spine stabilization device of claim 1, wherein the channel comprises a frusto-conical surface positioned to contact the rod after a predetermined amount of deflection of the rod from center of the channel.

3. The spine stabilization device of claim 1, wherein said inner core of said centering rod is made of a super-elastic metal.

4. The spine stabilization device of claim 1, wherein said inner core of said centering rod is made of nitinol.

5. The spine stabilization device of claim 1, wherein said outer sheath of said centering rod is made of a biocompatible polymer.

6. The spine stabilization device of claim 1, wherein said outer sheath of said centering rod is made of PEEK.

7. The spine stabilization device of claim 1, wherein the first bore further comprises an enlarged portion within the ball-shaped retainer, wherein the flexible section of the centering rod is received in the enlarged portion of the first bore.

8. The spine stabilization device of claim 1, wherein said housing further comprises a threaded bone anchor.

9. The spine stabilization device of claim 1, wherein said ball-rod also includes a threaded mount external to the housing adapted to connect a spinal implant to the ball-rod component.

10. The spine stabilization device of claim 1, wherein said ball-rod is made of cobalt chrome alloy.

11. A spine stabilization device comprising:
a first element;
a second element; and
a self-centering ball-joint connecting the first element and the second element;
wherein the self-centering ball-joint includes,
a housing having a socket;
a ball-rod received in the socket; and
a centering rod having an inner core and an outer sheath, the centering rod received partially within the ball-rod and partially within the housing; and
whereby deflection of the ball-rod bends the centering rod and the centering rod exerts a restoring force on the ball-rod.

12. The spine stabilization device of claim 11, wherein said inner core of said centering rod is made of a super-elastic metal.

13. The spine stabilization device of claim 11, wherein said inner core of said centering rod is made of nitinol.

14. The spine stabilization device of claim 11, wherein said outer sheath of said centering rod is made of a biocompatible polymer.

15. The spine stabilization device of claim 11, wherein said outer sheath of said centering rod is made of PEEK.

16. The spine stabilization device of claim 11, wherein the first element is a bone anchor.

17. A spine stabilization device comprising:
a bone anchor;
a deflectable mount; and
a self-centering ball-joint connecting the bone anchor and the deflectable mount;
wherein the self-centering ball-joint includes,
a housing having a socket;
a ball-rod received in the socket; and
a centering rod having an inner core and an outer sheath, the centering rod received partially within the ball-rod and partially within the housing;
whereby deflection of the ball-rod bends the centering rod and the centering rod exerts a restoring force on the ball-rod.

18. The spine stabilization device of claim 17, wherein said inner core of said centering rod is made of a super-elastic metal and said outer sheath is made of a biocompatible polymer.

19. The spine stabilization device of claim 17, wherein said inner core of said centering rod is made of nitinol and said outer sheath is made of PEEK.

20. The spine stabilization device of claim 17, wherein said bone anchor is formed in one piece with said housing and said deflectable mount is formed in one piece with said ball-rod.

21. A spine stabilization device comprising:
a first element;
a second element; and
a self-centering joint connecting the first element and the second element;
wherein the self-centering joint includes,
a housing having a socket;
a retainer received in the socket such that the retainer is deflectable relative to the housing; and
a centering rod having an inner core and an outer sheath, the centering rod received partially within retainer and partially within the housing; and
whereby deflection of the retainer bends the centering rod and the centering rod exerts a restoring force on the retainer.

22. The spine stabilization device of claim 21, wherein said inner core of said centering rod is made of a super-elastic metal.

23. The spine stabilization device of claim 21, wherein said inner core of said centering rod is made of nitinol.

24. The spine stabilization device of claim 21, wherein said outer sheath of said centering rod is made of PEEK.

25. The spine stabilization device of claim 21, wherein the first element is a bone anchor.

26. A spine stabilization device comprising:
a bone anchor;
a deflectable mount; and
a self-centering joint connecting the bone anchor and the deflectable mount;
wherein the self-centering joint includes,
a housing having a socket;
a retainer pivotably received in the socket; and
a centering rod having an inner core and an outer sheath, the centering rod received partially within the retainer and partially within the housing;
whereby deflection of the retainer bends the centering rod and the centering rod exerts a restoring force on the retainer.

27. The spine stabilization device of claim 26, wherein said inner core of said centering rod is made of a super-elastic metal and said outer sheath is made of a biocompatible polymer.

28. The spine stabilization device of claim 26, wherein said inner core of said centering rod is made of nitinol and said outer sheath is made of PEEK.

29. The spine stabilization device of claim 17, wherein said bone anchor is formed in one piece with said housing and said deflectable mount is formed in one piece with said retainer.

* * * * *